(12) United States Patent  
Gravestock et al.

(10) Patent No.: US 7,081,538 B1
(45) Date of Patent: Jul. 25, 2006

(54) SUBSTITUTED ISOXAZOLINES AND THEIR USE AS ANTIBACTERIAL AGENTS

(75) Inventors: Michael Barry Gravestock, Waltham, MA (US); Michael John Betts, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 516 days.

(21) Appl. No.: 10/111,562

(22) PCT Filed: Nov. 28, 2000

(86) PCT No.: PCT/GB00/04516

§ 371 (c)(1),
(2), (4) Date: Aug. 28, 2002

(87) PCT Pub. No.: WO01/40222

PCT Pub. Date: Jun. 7, 2001

(30) Foreign Application Priority Data

Dec. 3, 1999 (GB) .................... 9928568.6

(51) Int. Cl.
*A61K 31/505* (2006.01)
*A61K 31/42* (2006.01)
*C07D 413/06* (2006.01)

(52) U.S. Cl. ............ 548/240; 548/243; 548/244; 548/245; 544/333; 546/209; 546/272.1; 514/256; 514/275; 514/326; 514/340; 514/378; 514/380

(58) Field of Classification Search ........... 548/240, 548/243, 244, 245; 544/333; 546/209, 272.1; 514/256, 275, 326, 340, 378, 380
See application file for complete search history.

(56) References Cited

U.S. PATENT DOCUMENTS

| 4,150,029 A | 4/1979 | Dostert et al. |
|---|---|---|
| 4,287,351 A | 9/1981 | Bourgery et al. |
| 4,340,606 A | 7/1982 | Fugitt et al. |
| 4,372,967 A | 2/1983 | Langlois et al. |
| 4,476,136 A | 10/1984 | Dostert et al. |
| 4,705,799 A | 11/1987 | Gregory |
| 4,851,423 A | 7/1989 | Girijavallabhan et al. |
| 4,942,183 A | 7/1990 | Gregory et al. |
| 4,948,801 A | 8/1990 | Carlson et al. |
| 4,977,173 A | 12/1990 | Brittelli et al. |
| 5,164,510 A | 11/1992 | Brickner |
| 5,182,403 A | 1/1993 | Brickner |
| 5,225,565 A | 7/1993 | Brickner |
| 5,231,188 A | 7/1993 | Brickner |
| 5,247,090 A | 9/1993 | Brickner |
| 5,272,167 A | 12/1993 | Girijavallabhan et al. |
| 5,459,144 A | 10/1995 | Girijavallabhan et al. |
| 5,480,899 A | 1/1996 | Yano et al. |
| 5,521,202 A | 5/1996 | Yano et al. |
| 5,523,403 A | 6/1996 | Barbachyn |
| 5,529,998 A | 6/1996 | Habich et al. |
| 5,532,255 A | 7/1996 | Raddatz et al. |
| 5,547,950 A | 8/1996 | Hutchinson et al. |
| 5,561,148 A | 10/1996 | Gante et al. |

(Continued)

FOREIGN PATENT DOCUMENTS

DE 19901306 7/2000

(Continued)

OTHER PUBLICATIONS

The 1995-2001 ICAAC (Interscience Congress of Antimicrobial Agents and Chemotherapy) conference abstracts.

(Continued)

*Primary Examiner*—Richard Raymond
*Assistant Examiner*—Paul V. Ward

(57) ABSTRACT

Compounds of formula (I), or a pharmaceutically-acceptable salt, or an in-vivo-hydrolysable ester thereof, wherein, for example, X is O, S or NH; HET is an optionally substituted C-linked 5-membered heteroaryl ring containing 2 to 4 heteroatoms independently selected from N, O and S; Q is selected from, for example, Q1 and Q2: $R^2$ and $R^3$ are independently hydrogen or fluoro; T is selected from a range of groups, for example, an N-linked (fully unsaturated) 5-membered heteroaryl ring system or a group of formula (TC5): wherein Rc is, for example, $R^{13}CO$—, $R^{13}SO^2$— or $R^{13}CS$—; wherein $R^{13}$ is, for example, optionally substituted (1–10C)alkyl or $R^{14}C(O)O(1$–6C)alkyl wherein $R^{14}$ is optionally substituted (1–10C)alkyl; are useful as antibacterial agents; and processes for their manufacture and pharmaceutical compositions containing them are described

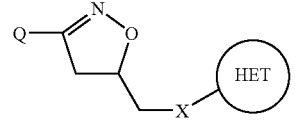

(I)

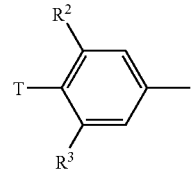

(Q1)

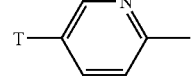

(Q2)

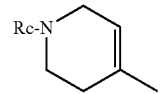

(TC5)

9 Claims, No Drawings

U.S. PATENT DOCUMENTS

| | | |
|---|---|---|
| 5,574,055 A | 11/1996 | Borgulya et al. |
| 5,627,181 A | 5/1997 | Riedl et al. |
| 5,652,238 A | 7/1997 | Brickner et al. |
| 5,668,286 A | 9/1997 | Yamada et al. |
| 5,684,023 A | 11/1997 | Riedl et al. |
| 5,688,792 A | 11/1997 | Barbachyn et al. |
| 5,698,574 A | 12/1997 | Riedl et al. |
| 5,700,799 A | 12/1997 | Hutchinson et al. |
| 5,708,169 A | 1/1998 | Hester, Jr. et al. |
| 5,719,154 A | 2/1998 | Tucker et al. |
| 5,736,545 A | 4/1998 | Gante et al. |
| 5,750,532 A | 5/1998 | Girijavallabhan et al. |
| 5,785,976 A | 7/1998 | Westesen et al. |
| 5,792,765 A | 8/1998 | Riedl et al. |
| 5,827,857 A | 10/1998 | Riedl et al. |
| 5,837,870 A | 11/1998 | Pearlman et al. |
| 5,843,967 A | 12/1998 | Riedl et al. |
| 5,861,413 A | 1/1999 | Habich et al. |
| 5,869,659 A | 2/1999 | Stolle et al. |
| 5,880,118 A | 3/1999 | Barbachyn et al. |
| 5,883,093 A | 3/1999 | Hutchinson et al. |
| 5,910,504 A | 6/1999 | Hutchinson |
| 5,922,708 A | 7/1999 | Riedl et al. |
| 5,929,083 A | 7/1999 | Yoon et al. |
| 5,952,324 A | 9/1999 | Barbachyn et al. |
| 5,955,460 A | 9/1999 | Thomas |
| 5,968,962 A | 10/1999 | Thomas et al. |
| 5,981,528 A | 11/1999 | Gravestock |
| 6,028,090 A | 2/2000 | Gante et al. |
| 6,051,716 A | 4/2000 | Hutchinson et al. |
| 6,069,145 A | 5/2000 | Betts |
| 6,069,160 A | 5/2000 | Stolle et al. |
| 6,090,820 A | 7/2000 | Barbachyn et al. |
| 6,107,519 A | 8/2000 | Pearlman |
| 6,110,936 A | 8/2000 | Gravestock |
| 6,124,334 A | 9/2000 | Hutchinson |
| 6,129,940 A | 10/2000 | Leadbeater |
| 6,140,318 A | 10/2000 | Cama et al. |
| 6,194,441 B1 | 2/2001 | Roberts et al. |
| 6,271,388 B1 | 8/2001 | Yaegashi et al. |
| 6,362,191 B1 | 3/2002 | Mills |
| 6,455,529 B1 | 9/2002 | Gante et al. |
| 6,462,056 B1 | 10/2002 | Bottcher et al. |
| 2002/0045625 A1 | 4/2002 | Sciotti et al. |
| 2002/0103186 A1 | 8/2002 | Mehta et al. |

FOREIGN PATENT DOCUMENTS

| | | |
|---|---|---|
| DE | 19907701 | 8/2000 |
| DE | 19909785 | 9/2000 |
| DE | 10014961 | 1/2001 |
| DE | 10034624 | 1/2002 |
| DE | 10034625 | 1/2002 |
| EP | 127902 | 12/1984 |
| EP | 184170 | 6/1986 |
| EP | 359418 | 8/1989 |
| EP | 609905 | 8/1994 |
| EP | 710657 | 5/1996 |
| EP | 1 029 854 | 8/2000 |
| EP | 1130016 | 9/2001 |
| FR | 2338268 | 8/1977 |
| FR | 2458547 | 1/1981 |
| JP | 7-309850 | 11/1995 |
| JP | 11-322729 | 11/1999 |
| JP | 2000-136186 | 5/2000 |
| WO | WO 93/09103 | 5/1993 |
| WO | WO 93/23384 | 11/1993 |
| WO | WO 94/01110 | 1/1994 |
| WO | WO 97/06791 | 2/1997 |
| WO | WO 97/10223 | 3/1997 |
| WO | WO 97/14690 | 4/1997 |
| WO | WO 97/23212 | * 7/1997 |
| WO | WO 97/31917 | 9/1997 |
| WO | WO 98/01446 | 1/1998 |
| WO | WO 98/01447 | 1/1998 |
| WO | WO 98/07708 | 2/1998 |
| WO | WO 98/54161 | 12/1998 |
| WO | WO 99/02525 | 1/1999 |
| WO | WO 99/03846 | 1/1999 |
| WO | WO 99/10342 | 3/1999 |
| WO | WO 99/12914 | 3/1999 |
| WO | WO 99/24428 | 5/1999 |
| WO | WO 99/25344 | 5/1999 |
| WO | WO 99/29688 | 6/1999 |
| WO | WO 99/32175 | 7/1999 |
| WO | WO 99/33839 | 7/1999 |
| WO | WO 99/37630 | 7/1999 |
| WO | WO 99/37641 | 7/1999 |
| WO | WO 99/37652 | 7/1999 |
| WO | WO 99/40094 | 8/1999 |
| WO | WO 99/41244 | 8/1999 |
| WO | WO 99/43671 | 9/1999 |
| WO | WO 99/59616 | 11/1999 |
| WO | WO 99/62504 | 12/1999 |
| WO | WO 99/63937 | 12/1999 |
| WO | WO 99/64416 | 12/1999 |
| WO | WO 99/64417 | 12/1999 |
| WO | WO 00/03710 | 1/2000 |
| WO | WO 00/10566 | 3/2000 |
| WO | WO 00/21960 | 4/2000 |
| WO | WO 00/27816 | 5/2000 |
| WO | WO 00/27817 | 5/2000 |
| WO | WO 00/27827 | 5/2000 |
| WO | WO 00/29396 | 5/2000 |
| WO | WO 00/29409 | 5/2000 |
| WO | WO 00/32599 | 6/2000 |
| WO | WO 00/41473 | 7/2000 |
| WO | WO 00/44741 | 8/2000 |
| WO | WO 00/45177 | 8/2000 |
| WO | WO 00/62783 | 10/2000 |
| WO | WO 00/73301 | 12/2000 |
| WO | WO 01/40222 | 6/2001 |
| WO | WO 01/40236 | 6/2001 |
| WO | WO 01/42229 | 6/2001 |
| WO | WO 01/42242 | 6/2001 |
| WO | WO 01/44212 | 6/2001 |
| WO | WO 01/46164 | 6/2001 |
| WO | WO 01/46185 | 6/2001 |
| WO | WO 01/47919 | 7/2001 |
| WO | WO 01/58885 | 8/2001 |
| WO | WO 01/74812 | 10/2001 |
| WO | WO 01/80841 | 11/2001 |
| WO | WO 01/81350 | 11/2001 |
| WO | WO 01/94342 | 12/2001 |
| WO | WO 01/98297 | 12/2001 |
| WO | WO 02/02095 | 1/2002 |
| WO | WO 02/15940 | 2/2002 |
| WO | WO 02/18354 | 3/2002 |
| WO | WO 02/20515 | 3/2002 |
| WO | WO 02/32459 | 4/2002 |
| WO | WO 02/32857 | 4/2002 |
| WO | WO 02/48139 | 6/2002 |
| WO | WO 02/050061 | 6/2002 |
| WO | WO 20/50040 | 6/2002 |
| WO | WO 02/051819 | 7/2002 |
| WO | WO 02/059115 | 8/2002 |
| WO | WO 02/059116 | 8/2002 |

OTHER PUBLICATIONS

Ashtekar, D. et al. Oxazolidinones, a New Class of Synthetic Antituberculosis Agent: In vitro and in vivo Activities of Dup-721 Against *Mycobacterium tuberculosis*. *Diagn. Microbiol. Infect. Dis.* 14, 465-471 (1991).

Barbachyn, M. et al. Identification of a Novel Oxazolidinone (U-100480) with Potent Antimycobacterial Activity. *J. Med. Chem.* 39, 680-685 (1996).

Barbachyn, M. et al., Synthesis and Antibacterial Activity of New Tropone-Substituted Phenyloxazolidinone Antibacterial Agents. 1. Identification of Leads and Importance of the Tropone Substitution Pattern. *Bioorganic and Medical Chem. Letters* 6, 1003-1008 (1996).

Barbachyn, M. et al. Synthesis and Antibacterial Activity of New Tropone-Substituted Phenyloxazolidinone Antibacterial Agents. 2. Modification of the Phenyl Ring—the Potentiating Effect of Fluorine Substitution on In Vivo Activity. *Bioorganic and Medicinal Chem. Letters* 6, 1009-1014 (1996).

Barry, A. et al. In Vitro Evaluation of Dup 105 and Dup 721, Two New Oxazolidinone Antimicrobial Agents. *Antimicrobial Agents and Chemotherapy* 32, 150-152 (1988).

Borthwick, A. et al. 5-(Acelamidomethyl)-3-Aryldihydrofuran-2-ones, and 5-(Acetamidomethyl)-3-Aryltetrahydrofuran-2-ones, Two New Classes of Antibacterial Agents. *Med. Chem. Res.* 6, 22-27 (1996).

Brickner, S. et al. Oxazolidinone Antibacterial Agents. *Current Pharmaceutical Design* 2, 175-194 (1996).

Brickner, S. et al. Synthesis and Antibacterial Activity of U-100592 and U-100766, Two Oxazolidinone Antibacterial Agents for the Potential Treatment of Multidrug-Resistant Gram-Positive Bacterial Infections. *J. Med. Chem.* 39, 673-679 (1996).

Bronson, J.J. and Barrett, J.F. Recent Developments in Antibacterial Research. In Ann. Reports Med. Chem. 26, Section III, Chapter 9, pp. 89-98 (2001).

Brumfitt, W. et al. In-vitro Microbiological Activities of Dup 105 and Dup 721, Novel Synthetic Oxazolidinones. *J. Antimicrobial Chemotherapy* 21, 711-720 (1988).

Brumfitt, W. et al. Variation in Response of Gram-Positive cocci to the Combination Dup 721 and ciprofloxacin. *J. Antimicrob. Chemotherapy* 24, 465-466 (1989).

Brumfitt, W. et al. Antibacterial Oxazolidinones: In Vitro Activity of a New Analogue, E33709. *Diagn. Microbiol. Infect. Dis.* 15, 621-625 (1992).

Clemett, D. and Markham, A. Linezolid. Drugs 59, 815-827 (2000).

Dely, J. et al. Activity and Mechanism of Action of Dup 105 and Dup 721, New Oxazolidinone Compounds. *J. Antimicrobial Chemotherapy* 21, 721-730 (1988).

Denis, A. et al. 5-Aryl-beta, gamma Butenolide, A New Class of Antibacterial Derived from the N-Aryl Oxazolidinone Dup 721. *Bioorganic and Med. Chem. Letters* 4, 1925-1930 (1994).

Diekama, D.J. and Jones, R.N. Oxazolidinones. Drugs 59, 7-16 (2000).

Dostert, P. et al. Structural Modifications in Oxazolidinone Series Leading to Type A or B Selective Monoamine Oxidase Inhibitors. *Int. Congress Series, Excerpta Medica* 564, 197-208 (1982).

Eliopoulos, G. et al. In Vitro Activities of New Oxazolidinone Antimicrobial Agents against Enterococci. *Antimicrobial Agents and Chemotherapy* 3240, 1745-1747 (1996).

Eustice, D. et al. The Mechanism of Action of Dup 721, a New Antibacterial Agent: Effects on Macromolecular Synthesis. *Biochem. And Biophys. Res. Comm.* 150, 965-971 (1988).

Eustice, D. et al. Mechanism of Action of Dup 721: Inhibition of an Early Event During Initiation of Protein Synthesis. *Antimicrobial Agents and Chemotherapy* 32, 1218-1222 (1988).

Eustice, D. et al. An Automated Pulse Labeling Method for Structure-Activity Relationship Studies with Antibacterial Oxazolidinones. *Drugs Exp. Clin. Res.* 16, 149-155 (1990).

Ford, C. et al. In Vivo Activities of U-100592 and U-100766, Novel Oxazolidinone Antimicrobial Agents, against Experimental Bacterial Infections. *Antimicrobial Agents and Chemotherapy* 40, 1508-1513 (1996).

Gadwood, R.C. and Shinabarger, D.A. Progress in the Oxazolidinone Antibacterials. Ann. Report Med. Chem. 35, 135-144 (2000).

Grega, K. et al. REgioselective Metalation of Fluoroanilines. An Application to the Synthesis of Fluorinated Oxazolidinone Antibacterial AGents. *J. Org. Chem.* 60, 5255-5261 (1995).

Gregory, W. et al. Antibacterials. Synthesis and Structure-Activity Studies of 3-Aryl-2-Oxazolidinones. 1. The "B" Group. *J. Med. Chem.* 32, 1673-1681 (1989).

Gregory, W. et al. Antibacterials. Synthesis and Structure-Activity Studies of 3-Aryl-2-oxooxazolidines. 2. The "A" Group. *J. Med. Chem.* 33, 2569-2578 (1990).

Hutchinson, D. et al. Piperazinyl Oxazolidinones: Structure Activity Relationship of a New Class of Oxazolidinone Antibacterial Agents. *Interscience Congress of Antimicrobial Agents and Chemotherapy* Abstract 8-14 (Sep. 1995).

Jegham, S. & George, P. Monoamine oxidase A and B inhibitors. Exp. Opin. Ther. Patents 8, 1143-1150 (1998).

Jones, R. et al. In Vitro Antimicrobial Activities and Spectra of U-100592 and U-100766, Two Novel Fluorinated Oxazolidinones. *Antimicrobial Agents and Chemotherapy* 40, 720-726 (1996).

Jorgensen, J. et al. In Vitro Activities of the Oxazolidinone Antibodies U-100592 and U-100766 against *Staphylococcus aureus* and Coagulase-Negative *Staphylococcus* Species. *Antimicrobial Agents and Chemotherapy* 41, 465-467 (Feb. 1997).

Kaatz, G. et al. In Vitro Activities of Oxazolidinone Compounds U100592 and U100766 against *Staphylococcus aureua* and *Staphylococcus epidermis*. *Antimicrobial Agents and Chemotherapy* 40, 799-801 (1996).

Kalgutkar, A.S. et al. Interactions of Nitrogen-Containing Xenobiotics with Monoamine Oxidase (MAO) Isozymes A and B: SAR Studies on MAO Substrates and Inhibitors. Chemical. Res. in Toxicology 14, Section 10.2, p. 1149 (2001).

Lin, A. et al. The Oxazolidinone Eperezplid Binds to the 50S Ribosomal Subunit and Competes with Binding of Chloramphenical and Lincomycin. *Antimicrobial Agents and Chemotherapy* 41, 2127-2131 (1997).

Lizondo, J. et al. Linezolid U-100766. *Drugs of the Future* 21, 1116-1123 (1996).

Lund, J. et al. Hypersegmented Megakaryocytes and Megakaryocytes with Multiple Separate Nuclei in Dogs Treated with PNU-100592, an Oxazolidinone Antibiotic. *Taxicologic Pathology* 25, 339-343 (1997).

Maple, P. et al. Comparative in-vitro activity of vancomycin, teicoplanin, ramoplanin (formerly A16686), paldimycin, Dup 721 and Dup 105 against methicillin and gentamicin resistant *Staphylococcus aureus*. *J. Antimicrobial Chemotherapy* 23, 517-525 (1989).

Mason, E. et al. In Vitro Activities of Oxazolidinones U-100592 and U-100766 against Penicillin-Resistant and Cephalosporin-Resistant Strains of Streptococcus

*pneumoniae. Antimicrobial Agents and Chemotherapy* 40, 1039-1040 (1996).

Mini, E. et al. Comparative in Vitro Activity of the New Oxazolidinones Dup 721 and Dup 105 against *Staphylococci* and *Streptococci*. *Eur. J. Clin. Microbiol. Infect. Dis.* 8, 256-260 (1989).

Mulazimoglu, L. et al. In Vitro Activities of Two Novel Oxazolidinones (U100592 and U100766), a New Fluoroquinolone (Trovafloxacin), and Dalfopristin-Quinupristin against *Staphylococcus aureus* and *Staphylococcus epidermis*. *Antimicrobial Agents and Chemotherapy* 40, 2428-2430 (1996).

Neu, H. et al. In Vitro Activities of Two Oxazolidinone Antimicrobial Agnets, Dup 721 and Dup 105. *Antimicrobial Agents and Chemotherapy* 32, 580-583 (1988).

Park, C. et al. Antibacterials, Synthesis and Structure-Activity Studies of 3-Aryl-2- Oxazolidinones. 4. Multiply-Substituted Aryl Derivatives. *J. Med. Chem.* 35, 1156-1165 (1992).

Patel, U. et al. Oxazolidinones Mechanism of Action: Inhibition of the First Peptide Bond Formation. J. Biol. Chem. 276, 37199-37205 (Oct. 05, 2001).

Ranaldi, G. et al. Transport of the Antibacterial Agent Oxazolidin-2-One and Derivatives across Intestinal (Caco-2) and Renal (MDCK) Epithelial Cell Lines. *Antimicrobial Agents and Chemotherapy* 40, 652-658 (1996).

Riedl, B. & Endermann, R. Recent developments with oxazolidinone antibiotics. Exp. Opin. Ther. Patents 9, 625-633 (1999).

Schaadt, R. et al. Serum Inhibitory Titers and Serum Bactericidal Titers for Human Subjects Receiving Multiple Doses of the Antibacterial Oxazolidinones Eperezolid and Linezolid. *Diagn. Microbiol. Infect. Dis.* 28, 201-204 (1997).

Schaus, S. et al. Dynamic Kinetic Resolution of Epichlorohydrin via Enantioselective Catalytic Ring Operation with TMSN3. Practical Synthesis of Aryl Oxazolidinone Antibacterial Agents. *Tetrahedron Letters* 37, 7937-7940 (1996).

Scholl, J. et al. Micellar Electrokinetic Chromatography as a Generalized Alternative to High-Performance Liquid Chromatography for Purity Determination of a Class of Investigational Antibacterial Drugs. *J. Chromatography* 695, 147-156 (1997).

Seneci, P. et al. Synthesis and Antimicrobial Activity of Oxazolidin-2-ones and Related Heterocycles. *J. Chem. Soc. Perkin Trans.* 1, 16, 2345-2351 (1994).

Shinabarger, D. et al. Mechanism of Action of Oxazolidinones: Effects of Linezolid and Eperezolid on Translatio Reactions. *Antimicrobial Agent and Chemotherapy* 41, 2132-2136 (1997).

Silverman, R. et al. The Oxazolidinone Antibacterial Agent DuP 105 Does Not Act on Cell Wall Biosynthesis or on a Beta-Lactamase, *Biochemical and Biophys. Res. Comm.* 1995, 1077-1080 (1993).

Slee, A. et al. Oxazolidinones, a New Class of Synthetic Antibacterial Agents: In Vitro and In Vivo Activities of DuP 105 and DuP 721. *Antimicrobial Agents and Chemotherapy* 31, 1791-1797 (1987).

Spangler, S. et al. Activities of RPR 106972 (a New Oral Streptogramin), Cefditoren (a New Oral Cephalosporin), Two New Oxazolidinones (U-100592 and U-100766), and Other Oral and Parenteral Agents against 203 Penicillin-Susceptible and-Resistant Pneumococci. *Antimicrobial Agents and chemotherapy* 40, 481-484 (1996).

Takagi, H. et al. Safety Pharmacology Evaluation of the Oxazolidinone, U-100766. *Society of Taxicologists Annual Meeting*—Abstract 110, (1996).

Tucker, J. A. et al. Piperazinyl Oxazolidinone Antibacterial Agents Containing a Pyridine, Diazene, or Triazene Heteroaromatic Ring. *J. Med. Chem.* 41, 3727-2735 (1998).

Wang, C. et al. Chiral Synthesis fo DuP 721, a New Antibacterial Agent. *Tetrahedron* 45, 1323-1326 (1989).

Worth, S. et al. Quality Control Guidelines for Amoxicillin, Amoxicillin-Clavulanate, Azithromycin, Piperacillin-Tazobactam, Roxithromycin, Ticarcillin-Clavulanate, Trovafloxacin (CP 99,219), U-100592, and U-100766 for Various National Committee . . . *Diagn. Microbiol. Infect. Dis.* 24, 87-91 (1996).

Zurenko, G. et al. In Vitro Activities of U-100592 and U-100766, Novel Oxazolidinone Antibacterial Agents. *Antimicrobial Agents and Chemotherapy* 40, 839-845 (1996).

Zuernko, G. et al. Oxazolidinone antibacterial agents: Development of the Clinical Candidates Eperezolid and Linezolid. *Exp. Opin. Invest. Drugs* 6, 151-158 (1997).

* cited by examiner

SUBSTITUTED ISOXAZOLINES AND THEIR USE AS ANTIBACTERIAL AGENTS

RELATED APPLICATIONS

This application is a national stage filing under 35 U.S.C. 371 of PCT application PCT/GB00/04516, filed Nov. 28, 2000, which claims priority from Great Britain Application No. 9928568.6, filed Dec. 3, 1999, the specifications of each of which are incorporated by reference herein.

The present invention relates to antibiotic compounds and in particular to antibiotic compounds containing a substituted isoxazoline ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant *staphylococcus* (MRSA), methicillin resistant coagulase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

Certain antibacterial compounds containing an oxazolidinone ring have been described in the art (for example, Walter A. Gregory et al in J. Med. Chem. 1990, 33, 2569–2578 and Chung-Ho Park et al in J. Med. Chem. 1992, 35, 1156–1165). Such antibacterial oxazolidinone compounds with a 5-methylacetamide sidechain may be subject to mammalian peptidase metabolism. Furthermore, bacterial resistance to known antibacterial agents may develop, for example, by (i) the evolution of active binding sites in the bacteria rendering a previously active pharmacophore less effective or redundant, and/or (ii) the evolution of means to chemically deactivate a given pharmacophore. Therefore, there remains an ongoing need to find new antibacterial agents with a favourable pharmacological profile, in particular for compounds containing new pharmacophores.

We have discovered a class of antibiotic compounds containing a new class of substituted isoxazoline (4,5-dihydro-isoxazole) ring which has useful activity against Gram-positive pathogens including MRSA and MRCNS and, in particular, against various strains exhibiting resistance to vancomycin and against *E. faecium* strains resistant to both aminoglycosides and clinically used β-lactams.

Accordingly the present invention provides a compound of the formula (I), or a pharmaceutically-acceptable salt, or an in-vivo-hydrolysable ester thereof,

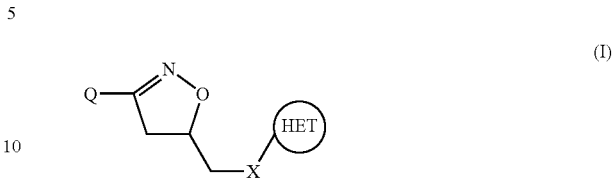

wherein

X is O, NH, S, SO or $SO_2$.

HET is a C-linked 5-membered heteroaryl ring containing 2 to 4 heteroatoms independently selected from N, O and S, which ring is optionally substituted on an available carbon atom by 1 or 2 substituents independently selected from (1–4C)alkyl, amino, (1–4C)alkylamino, (1–4C)alkoxy, (1–4C)alkoxycarbonyl and halogen, and/or on an available nitrogen atom (provided that the ring is not thereby quaternised) by (1–4C)alkyl; or HET is a C-linked 6-membered heteroaryl ring containing 2 or 3 nitrogen heteroatoms, which ring is optionally substituted on any available C atom by 1, 2 or 3 substituents independently selected from (1–4C)alkyl, amino, (1–4C) alkylamino, (1–4C)alkoxy, (1–4C)alkoxycarbonyl and halogen;

Q is selected from Q1 to Q9:—

-continued

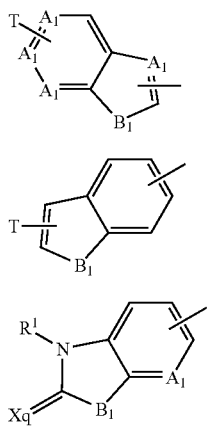

wherein $R^2$ and $R^3$ are independently hydrogen or fluoro;

wherein $A_1$ is carbon or nitrogen; $B_1$ is O or S (or, in Q9 only, NH); $X_q$ is O, S or N—$R^1$ (wherein $R^1$ is hydrogen, (1–4C)alkyl or hydroxy-(1–4C)alkyl); and wherein in Q7 each $A_1$ is independently selected from carbon or nitrogen, with a maximum of 2 nitrogen heteroatoms in the 6-membered ring, and Q7 is linked to T via any of the $A_1$ atoms (when $A_1$ is carbon), and linked in the 5-membered ring via the specified carbon atom, or via $A_1$ when $A_1$ is carbon; Q8 is linked to T via either of the specified carbon atoms in the 5-membered ring, and linked in the benzo-ring via either of the two specified carbon atoms on either side of the linking bond shown; and Q9 is linked via either of the two specified carbon atoms on either side of the linking bond shown;

wherein T is selected from the groups in (TA) to (TD) below (wherein AR1, AR2, AR2a, AR2b, AR3, AR3a, AR3b, AR4, AR4a, CY1 and CY2 are defined hereinbelow);

(TA) T is selected from the following groups :—

(TAa) AR1, AR1-(1–4C)alkyl-, AR2 (carbon linked), AR3;

(TAb) AR1-CH(OH), AR2-CH(OH)—, AR3-CH(OH)—;

(TAc) AR1-CO—, AR2-CO—, AR3-CO—, AR4-CO—;

(TAd) AR1-O—, AR2-O—, AR3-O—;

(TAe) AR1-S(O)$_q$—, AR2-S(O)$_q$—, AR3-S(O)$_q$— (q is 0, 1 or 2);

(TAf) an optionally substituted N-linked (fully unsaturated) 5-membered heteroaryl ring system containing 1, 2 or 3 nitrogen atoms;

(TAg) a carbon linked tropol-3-one or tropol-4-one, optionally substituted in a position not adjacent to the linking position; or (TB) T is selected from the following groups:—

(TBa) halo or (1–4C)alkyl

{optionally substituted by one or more groups each independently selected from hydroxy, (1–4C)alkoxy, (1–4C)alkanoyl, cyano, halo, trifluoromethyl, (1–4C)alkoxycarbonyl, —NRvRw, (1–6C)alkanoylamino, (1–4C)alkoxycarbonylamino, N-(1–4C)alkyl-N-(1–6C)alkanoylamino, (1–4C)alkylS(O)$_q$— (q is 0, 1 or 2), CY1, CY2 or AR1 };

(TBb) -NRv$^1$Rw$^1$;

(TBc) ethenyl, 2-(1–4C)alkylethenyl, 2-cyanoethenyl, 2-cyano-2-((14C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl;

(TBd) $R^{10}$CO—, $R^{10}$S(O)$_q$— (q is 0, 1 or 2) or $R^{10}$CS— wherein $R^{10}$ is selected from the following groups :—

(TBda) CY1 or CY2;

(TBdb) hydrogen, (1–4C)alkoxycarbonyl, trifluoromethyl, —NRvRw, ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl or 2-(AR2)ethenyl; or (TBdc) (1–4C)alkyl {optionally substituted as defined in (TBa) above, or by (1–4C)alkylS(O)$_p$NH— or (1–4C)alkylS(O)$_p$— ((1–4C)alkyl)N— (p is 1 or 2)};

wherein Rv is hydrogen or (1–4C)alkyl; Rw is hydrogen or (1–4C)alkyl; Rv$^1$ is hydrogen, (1–4C)alkyl or (3–8C)cycloalkyl; Rw$^1$ is hydrogen, (1–4C)alkyl, (3–8C)cycloalkyl, (14C)alkyl- CO— or (1–4C)alkylS(O)$_q$— (q is 1 or 2); or (TC) T is selected from the following groups (TCa) an optionally substituted, filly saturated 4-membered monocyclic ring containing 1 heteroatom selected from O, N and S (optionally oxidised), and linked via a ring nitrogen or sp$^3$ carbon atom;

(TCb) an optionally substituted 5-membered monocyclic ring containing 1 heteroatom selected from O, N and S (optionally oxidised), and linked via a ring nitrogen atom or a ring sp$^3$ or sp$^2$ carbon atom, which monocyclic ring is fully saturated other than (where appropriate) at a linking sp$^2$ carbon atom;

(TCc) an optionally substituted 6- or 7-membered monocyclic ring containing 1 or 2 heteroatoms independently selected from O, N and S (optionally oxidised), and linked via a ring nitrogen atom or a ring sp$^3$ or sp$^2$ carbon atom, which monocyclic ring is fully saturated other than (where appropriate) at a linking sp$^2$ carbon atom; or (TD) T is selected from the following groups :—

(TDa) a bicyclic spiro-ring system containing 0, 1 or 2 ring nitrogen atoms as the only ring heteroatoms, the structure consisting of a 5- or 6-membered ring system (linked via a ring nitrogen atom or a ring sp$^3$ or sp$^2$ carbon atom) substituted (but not adjacent to the linking position) by a 3-, 4- or 5-membered spiro-carbon-linked ring; which bicyclic ring system is (i) fully saturated other than (where appropriate) at a linking sp$^2$ carbon atom;

(ii) contains one —N(Rc)— group in the ring system (at least two carbon atoms away from the linking position when the link is via a nitrogen atom or an sp$^2$ carbon atom) or one —N(Rc)— group in an optional substituent (not adjacent to the linking position) and is (iii) optionally further substituted on an available ring carbon atom; or (TDb) a 7-, 8- or 9-membered bicyclic ring system (linked via a ring nitrogen atom or a ring sp³ or sp² carbon atom) containing 0, 1 or 2 ring nitrogen atoms (and optionally a further O or S ring heteroatom), the structure containing a bridge of 1, 2 or 3 carbon atoms; which bicyclic ring system is (i) fully saturated other than (where appropriate) at a linking sp² carbon atom;

(ii) contains one O or S heteroatom, or one —N(Rc)— group in the ring (at least two carbon atoms away from the linking position when the link is via a nitrogen atom or an sp² carbon atom) or one —N(Rc)— group in an optional substituent (not adjacent to the linking position) and is (iii) optionally further substituted on an available ring carbon atom;

wherein Rc is selected from groups (Rc1) to (Rc5):—

(Rc1) (1–6C)alkyl {optionally substituted by one or more (1–4C)alkanoyl groups (including geminal disubstitution) and/or optionally monosubstituted by cyano, (1–4C)alkoxy, trifluoromethyl, (1–4C)alkoxycarbonyl, phenyl (optionally substituted as for AR defined hereinafter), (1–4C)alkylS(O)$_q$— (q is 0, 1 or 2); or, on any but the first carbon atom of the (1–6C)alkyl chain, optionally substituted by one or more groups (including geminal disubstitution) each independently selected from hydroxy and fluoro, and/or optionally monosubstituted by oxo, —NRvRw [wherein Rv is hydrogen or (1–4C)alkyl; Rw is hydrogen or (1–4C)alkyl], (1–6C)alkanoylamino, (1–4C)alkoxycarbonylamino, N-(1–4C)alkyl-N-(1–6C)alkanoylamino, (1–4C)alkylS(O)$_p$NH— or (1–4C)alkylS(O)$_p$—((1–4C)alkyl)N—(p is 1 or 2)}; (Rc2) R$^{13}$CO—, R$^{13}$SO$_2$— or R$^{13}$CS— wherein R$^{13}$ is selected from (Rc2a) to (Rc2e):—

(Rc2a) AR1, AR2, AR2a, AR2b, AR3, AR3a, AR3b, AR4, AR4a, CY1, CY2;

(Rc2b) hydrogen, (1–4C)alkoxycarbonyl, trifluoromethyl, —NRvRw [wherein Rv is hydrogen or (1–4C)alkyl; Rw is hydrogen or (1–4C)alkyl], ethenyl, 2-(14C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl, 2-(AR2a)ethenyl;

(Rc2c) (1–10C)alkyl

{optionally substituted by one or more groups (including geminal disubstitution) each independently selected from hydroxy, (1–10C)alkoxy, (1–4C)alkoxy-(1 4C)alkoxy, (1–4C)alkoxy-(1–4C)alkoxy-(1–4C)alkoxy, (1–4C)alkanoyl, phosphoryl [—O—P(O)(OH)$_2$, and mono- and di-(1–4C)alkoxy derivatives thereof], phosphiryl [—O—P(OH)$_2$ and mono- and di-(1–4C)alkoxy derivatives thereof], and amino; and/or optionally substituted by one group selected from phosphonate [phosphono, —P(O)(OH)$_2$, and mono- and di-(1–4C)alkoxy derivatives thereof], phosphinate [—P(OH)$_2$ and mono- and di-(1–4C)alkoxy derivatives thereof], cyano, halo, trifluoromethyl, (1–4C)alkoxycarbonyl, (1–4C)alkoxy-(1–4C)alkoxycarbonyl, (I 4C)alkoxy-(1–4C)alkoxy-(1–4C)alkoxycarbonyl, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$—((1–4C)alkyl)N—, fluoro(1–4C)alkylS(O)$_p$NH—, fluoro(1–4C)alkylS(O)$_p$((1–4C)alkyl)N—, (1–4C)alkylS(O)$_q$— [the (1–4C)alkyl group of (1–4C)alkylS(O)$_q$— being optionally substituted by one substituent selected from hydroxy, (1–4C)alkoxy, (1–4C)alkanoyl, phosphoryl [—O—P(O)(OH)$_2$, and mono- and di-(1–4C)alkoxy derivatives thereof], phosphiryl [—O—P(OH)$_2$ and mono- and di-(1–4C)alkoxy derivatives thereof], amino, cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, carboxy, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1 4C)alkyl)aminocarbonyl, (1 C)alkylS(O)$_p$NH—, (1–4C)alkylS(O)$_p$-((1–4C)alkyl)N—, (1–4C)alkylS(O)$_q$—, AR1-S(O)$_q$—, AR2-S(O)$_q$—, AR3-S(O)$_q$— and also AR2a, AR2b, AR3a and AR3b versions of AR2 and AR3 containing groups], CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH- (p is 1 or 2 and q is 0, 1 or 2), and also AR2a, AR2b, AR3a and AR3b versions of AR2 and AR3 containing groups};

(Rc2d) R$^{14}$C(O)O(1–6C)alkyl wherein R$^{14}$ is AR1, AR2, (1–4C)alkylamino (the (1–4C)alkyl group being optionally substituted by (1–4C)alkoxycarbonyl or by carboxy), benzyloxy-(1–4C)alkyl or (1–10C)alkyl (optionally substituted as defined for (Rc2c)}; (Rc2e) R$^{15}$O— wherein R$^{15}$ is benzyl, (1–6C)alkyl {optionally substituted as defined for (Rc2c)}, CY1, CY2 or AR2b;

(Rc3) hydrogen, cyano, 2-cyanoethenyl, 2-cyano-2-((1–4C) alkyl)ethenyl, 2-((1–4C)alkylaminocarbonyl)ethenyl, 2-((1–4C)alkoxycarbonyl)ethenyl, 2-nitroethenyl, 2-nitro-2-((1–4C)alkyl)ethenyl, 2-(AR1)ethenyl, 2-(AR2)ethenyl, or of the formula (Rc3a)

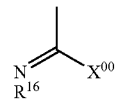

(Rc3a)

wherein X$^{00}$ is —OR$^7$, —SR$^{17}$, —NHR$^{17}$ and —N(R$^{17}$)$_2$;

wherein R$^{17}$ is hydrogen (when X$^{00}$ is —NHR$^{17}$ and —N(R$^{17}$)$_2$), and R$^{17}$ is (1–4C)alkyl, phenyl or AR2 (when X$^{00}$ is —OR$^{17}$, —SR$^{17}$ and —NHR$^{17}$); and R$^{16}$ is cyano, nitro, (1–4C)alkylsulfonyl, (4–7C)cycloalkylsulfonyl, phenylsulfonyl, (1–4C)alkanoyl and (1–4C)alkoxycarbonyl;

(Rc4) trityl, AR1, AR2, AR2a, AR2b, AR3, AR3a, AR3b;

(Rc5) RdOC(Re)=CH(C=O)—, RfC(=O)C(=O)—, RgN=C(Rh)C(=O)— or

RiNHC(Rj)=CHC(=O)— wherein Rd is (1–6C)alkyl; Re is hydrogen or (1–6C)alkyl, or Rd and Re together form a (3–4C)alkylene chain; Rf is hydrogen, (1–6C)alkyl, hydroxy (1–6C)alkyl, (1–6C)alkoxy(1–6C)alkyl, —NRvRw [wherein Rv is hydrogen or (1–4C)alkyl; Rw is hydrogen or (1–4C)alkyl], (1–6C)alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy; Rg is (1–6C)alkyl, hydroxy or (1–6C)alkoxy; Rh is hydrogen or (1–6C)alkyl; Rh is hydrogen, (1–6C)alkyl, AR1, AR2, AR2a, AR2b and Rj is hydrogen or (1–6C)alkyl;

wherein

AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised;

AR2b is a fully hydrogenated version of AR2 (i.e. AR2 systems having no unsaturation), linked via a ring carbon atom or linked via a ring nitrogen atom;

AR3 is an optionally substituted 8-, 9- or 10-membered, fully unsaturated (i.e with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the full, degree of unsaturation), linked via a ring carbon atom, or linked via a ring nitrogen atom if the ring is not thereby quaternised, in any of the rings comprising the tricyclic system;

CY1 is an optionally substituted cyclobutyl, cyclopentyl or cyclohexyl ring;

CY2 is an optionally substituted cyclopentenyl or cyclohexenyl ring.

In this specification, where it is stated that a ring may be linked via an $sp^2$ carbon atom, which ring is fully saturated other than (where appropriate) at a linking $sp^2$ carbon atom, it is to be understood that the ring is linked via one of the carbon atoms in a C═C double bond.

In another embodiment, (Rc1) is as defined above other than the optional phenyl substituent on (1–6C)alkyl is optionally substituted as for AR1 defined hereinafter; and (Rc2c), is as defined above and further includes carboxy as an optional substituent on $R^{13}$ as (1–10C)alkyl.

(TAf) When T is an optionally substituted N-linked (fully unsaturated) 5-membered heteroaryl ring system containing 1, 2 or 3 nitrogen atoms, it is preferably selected from a group of formula (TAf1) to (TAf6) below (particularly (TAf1), (TAf2), (TAf4) and (TAf5), group of formula (TAf1) to (TAf6) below (particularly (TAf1), (TAf2), (TAf4) and (TAf5), and especially (TAf1) and/or (TAf2)). The above preferred values of (TAf) are particularly preferred when present in Q1 or Q2, especially Q1.

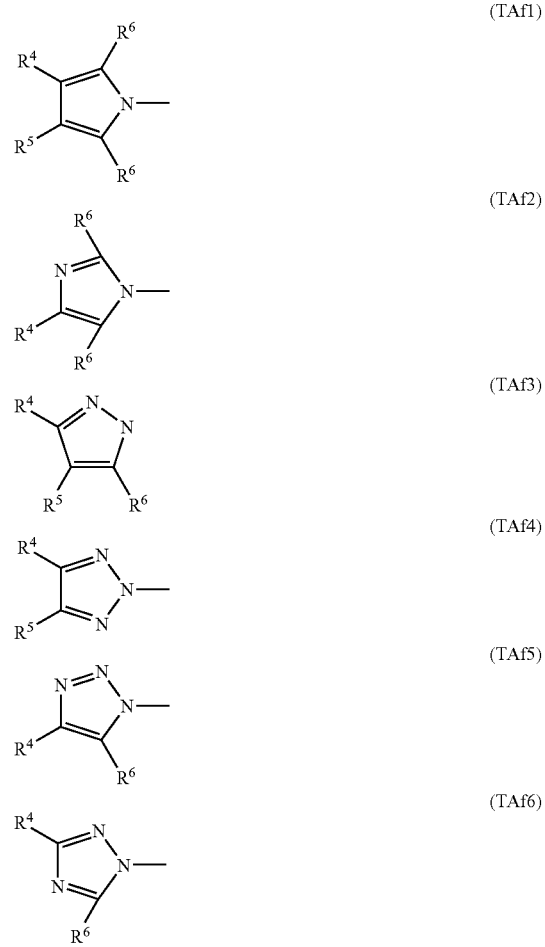

wherein:

$R^6$ is selected (independently where appropriate) from hydrogen, (1–4C)alkyl, (1–4C)alkoxycarbonyl, (1 4C)alkanoyl, carbamoyl and cyano;

$R^4$ and $R^5$ are independently selected from hydrogen, halo, trifluoromethyl, cyano, nitro, (1–4C)alkoxy, (1–4C)alkylS(O)$_q$— (q is 0, 1 or 2), (14C)alkanoyl, (1–4C)alkoxycarbonyl, (2–4C)alkanoyloxy-(1–4C)alkyl, benzoxy-(1–4C)alkyl, (2–4C)alkanoylamino, —CONRvRw, —NRvRw and (1–4C)alkyl {optionally substituted by hydroxy, trifluoromethyl, cyano, nitro, (1 4C)alkoxy, (1–4C)alkylS(O)$_q$— (q is 0, 1 or 2), (1–4C)alkoxycarbonyl, (1–4C)alkanoylamino, —CONRvRw, —NRvRw; wherein RvRw is hydrogen or (1–4C)alkyl; Rw is hydrogen or (1–4C)alkyl};

or $R^4$ is selected from one of the groups in (TAfa) to (TAfc) below, or (where appropriate) one of $R^4$ and $R^5$ is selected from the above list of $R^4$ and $R^5$ values, and the other is selected from one of the groups in (TAfa) to (TAfc) below (TAfa) a group of the formula (TAfa1)

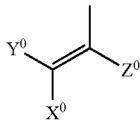

(TAfa1)

wherein Z⁰ is hydrogen or (1–4C)alkyl;

X⁰ and Y⁰ are independently selected from hydrogen, (1–4C)alkyl, (1–4C)alkoxycarbonyl, halo, cyano, nitro, (1–4C)alkylS(O)$_q$— (q is 0, 1 or 2), RvRwNSO$_2$—, trifluoromethyl, pentafluoroethyl, (1–4C)alkanoyl and —CONRvRw [wherein Rv is hydrogen or (1–4C)alkyl; Rw is hydrogen or (1–4C)alkyl]; or one of X⁰ and Y⁰ is selected from the above list of X⁰ and Y⁰ values, and the other is selected from phenyl, phenylcarbonyl, —S(O)$_q$-phenyl (q is 0, 1 or 2), N-(phenyl) carbamoyl, phenylaminosulfonyl, AR2, (AR2)—CO—, (AR2)—S(O)$_q$— (q is 0, 1 or 2), N-(AR2)carbamoyl and (AR2)aminosulfonyl; wherein any phenyl group in (TAfa) may be optionally substituted by up to three substituents independently selected from (1–4C)alkyl, cyano, trifluoromethyl, nitro, halo and (1–4C)alkylsulfonyl;

(TAfb) an acetylene of the formula —≡—H or —≡—(1–4C)alkyl;

(TAfc) —X¹—Y¹-AR2, —X¹—Y¹—AR2a, —X¹—Y¹-AR2b, —X¹—Y¹-AR3, —X¹—Y¹-AR3a or —X¹—Y¹-AR3b;

wherein X¹ is a direct bond or —CH(OH)— and

Y¹ is —(CH$_2$)$_m$—, —(CH$_2$)$_n$—NH—(CH$_2$)$_m$—, —CO—(CH$_2$)$_m$—, —CONH—(CH$_2$)$_m$—, —C(=S)NH—(CH$_2$)$_m$— or —C(=O)O—(CH$_2$)$_m$—;

or wherein X¹ is —(CH$_2$)$_n$— or —CH(Me)—(CH$_2$)$_m$— and

Y¹ is —(CH$_2$)$_m$—NH—(CH$_2$)$_m$—, —CO—(CH$_2$)$_m$—, —CONH—(CH$_2$)$_m$—, —C(=S)NH—(CH$_2$)$_m$—, —C(=O)O—(CH$_2$)$_m$— or —S(O)$_q$—(CH$_2$)$_m$—;

or wherein X¹ is —CH$_2$O—, —CH$_2$NH— or —CH$_2$N((1–4C)alkyl)- and

Y¹ is —CO—(CH$_2$)$_m$—, —CONH—(CH$_2$)$_m$— or —C(=S)NH—(CH$_2$)$_m$—; and additionally Y¹ is —SO$_2$— when X¹ is —CH$_2$NH— or —CH$_2$N((1–4C)alkyl)-, and Y¹ is —(CH$_2$)$_m$— when X¹ is —CH$_2$O— or —CH$_2$N((1–4C)alkyl)-; wherein n is 1, 2 or 3; m is 0, 1, 2 or 3 and q is 0, 1 or 2; and when Y¹ is —(CH$_2$)$_m$—NH—(CH$_2$)$_m$— each m is independently selected from 0, 1, 2 or 3.

It is to be understood that when a value for —X¹— is a two-atom link and is written, for example, as —CH$_2$NH— it is the left hand part (—CH$_2$— here) which is bonded to the group of formula (TAf1) to (TAf6) and the right hand part (—NH— here) which is bonded to —Y¹— in the definition in (TAfc). Similarly, when —Y¹— is a two-atom link and is written, for example, as —CONH— it is the left hand part of —Y¹— (—CO— here) which is bonded to the right hand part of —X¹—, and the right hand part of —Y¹— (—NH— here) which is bonded to the AR2, AR2a, AR2b, AR3, AR3a or AR3b moiety in the definition in (TAfc).

Preferably R⁶ is hydrogen or (1–4C)alkyl, and R⁴ and R⁵ are independently selected from hydrogen, (1–4C)alkyl or one of R⁴ and R⁵ is selected from group (TAfa). Other preferable substituents on the (TAf1) to (TAf6) are illustrated in the accompanying Examples. Most preferable is (TAf2) with such preferable substituents.

(TAg) When T is a carbon linked tropol-3-one or tropol-4-one, optionally substituted in a position not adjacent to the linking position (TAg), it is preferably selected from a group of formula (TAg1), (TAg2) or (TAg3). The above preferred values of (TAg) are particularly preferred when present in Q1 or Q2, especially Q1.

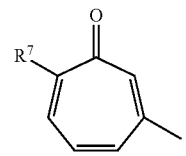

(TAg1)

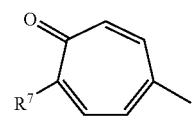

(TAg2)

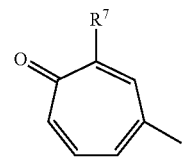

(TAg3)

wherein R⁷ is selected from (TAga) hydrogen, (1–4C)alkyl {optionally substituted by one or two substituents (excluding geminal disubstitution) independently selected from fluoro, hydroxy, (1–4C)alkoxy and —NRvRw]}; or (TAgb) R⁸—O—, R⁸—S—, R⁸—NH— or R⁸R⁸—N—;

wherein R⁸ is selected (independently where appropriate) from hydrogen, (1–4C)alkyl or (3–8C)cycloalkyl {both optionally substituted by one or two substituents (excluding geminal disubstitution) independently selected from hydroxy, (1–4C)alkoxy, (1–4C)alkoxycarbonyl and —NRvRw}, (2–4C)alkenyl (optionally substituted by one or two —NRvRw substituents}, (1–4C)alkanoyl (optionally substituted by one or two substituents independently selected from —NRvRw and hydroxy}, phenyl-(1–4C)alkyl or pyridyl-(1–4C)alkyl (the phenyl and pyridyl (preferably pyridin-4-yl) rings being optionally substituted by one or two —NRvRw substituents}; or (TAgc) morpholino, thiomorpholino, pyrrolidino (optionally independently substituted in the 3- and/or 4-positions by (1–4C)alkyl}, piperidino substituted in the 4-position by R⁹—, R⁹—O—, R⁹—S—, R⁹—NH— or R⁹R⁹—N—; wherein R⁹ is selected (independently where appropriate) from hydrogen, (1–4C)alkyl (optionally substituted by one or two (excluding geminal disubstitution) hydroxy, (1–4C) alkoxy, (1–4C)alkoxycarbonyl or —NRvRw} and piperazino {optionally substituted in the 4-position by (1–4C) alkyl, (3–8C)cycloalkyl, (1–4C)alkanoyl, (1–4C) alkoxycarbonyl or (1–4C)alkylsulfonyl, and optionally independently substituted in the 3- and/or 5-positions by (1–4C)alkyl}; wherein Rv is hydrogen or (1–4C)alkyl; Rw is hydrogen or (1–4C)alkyl.

(TC) Preferred values for the optional substituents and groups defined in (TCa) to (TCc) are defined by formulae (TC1) to (TC4):—

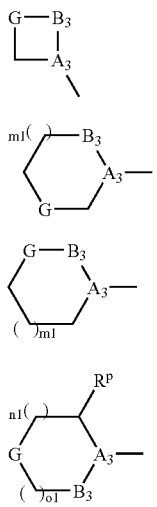

(TC1)

(TC2)

(TC3)

(TC4)

wherein in (TC1): $>A_3-B_3-$ is $>C(Rq)-CH(Rr)-$ and G is $-O-$, $-S-$, $-SO-$, $-SO_2-$ or $>N(Rc)$;

wherein in (TC2): m1 is 0, 1 or 2; $>A_3-B_3-$ is $>C=C(Rr)-$ or $>C(Rq)-CH(Rr)-$ and G is $-O-$, $-S-$, $-SO-$, $-SO_2-$ or $>N(Rc)$;

wherein in (TC3): m1 is 0, 1 or 2; $>A_3-B_3-$ is $>C(Rq)-CH(Rr)-$ (other than when Rq and Rr are both together hydrogen) and G is $-O-$, $-S-$, $-SO-$, $-SO_2-$ or $>N(Rc)$;

wherein in (TC4): n1 is 1 or 2; o1 is 1 or 2 and n1+o1=2 or 3; $>A_3-B_3-$ is $>C=C(Rr)-$ or $>C(Rq)-CH(Rr)-$ or $>N-CH_2-$ and G is $-O-$, $-S-$, $-SO-$, $-SO_2-$ or $>N(Rc)$; Rp is hydrogen, (1–4C)alkyl (other than when such substitution is defined by $>A_3-B_3-$), hydroxy, (1–4C)alkoxy or (1–4C)alkanoyloxy;

wherein in (TC1), (TC2) and (TC4); m1, n1 and o1 are as defined hereinbefore: $>A_3-B_3-$ is $>N-CH_2-$ and G is $>C(R^{11})(R^{12})$, $>C=O$, $>C-OH$, $>C-(1-4C)$alkoxy, $>C=N-OH$, $>C=N-(1-4C)$alkoxy, $>C=N-NH-(1-4C)$alkyl, $>C=N-N((1-4C)$alkyl$)_2$ (the last two (1–4C) alkyl groups above in G being optionally substituted by hydroxy) or $>C=N-N-CO-(1-4C)$alkoxy; wherein > represents two single bonds;

Rq is hydrogen, hydroxy, halo, (1–4C)alkyl or (1–4C) alkanoyloxy;

Rr is (independently where appropriate) hydrogen or (1–4C) alkyl;

$R^{11}$ is hydrogen, (1–4C)alkyl, fluoro(1–4C)alkyl, (1–4C) alkyl-thio-(1–4C)alkyl or hydroxy-(1–4C)alkyl and $R^{12}$ is $-[C(Rr)(Rr)]_{m2}-N(Rr)(Rc)$ wherein m2 is 0, 1 or 2;

and, other than the ring substitution defined by G, $>A_3-B_3-$ and Rp, each ring system may be optionally further substituted on a carbon atom not adjacent to the link at $>A_3-$ by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C) alkanoylamino-(1–4C)alkyl, carboxy, (1–4C)alkoxycarbonyl, AR-oxymethyl, AR-thiomethyl, oxo (=O) (other than when G is $>N-Rc$ and Rc is group (Rc2) defined hereinbefore) or independently selected from Rc; and also hydroxy or halo (the last two optional substituents only when G is $-O-$ or $-S-$);

wherein AR (or ARp) is as defined for formula (IP) hereinafter; Rc is selected from groups (Rc1) to (Rc5) defined hereinbefore.

For the avoidance of doubt, $(\ )_{m1}$, $(\ )_{n1}$ and $(\ )_{o1}$ indicate $(-CH_2-)_{m1}$, $(-CH_2-)_{n1}$ and $(-CH_2-)_{o1}$ respectively (optionally substituted as described above).

In the above definition of (TC1) to (TC4) and of the further optional substituents, AR is preferably AR2, and the further optional substituents are preferably not selected from the values listed for Rc. A preferred value for G is $>N(Rc)$ or $>C(R^{11})(R^{12})$. Also preferred is G as O or S, particularly in (TC4) when Rp is hydrogen. Preferred is (TC4) as piperazinyl, morpholino or thiomorpholino or as tetrahydropyridin-4-yl.

Particularly preferred values for the optional substituents and groups defined in (TCa) to (TCc), and (TC1) to (TC4) are contained in the following definitions (TC5) to (TC11):—

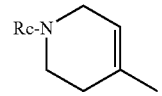
(TC5)

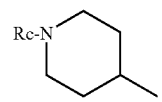
(TC6)

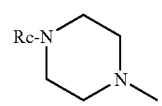
(TC7)

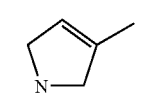
(TC8)

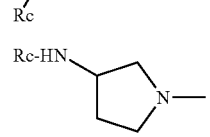
(TC9)

(TC10)

(TC11)

wherein Rc has any of the values listed hereinbefore or hereinafter.

Especially preferred are (TC5), (TC6), (TC7) and (TC9), most especially (TC5) in which Rc has any of the values listed hereinbefore or hereinafter (especially $R^{13}CO-$ with the preferable $R^{13}$ values given hereinafter). In (TC5) Rc is preferably selected from the group (Rc2), especially $R^{13}CO$— with the preferable $R^{13}$ values given hereinafter. In (TC7) Rc is preferably selected from group (Rc3) or (Rc4).

The above preferred values of (TCa) to (TCc) are particularly preferred when present in Q1 or Q2, especially Q1 (especially when HET is isoxazole). X as O or NH is particularly preferred.

(TDa) When T is a bicyclic spiro-ring system as defined in (TDa), it is preferably selected from a group of formula (TDa1) to (TDa9). The above preferred values of (TDa) are particularly preferred when present in Q1 or Q2, especially Q1.

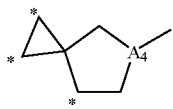
(TDa1)

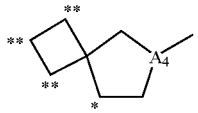
(TDa2)

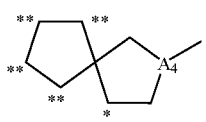
(TDa3)

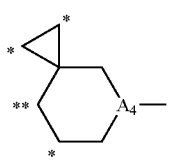
(TDa4)

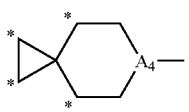
(TDa5)

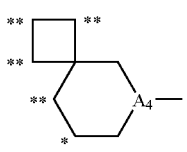
(TDa6)

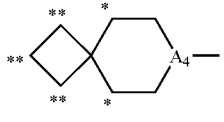
(TDa7)

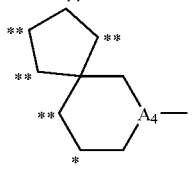
(TDa8)

-continued

(TDa9)

wherein;

(i) the $A_4$ linking group is a nitrogen atom or an $sp^3$ or $sp^2$ carbon atom (with the double bond, where appropriate, orientated in either direction); and (ii) one of the ring carbon atoms at positions marked * and ** is replaced by one of the following groups —NRc—, >CH—NHRc, >CH—NRc-(1–4C)alkyl, >CH—CH$_2$—NHRc, >CH—CH$_2$—NRc-(1–4C)alkyl [wherein a central —CH$_2$— chain link is optionally mono- or di-substituted by (1–4C)alkyl]; with the provisos that positions marked * are not replaced by —NH— in the ring containing the $A_4$ link when $A_4$ is a nitrogen atom or an $sp^2$ carbon atom, and that positions marked * are not replaced by —NH— in the three membered ring in (TDa1), (TDa4) and (TDa5); and (iii) the ring system is optionally (further) substituted on an available ring carbon atom by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, AR2-oxymethyl, AR2-thiomethyl, oxo (=O) (other than when the ring contains an >N—Rc and Rc is group (Rc2)) and also hydroxy or halo; wherein Rc has any of the values listed hereinbefore or hereinafter.

(TDb) When T is a 7-, 8- or 9-membered bicyclic ring system containing a bridge of 1, 2 or 3 carbon atoms as defined in (TDb), it is preferably selected from a group defined by the ring skeletons shown in formulae (TDb1) to (TDb14):—

7-membered ring skeletons

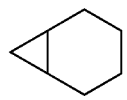
(TDb1)

[4,1,0]

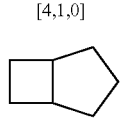
(TDb2)

[3,2,0]

(TDb3)

[3,1,1]

-continued

[2,2,1]

8-membered ring skeletons

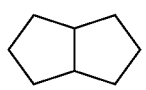

[3,3,0]

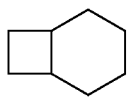

[4,2,0]

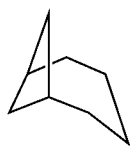

[4,1,1]

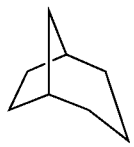

[3,2,1]

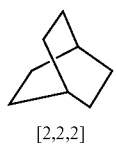

[2,2,2]

9-membered ring skeletons

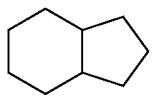

[4,3,0]

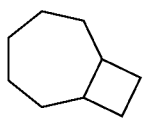

[5,2,0]

-continued (TDb4)

(TDb5)

(TDb6)

(TDb7)

(TDb8)

(TDb9)

(TDb10)

(TDb11)

(TDb12)

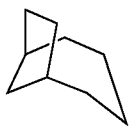

[4,2,1]

(TDb13)

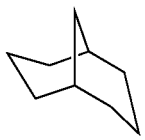

[3,3,1]

(TDb14)

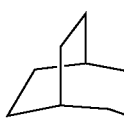

[3,2,2]

wherein;

(i) the ring system contains 0, 1 or 2 ring nitrogen atoms (and optionally a further O or S ring heteroatom), and when present the ring nitrogen, O or S heteroatom/s are at any position other than as part of the 3-membered ring in (TDb1);

(ii) the ring system is linked via a ring nitrogen atom or a ring $sp^3$ or $sp^2$ carbon atom (with the double bond, where appropriate, orientated in either direction) from any position in either ring [other than from a bridgehead position or from an $sp^2$ carbon atom in the 4-membered ring in (TDb2), (TDb6) and (TDb11)];

(iii) one of the ring carbon atoms at a position not adjacent to the linking position, is replaced (other than when the ring contains an O or S heteroatom) by one of the following groups —NRc— [not at a bridgehead position], >C(H)—NHRc, >C(H)—NRc-(1–4C)alkyl, >C(H)—CH$_2$—NHRc, —C(H)—CH$_2$—NRc-(1–4C)alkyl [wherein the hydrogen atom shown in brackets is not present when the replacement is made at a bridgehead position and wherein a central —CH$_2$— chain link is optionally mono- or di-substituted by (1–4C)alkyl]; with the proviso that when the ring system is linked via a ring nitrogen atom or an $sp^2$ carbon atom any replacement of a ring carbon atom by —NRc—, O or S is at least two carbon atoms away from the linking position; and (iv) the ring system is optionally (further) substituted on an available ring carbon atom as for the bicyclic spiro-ring systems described in (TDa); wherein Rc has any of the values listed hereinbefore or hereinafter.

It will be appreciated that unstable anti-Bredt compounds are not contemplated in this definition (i.e. compounds with stuctures (TDb3), (TDb4), (TDb7), (TDb8), (TDb9), (TDb12), (TDb13) and (TDb14) in which an $sp^2$ carbon atom is directed towards a bridgehead position).

Particularly preferred values of (TDb) are the following structures of formula (TDb4), (TDb8) and/or (TDb9); wherein Rc has any of the values listed hereinbefore or hereinafter. The above preferred values of (TDb) are particularly preferred when present in Q1 or Q2, especially Q1.

(TDb4a & b)

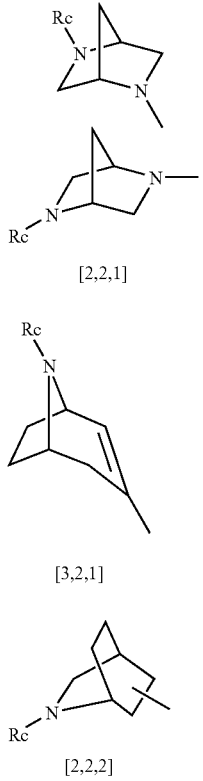

[2,2,1]

(TDb8)

[3,2,1]

(TDb9)

[2,2,2]

In another embodiment there is provided a compound of formula (I) as defined by formula (IP) below:

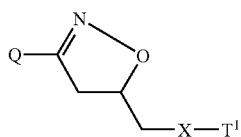
(IP)

wherein $T^1$ is a C-linked isoxazole ring which is optionally substituted on any available C atom by 1 or 2 substituents independently selected from (1–4C)alkyl, amino, (1–4C)alkylamino, (1–4C)alkoxy and halogen;

Q is

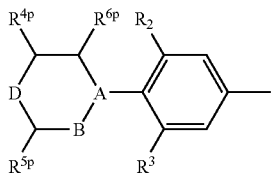

wherein:

$R^2$ and $R^3$ are independently hydrogen or fluoro;

$R^{6p}$ is hydrogen, (14C)alkyl, hydroxy, (1–4C)alkoxy or (2–4C)alkanoyloxy;

>A—B— is of the formula >C=C($R^a$)—, >CHCH$R^a$—, >C(OH)CH$R^a$— or >N—CH$_2$— (>represents two single bonds) wherein $R^a$ is hydrogen or (1–4C)alkyl;

D is O, S, SO, SO$_2$ or NR$^{7p}$;

$R^{4p}$ and $R^{5p}$ are independently oxo (=O) [but not when $R^7P$ is group (PC) below], (1–4C)alkyl, (1–4C)alkanoylamino-(1–4C)alkyl, hydroxy-(1–4C)alkyl, carboxy, (1–4C)alkoxycarbonyl, ARp-oxymethyl, ARp-thiomethyl (wherein ARp is as defined hereinbelow) or independently as defined for $R^{7p}$ hereinbelow with the proviso that $R^{4p}$ and $R^{5p}$ are not phenyl, benzyl, ARp (as defined hereinbelow), a tetrazole ring system, cyclopentyl or cyclohexyl; and when D is O or S, $R^{4p}$ and $R^{5p}$ are additionally independently hydroxy or bromo;

wherein $R^{7p}$ is selected from (PA) to (PE):—

(PA) hydrogen, cyano, 2-((1–4C)alkoxycarbonyl)ethenyl, 2-cyanoethenyl, 2-cyano-2-((1–4C)alkyl)ethenyl, 2-((1–4C)alkylaminocarbonyl)ethenyl;

(PB) phenyl, benzyl, ARp (as defined hereinbelow) or a tetrazole ring system [optionally mono-substituted in the 1- or 2- position of the tetrazole ring by (1–4C)alkyl, (2–4C)alkenyl, (2–4C)alkynyl or (1–4C)alkanoyl] wherein the tetrazole ring system is joined to the nitrogen in NR$^{7p}$ by a ring carbon atom;

(PC) R$^{10p}$CO—, R$^{10p}$SO$_2$— or R$^{10p}$CS— wherein R$^{10p}$ is selected from (PCa) to (PCf):—

(PCa) ARp (as defined hereinbelow);

(PCb) cyclopentyl or cyclohexyl or 1,3-dioxolan-4-yl or 1,4-dioxan-2-yl or 1,3-dioxan-4-yl [optionally mono- or disubstituted by substituents independently selected from (1–4C)alkyl (including geminal disubstitution), hydroxy (but excluding 1,3-dioxolan-4-yl, 1,4-dioxan-2-yl and 1,3-dioxan-4-yl substituted by hydroxy), (1–4C)alkoxy, (1–4C) alkylthio, acetamido, (1–4C)alkanoyl, cyano and trifluoromethyl];

(PCc) hydrogen, (1–4C)alkoxycarbonyl, trifluoromethyl, amino, (1–4C)alkylamino, di((1–4C)alkyl)amino, 2-(5- or 6-membered heteroaryl)ethenyl, 2-(5- or 6-membered (partially) hydrogenated heteroaryl)ethenyl, 2-phenylethenyl [wherein the heteroaryl or phenyl substituent is optionally substituted on an available carbon atom by up to three substituents independently selected from (1–4C)alkoxy, halo, cyano and (for the phenyl substituent only) (1–4C) alkylsulfonyl];

(PCd) (1–10C)alkyl [optionally substituted by one or more groups (including geminal disubstitution) each independently selected from hydroxy and amino, or optionally monosubstituted by cyano, halo, (1–10C)alkoxy, trifluoromethyl, (1–4C)alkoxy-(1–4C)alkoxy, (1–4C)alkoxy-(1–4C)alkoxy-(1–4C)alkoxy, (1–4C)alkanoyl, (1–4C)alkoxycarbonyl, (1–4C)alkylamino, di((1–4C)alkyl)amino, (1–6C) alkanoylamino, (1–4C)alkoxycarbonylamino, N-(1–4C)alkyl-N-(2–6C)alkanoylamino, (1–4C)alkylS(O)$_p$NH—, (1–4C)alkylS(O)$_p$((1–4C)alkyl)N—, fluoro(1–4C)alkylS(O)$_p$NH—, fluoro(1–4C)alkylS(O)$_p$((1–4C)

alkyl)N—, phosphono, (1–4C)alkoxy(hydroxy)phosphoryl, di-(1–4C)alkoxyphosphoryl, (1–4C)alkylS(O)$_q$—, phenyl, naphthyl, phenoxy, naphthoxy, phenylamino, naphthylamino, phenylS(O)$_q$—, naphthylS(O)$_q$— [wherein said phenyl and naphthyl groups are optionally substituted by up to three substituents independently selected from (1–4C)alkoxy, halo and cyano], or CYp (as defined hereinbelow), wherein (where appropriate) p is 1 or 2 and q is 0, 1 or 2];

(PCe) $R^{11p}C(O)O(1-6C)$alkyl wherein $R^{11p}$ is an optionally substituted 5- or 6-membered heteroaryl, optionally substituted phenyl, (1–4C)alkylamino, benzyloxy-(1–4C)alkyl or optionally substituted (1–10C)alkyl;

(PCf) $R^{12p}O$— wherein $R^{12p}$ is benzyl or optionally substituted (1–6C)alkyl;

(PD) $R^dOC(R^c)=CH(C=O)$—, $R^fC(=O)C(=O)$—, $R^gN=C(R^h)C(=O)$— or $R^iNHC(R^j)=CHC(=O)$— wherein $R^d$ is (1–6C)alkyl, $R^c$ is hydrogen or (1–6C)alkyl, or $R^d$ and $R^c$ together form a (3–4C)alkylene chain, $R^f$ is hydrogen, (1–6C)alkyl, hydroxy(1–6C)alkyl, (1–6C)alkoxy(1–6C)alkyl, amino, (1–4C)alkylamino, di-(1–4C)alkylamino, (1–6C)alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy, $R^g$ is (1–6C)alkyl, hydroxy or (1–6C)alkoxy, $R^h$ is hydrogen or (1–6C)alkyl, $R^i$ is hydrogen, (1–6C)alkyl, optionally substituted phenyl or an optionally substituted 5- or 6-membered heteroaryl [and (partially) hydrogenated versions thereof] and $R^j$ is hydrogen or (1–6C)alkyl; (PE) $R^{14p}CH(R^{13p})(CH_2)_m$— wherein m is 0 or 1, $R^{13p}$ is fluoro, cyano, (1–4C)alkoxy, (1–4C)alkylsulfonyl, (1–4C)alkoxycarbonyl or hydroxy, (provided that when m is 0, $R^{13p}$ is not fluoro or hydroxy) and $R^{14p}$ is hydrogen or (1–4C)alkyl;

wherein ARp is optionally substituted phenyl, optionally substituted phenyl(1–4C)alkyl, optionally substituted naphthyl, optionally substituted 5- or 6-membered heteroaryl;

wherein ARp is also an optionally substituted 5/6 or 6/6 bicyclic heteroaryl ring system, in which the bicyclic heteroaryl ring systems may be linked via an atom in either of the rings comprising the bicyclic system, and wherein both the mono- and bicyclic heteroaryl ring systems are linked via a ring carbon atom and may be (partially) hydrogenated;

wherein CYp is selected from:—

(i) 4-, 5- or 6-membered cycloalkyl ring;

(ii) 5- or 6-membered cycloalkenyl ring;

(iii) 5- or 6-membered heteroaryl, 5- or 6-membered heteroaryloxy, 5- or 6-membered heteroaryl-S(O)$_q$—, 5- or 6-membered heteroarylamino [and (partially) hydrogenated versions thereof] and (iv) 5/6 or 6/6 bicyclic heteroaryl, 5/6 or 6/6 bicyclic heteroaryloxy, 5/6 or 6/6 bicyclic heteroaryl-S(O)$_q$—, 5/6 or 6/6 bicyclic heteroarylamino [and (partially) hydrogenated versions thereof];

wherein q is 0, 1 or 2 and any of the aforementioned ring systems in CYp may be optionally substituted by up to three substituents independently selected from halo, (1–4C)alkyl [including geminal disubstitution when CYp is a cycloalkyl or cycloalkenyl ring], acyl, oxo and nitro-(1–4C)alkyl; and pharmaceutically-acceptable salts thereof.

In this embodiment (IP) of the specification the term 'alkyl' includes straight chained and branched structures. For example, (1–6C)alkyl includes propyl, isopropyl and tert-butyl. However, references to individual alkyl groups such as "propyl" are specific for the straight chained version only, and references to individual branched chain alkyl groups such as "isopropyl" are specific for the branched chain version only. A similar convention applies to other radicals, for example halo(1–4C)alkyl includes 1-bromoethyl and 2-bromoethyl.

In this embodiment (IP) of the specification a '5- or 6-membered heteroaryl' and 'heteroaryl (monocyclic) ring' means a 5- or 6-membered aryl ring wherein (unless stated otherwise) 1, 2 or 3 of the ring atoms are selected from nitrogen, oxygen and sulfur. Unless stated otherwise, such rings are fully aromatic. Particular examples of 5- or 6-membered heteroaryl ring systems are furan, pyrrole, pyrazole, imidazole, triazole, pyrimidine, pyridazine, pyridine, isoxazole, oxazole, isothiazole, thiazole and thiophene.

In this embodiment (IP) of the specification a '5/6 or 6/6 bicyclic heteroaryl ring system' and 'heteroaryl (bicyclic) ring' means an aromatic bicyclic ring system comprising a 6-membered ring fused to either a 5 membered ring or another 6 membered ring, the bicyclic ring system containing 1 to 4 heteroatoms selected from nitrogen, oxygen and sulfur. Unless stated otherwise, such rings are fully aromatic. Particular examples of 5/6 and 6/6 bicyclic ring systems are indole, benzofuran, benzoimidazole, benzothiophene, benzisothiazole, benzoxazole, benzisoxazole, pyridoimidazole, pyrimidoimidazole, quinoline, quinoxaline, quinazoline, phthalazine, cinnoline and naphthyridine.

In this embodiment (IP) of the specification a '4-, 5- or 6-membered cycloalkyl ring' means a cyclobutyl, cyclopentyl or cyclohexyl ring; and a '5- or 6-membered cycloalkenyl ring' a means cyclopentenyl or cyclohexenyl ring.

Particular optional substituents for alkyl, phenyl (and phenyl containing moieties) and naphthyl groups and ring carbon atoms in heteroaryl (mono or bicyclic) rings in $R^{11p}$, $R^{12p}$, $R^i$ and ARp include halo, (1–4C)alkyl, hydroxy, nitro, carbamoyl, (1–4C)alkylcarbamoyl, di-((1–4C)alkyl)carbamoyl, cyano, trifluoromethyl, trifluoromethoxy, amino, (1–4C)alkylamino, di((1–4C)alkyl)amino, (1–4C)alkylS(O)$_q$—, (wherein q is 0, 1 or 2), carboxy, (1–4C)alkoxycarbonyl, (2–4C)alkenyl, (2–4C)alkynyl, (1–4C)alkanoyl, (1–4C)alkoxy, (1–4C)alkylS(O)$_2$amino, (1–4C)alkanoylamino, benzoylamino, benzoyl, phenyl (optionally substituted by up to three substituents selected from halo, (1–4C)alkoxy or cyano), furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, hydroxy-(1–4C)alkyl, halo-(1–4C)alkyl, nitro(1–4C)alkyl, amino(1–4C)alkyl, cyano (1–4C)alkyl, (1–4C)alkanesulfonamido, aminosulfonyl, (1–4C)alkylaminosulfonyl and di-((1–4C)alkyl)aminosulfonyl. The phenyl and naphthyl groups and heteroaryl (mono- or bicyclic) rings in $R^{11p}$, $R^i$ and ARp may be mono- or disubstituted on ring carbon atoms with substituents independently selected from the above list of particular optional substituents.

For the avoidance of doubt, phosphono is —P(O)(OH)$_2$; (1–4C)alkoxy(hydroxy)-phosphoryl is a mono-(1–4C)alkoxy derivative of —O—P(O)(OH)$_2$; and di-(1–4C)alkoxyphosphoryl is a di-(1–4C)alkoxy derivative of —O—P(O)(OH)$_2$.

Particular optional substituents for alkyl, phenyl (and phenyl containing moieties) and naphthyl groups and ring carbon atoms in heteroaryl (mono or bicyclic) rings in $R^{11p}$, $R^{12p}$, Ri and ARp include halo, (1–4C)alkyl, hydroxy, nitro, carbamoyl, (1–4C)alkylcarbamoyl, di-((1–4C)alkyl)carbamoyl, cyano, trifluoromethyl, trifluoromethoxy, amino, (1–4C)alkylamino, di((1–4C)alkyl)amino, (1–4C)alkyl S(O)— (q is 0, 1 or 2), carboxy, (1–4C)alkoxycarbonyl, (2–4C)alkenyl, (2–4C)alkynyl, (1–4C)alkanoyl, (1–4C) alkoxy, (1–4C)alkylS(O)$_2$amino, (1–4C)alkanoylamino, benzoylamino, benzoyl, phenyl (optionally substituted by up to three substituents selected from halo, (1–4C)alkoxy or cyano), furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–14C) alkoxyimino(1–4C)alkyl, hydroxy-(1–4C)alkyl, halo-(1–4C)alkyl, nitro(1–4C)alkyl, amino(1–4C)alkyl, cyano (1–4C)alkyl, (1–14C)alkanesulfonamido, aminosulfonyl, (1–4C)alkylaminosulfonyl and di-((1–4C)alkyl)aminosulfonyl. The phenyl and naphthyl groups and heteroaryl (mono- or bicyclic) rings in $R^{11p}$, Ri and ARp may be mono- or di-substituted on ring carbon atoms with substituents independently selected from the above list of particular optional substituents.

In this specification the term 'alkyl' includes straight chained and branched structures. For example, (1–6C)alkyl includes propyl, isopropyl and tert-butyl.

However, references to individual alkyl groups such as "propyl" are specific for the straight chained version only, and references to individual branched chain alkyl groups such as "isopropyl" are specific for the branched chain version only. A similar convention applies to other radicals, for example halo(1–4C)alkyl includes 1-bromoethyl and 2-bromoethyl.

There follow particular and suitable values for certain substituents and groups referred to in this specification. These values may be used where appropriate with any of the definitions and embodiments disclosed hereinbefore, or hereinafter.

Examples of (1–4C)alkyl and (1–5C)alkyl include methyl, ethyl, propyl, isopropyl and t-butyl; examples of (1–6C)alkyl include methyl, ethyl, propyl, isopropyl, t-butyl, pentyl and hexyl; examples of (1–10C)alkyl include methyl, ethyl, propyl, isopropyl, pentyl, hexyl, heptyl, octyl and nonyl; examples of (1–4C)alkanoylamino-(1–4C)alkyl include formamidomethyl, acetamidomethyl and acetamidoethyl; examples of hydroxy(1–4C)alkyl and hydroxy (1–6C)alkyl include hydroxymethyl, 1-hydroxyethyl, 2-hydroxyethyl and 3-hydroxypropyl; examples of (1–4C) alkoxycarbonyl include methoxycarbonyl, ethoxycarbonyl and propoxycarbonyl; examples of 2-((1–4C)alkoxycarbonyl)ethenyl include 2-(methoxycarbonyl)ethenyl and 2-(ethoxycarbonyl)ethenyl; examples of 2-cyano-2-((1–4C) alkyl)ethenyl include 2-cyano-2-methylethenyl and 2-cyano-2-ethylethenyl; examples of 2-nitro-2-((1–4C)alkyl) ethenyl include 2-nitro-2-methylethenyl and 2-nitro-2-ethylethenyl; examples of 2-((1–4C)alkylaminocarbonyl) ethenyl include 2-(methylaminocarbonyl)ethenyl and 2-(ethylaminocarbonyl)ethenyl; examples of (2–4C)alkenyl include allyl and vinyl; examples of (2–4C)alkynyl include ethynyl and 2-propynyl; examples of (1–4C)alkanoyl include formyl, acetyl and propionyl; examples of (1–4C) alkoxy include methoxy, ethoxy and propoxy; examples of (1–6C)alkoxy and (1–10C)alkoxy include methoxy, ethoxy, propoxy and pentoxy; examples of (1–4C)alkylthio include methylthio and ethylthio; examples of (1–4C)alkylamino include methylamino, ethylamino and propylamino; examples of di-((1–4C)alkyl)amino include dimethylamino, N-ethyl-N-methylamino, diethylamino, N-methyl-N-propylamino and dipropylamino; examples of halo groups include fluoro, chloro and bromo; examples of (1–4C)alkylsulfonyl include methylsulfonyl and ethylsulfonyl; examples of(1–4C)alkoxy-(1–4C)alkoxy and (1–6C)alkoxy-(1–6C) alkoxy include methoxymethoxy, 2-methoxyethoxy, 2-ethoxyethoxy and 3-methoxypropoxy;

examples of (1–4C)alkoxy-(1–4C)alkoxy-(1–4C)alkoxy include 2-(methoxymethoxy)ethoxy, 2-(2-methoxyethoxy)ethoxy; 3-(2-methoxyethoxy)propoxy and 2-(2-ethoxyethoxy)ethoxy; examples of (1–4C)alkylS (O)$_2$amino include methylsulfonylamino and ethylsulfonylamino; examples of (1–4C)alkanoylamino and (1–6C)alkanoylamino include formamido, acetamido and propionylamino; examples of (1–4C)alkoxycarbonylamino include methoxycarbonylamino and ethoxycarbonylamino; examples of N-(1–4C)alkyl-N-(1–6C)alkanoylamino include N-methylacetamido, N-ethylacetamido and N-methylpropionamido; examples of (1–4C)alkylS(O)$_p$NH— wherein p is 1 or 2 include methylsulfinylamino, methylsulfonylamino, ethylsulfinylamino and ethylsulfonylamino; examples of (1–4C)alkylS(O)$_p$((14C)alkyl)N— wherein p is 1 or 2 include methylsulfinylmethylamino, methylsulfonylmethylamino, 2-(ethylsulfinyl)ethylamino and 2-(ethylsulfonyl)ethylamino; examples of fluoro(1–4C)alkylS (O)$_p$NH— wherein p is 1 or 2 include trifluoromethylsulfinylamino and trifluoromethylsulfonylamino; examples of fluoro(1–4C)alkylS(O)$_p$((1–4C)alkyl)NH— wherein p is 1 or 2 include trifluoromethylsulfinylmethylamino and trifluoromethylsulfonylmethylamino examples of (1–4C)alkoxy (hydroxy)phosphoryl include methoxy(hydroxy)phosphoryl and ethoxy(hydroxy)phosphoryl; examples of di-(1–4C) alkoxyphosphoryl include di-methoxyphosphoryl, di-ethoxyphosphoryl and ethoxy(methoxy)phosphoryl; examples of (1–4C)alkylS(O)$_q$— wherein q is 0, 1 or 2 include methylthio, ethylthio, methylsulfinyl, ethylsulfinyl, methylsulfonyl and ethylsulfonyl; examples of phenylS(O)$_q$ and naphthylS(O)$_q$— wherein q is 0, 1 or 2 are phenylthio, phenylsulfinyl, phenylsulfonyl and naphthylthio, naphthylsulfinyl and naphthylsulfonyl respectively; examples of benzyloxy-(1–4C)alkyl include benzyloxymethyl and benzyloxyethyl; examples of a (3–4C)alkylene chain are trimethylene or tetramethylene; examples of (1–6C)alkoxy-(1–6C)alkyl include methoxymethyl, ethoxymethyl and 2-methoxyethyl; examples of hydroxy-(2–4C)alkoxy include 2-hydroxyethoxy and 3-hydroxypropoxy; examples of (1–4C)alkylamino-(2–6C)alkoxy include 2-methylaminoethoxy and 2-ethylaminoethoxy; examples of di-(1–4C) alkylamino-(2–6C)alkoxy include 2-dimethylaminoethoxy and 2-diethylaminoethoxy; examples of phenyl(1–4C)alkyl include benzyl and phenethyl; examples of (1–4C)alkylcarbamoyl include methylcarbamoyl and ethylcarbamoyl;

examples of di((1–4C)alkyl)carbamoyl include di(methyl) carbamoyl and di(ethyl)carbamoyl; examples of hydroxyimino(1–4C)alkyl include hydroxyiminomethyl, 2-(hydroxyimino)ethyl and 1-(hydroxyimino)ethyl; examples of (1–4C)alkoxyimino-(1–4C)alkyl include methoxyiminomethyl, ethoxyiminomethyl, 1-(methoxyimino)ethyl and 2-(methoxyimino)ethyl; examples of halo(1–4C)alkyl include, halomethyl, 1-haloethyl, 2-haloethyl, and 3-halopropyl; examples of nitro(1–4C)alkyl include nitromethyl, 1-nitroethyl, 2-nitroethyl and 3-nitropropyl; examples of amino(1–4C)alkyl include aminomethyl, 1-aminoethyl, 2-aminoethyl and 3-aminopropyl; examples of cyano(1–4C) alkyl include cyanomethyl, 1-cyanoethyl, 2-cyanoethyl and 3-cyanopropyl; examples of(1–4C)alkanesulfonamido include methanesulfonamido and ethanesulfonamido;

examples of (1–4C)alkylaminosulfonyl include methylaminosulfonyl and ethylaminosulfonyl; and examples of di-(1–4C)alkylaminosulfonyl include dimethylaminosulfonyl, diethylaminosulfonyl and N-methyl-N-ethylaminosulfonyl; examples of (1–4C)alkanesulfonyloxy include methylsulfonyloxy, ethylsulfonyloxy and propylsulfonyloxy; examples of (1–4C)alkanoyloxy include acetoxy; examples of (1–4C)alkylaminocarbonyl include methylaminocarbonyl and ethylaminocarbonyl; examples of di((1–4C)alkyl)aminocarbonyl include dimethylaminocarbonyl and diethylaminocarbonyl; examples of (3–8C)cycloalkyl include cyclopropyl, cyclobutyl, cyclopentyl and cyclohexyl; examples of (4–7C)cycloalkyl include cyclobutyl, cyclopentyl and cyclohexyl; examples of di(N-(1–4C)alkyl) aminomethylimino include dimethylaminomethylimino and diethylaminomethylimino.

Particular values for AR2 include, for example, for those AR2 containing one heteroatom, furan, pyrrole, thiophene; for those AR2 containing one to four N atoms, pyrazole, imidazole, pyridine, pyrimidine, pyrazine, pyridazine, 1,2,3- & 1,2,4-triazole and tetrazole; for those AR2 containing one N and one O atom, oxazole, isoxazole and oxazine; for those AR2 containing one N and one S atom, thiazole and isothiazole; for those AR2 containing two N atoms and one S atom, 1,2,4- and 1,3,4-thiadiazole.

Particular examples of AR2a include, for example, dihydropyrrole (especially 2,5-dihydropyrrol-4-yl) and tetrahydropyridine (especially 1,2,5,6-tetrahydropyrid-4-yl).

Particular examples of AR2b include, for example, tetrahydrofuran, pyrrolidine, morpholine (preferably morpholino), thiomorpholine (preferably thiomorpholino), piperazine (preferably piperazino), imidazoline and piperidine, 1,3-dioxolan-4-yl, 1,3-dioxan-4-yl, 1,3-dioxan-5-yl and 1,4-dioxan-2-yl.

Particular values for AR3 include, for example, bicyclic benzo-fused systems containing a 5- or 6-membered heteroaryl ring containing one nitrogen atom and optionally 1–3 further heteroatoms chosen from oxygen, sulfur and nitrogen. Specific examples of such ring systems include, for example, indole, benzofuran, benzothiophene, benzimidazole, benzothiazole, benzisothiazole, benzoxazole, benzisoxazole, quinoline, quinoxaline, quinazoline, phthalazine and cinnoline.

Other particular examples of AR3 include 5/5-, 5/6 and 6/6 bicyclic ring systems containing heteroatoms in both of the rings. Specific examples of such ring systems include, for example, purine and naphthyridine.

Further particular examples of AR3 include bicyclic heteroaryl ring systems with at least one bridgehead nitrogen and optionally a further 1–3 heteroatoms chosen from oxygen, sulfur and nitrogen. Specific examples of such ring systems include, for example, 3H-pyrrolo[1,2-a]pyrrole, pyrrolo[2,1-b]thiazole, 1H-imidazo[1,2-a]pyrrole, 1H-imidazo[1,2-a]imidazole, 1H,3H-pyrrolo[1,2-c]oxazole, 1H-imidazo[1,5-a]pyrrole, pyrrolo[1,2-b]isoxazole, imidazo[5,1-b]thiazole, imidazo[2,1-b]thiazole, indolizine, imidazo[1,2-a]pyridine, imidazo[1,5-a]pyridine, pyrazolo[1,5-a]pyridine, pyrrolo[1,2-b]pyridazine, pyrrolo[1,2-c]pyrimidine, pyrrolo[1,2-a]pyrazine, pyrrolo[1,2-a]pyrimidine, pyrido[2,1-c]-s-triazole, s-triazolo[1,5-a]pyridine, imidazo[1,2-c]pyrimidine, imidazo[1,2-a]pyrazine, imidazo[1,2-a]pyrimidine, imidazo[1,5-a]pyrazine, imidazo[1,5-a]pyrimidine, imidazo[1,2-b]-pyridazine, s-triazolo[4,3-a]pyrimidine, imidazo[5,1-b]oxazole and imidazo[2,1-b]oxazole. Other specific examples of such ring systems include, for example, [1H]-pyrrolo[2,1-c]oxazine, [3H]-oxazolo[3,4-a]pyridine, [6H]-pyrrolo[2,1-c]oxazine and pyrido[2,1-c][1,4]oxazine. Other specific examples of 5/5- bicyclic ring systems are imidazooxazole or imidazothiazole, in particular imidazo[5,1-b]thiazole, imidazo[2,1-b]thiazole, imidazo[5,1-b]oxazole or imidazo[2,1-b]oxazole.

Particular examples of AR3a and AR3b include, for example, indoline, 1,3,4,6,9,9a-hexahydropyrido[2,1c][1,4]oxazin-8-yl, 1,2,3,5,8,8a-hexahydroimidazo[1,5a]pyridin-7-yl, 1,5,8,8a-tetrahydrooxazolo[3,4a]pyridin-7-yl, 1,5,6,7,8,8a-hexahydrooxazolo[3,4a]pyridin-7-yl, (7aS)[3H,5H]-1,7a-dihydropyrrolo[1,2c]oxazol-6-yl, (7aS)[5H]-1,2,3,7a-tetrahydropyrrolo[1,2c]imidazol-6-yl, (7aR)[3H,5H]-1,7a-dihydropyrrolo[1,2c]oxazol-6-yl, [3H,5H]-pyrrolo[1,2-c]oxazol-6-yl, [5H]-2,3-dihydropyrrolo[1,2-c]imidazol-6-yl, [3H,5H]-pyrrolo[1,2-c]thiazol-6-yl, [3H,5H]-1,7a-dihydropyrrolo[1,2-c]thiazol-6-yl, [5H]-pyrrolo[1,2-c]imidazol-6-yl, [1H]-3,4,8,8a-tetrahydropyrrolo[2,1-c]oxazin-7-yl, [3H]-1,5,8,8a-tetrahydrooxazolo[3,4-a]pyrid-7-yl, [3H]-5,8-dihydroxazolo[3,4-a]pyrid-7-yl and 5,8-dihydroimidazo[1,5-a]pyrid-7-yl.

Particular values for AR4 include, for example, pyrrolo[a]quinoline, 2,3-pyrroloisoquinoline, pyrrolo[a]isoquinoline,1H-pyrrolo[1,2-a]benzimidazole, 9H-imidazo[1,2-a]indole, 5H-imidazo[2,1-a]isoindole, 1H-imidazo[3,4-a]indole, imidazo[1,2-a]quinoline, imidazo[2,1-a]isoquinoline, imidazo[1,5-a]quinoline and imidazo[5,1-a]isoquinoline.

The nomenclature used is that found in, for example, "Heterocyclic Compounds (Systems with bridgehead nitrogen), W. L. Mosby (Intercsience Publishers Inc., New York), 1961, Parts 1 and 2.

Where optional substituents are listed such substitution is preferably not geminal disubstitution unless stated otherwise. If not stated elsewhere suitable optional substituents for a particular group are those as stated for similar groups herein.

Suitable substituents on AR1, AR2, AR2a, AR2b, AR3, AR3a, AR3b, AR4, AR4a, CY1 and CY2 are (on an available carbon atom) up to three substituents independently selected from (1–4C)alkyl {optionally substituted by (preferably one) substituents selected independently from hydroxy, trifluoromethyl, (1–4C)alkyl S(O)$_q$— (q is 0, 1 or 2) (this last substituent preferably on AR1 only), (1–4C)alkoxy, (1–4C)alkoxycarbonyl, cyano, nitro, (1–4C)alkanoylamino, —CONRvRw or —NRvRw}, trifluoromethyl, hydroxy, halo, nitro, cyano, thiol, (1–4C)alkoxy, (1–4C)alkanoyloxy, dimethylaminomethyleneaminocarbonyl, di(N-(1–4C)alkyl)aminomethylimino, carboxy, (1–4C)alkoxycarbonyl, (1–4C)alkanoyl, (1–4C)alkylSO$_2$amino, (2–4C)alkenyl {optionally substituted by carboxy or (1–4C)alkoxycarbonyl}, (2–4C)alkynyl, (1–4C)alkanoylamino, oxo (═O), thioxo (═S), (1–4C)alkanoylamino {the (1–4C)alkanoyl group being optionally substituted by hydroxy}, (1–4C)alkyl S(O)$_q$— (q is 0, 1 or 2) {the (1–4C)alkyl group being optionally substituted by one or more groups independently selected from cyano, hydroxy and (1–4C)alkoxy}, —CONRvRw or —NRvRw [wherein Rv is hydrogen or (1–4C)alkyl; Rw is hydrogen or (1–4C)alkyl].

Further suitable substituents on AR1, AR2, AR2a, AR2b, AR3, AR3a, AR3b, AR4, AR4a, CY1 and CY2 (on an available carbon atom), and also on alkyl groups (unless indicated otherwise) are up to three substituents independently selected from trifluoromethoxy, benzoylamino, benzoyl, phenyl {optionally substituted by up to three substituents independently selected from halo, (1–4C)alkoxy or cyano}, furan, pyrrole, pyrazole, imidazole, triazole, pyrimidine, pyridazine, pyridine, isoxazole, oxazole, isothiazole, thiazole, thiophene, hydroxyimino(1–4C)alkyl, (1–4C)alkoxyimino(1–4C)alkyl, halo-(1–4C)alkyl, (1–4C)alkanesulfonamido, —SO$_2$NRvRw [wherein Rv is hydrogen or (1–4C)alkyl; Rw is hydrogen or (1–4C)alkyl].

Preferable optional substituents on Ar2b as 1,3-dioxolan-4-yl, 1,3-dioxan-4-yl, 1,3-dioxan-5-yl or 1,4-dioxan-2-yl are mono- or disubstitution by substituents independently selected from (1–4C)alkyl (including geminal disubstitution), (1–4C)alkoxy, (1–4C)alkylthio, acetamido, (1–4C)alkanoyl, cyano, trifluoromethyl and phenyl].

Preferable optional substituents on CY1 & CY2 are mono- or disubstitution by substituents independently selected from (1–4C)alkyl (including geminal disubstitution), hydroxy, (1–4C)alkoxy, (1–4C)alkylthio, acetamido, (1–4C)alkanoyl, cyano, and trifluoromethyl.

Suitable substituents on AR2, AR2a, AR2b, AR3, AR3a, AR3b, AR4 and AR4a are (on an available nitrogen atom, where such substitution does not result in quaternization) (1–4C)alkyl, (1–4C)alkanoyl {wherein the (1–4C)alkyl and (1–4C)alkanoyl groups are optionally substituted by (preferably one) substituents independently selected from cyano, hydroxy, nitro, trifluoromethyl, (1–4C)alkyl S(O)$_q$— (q is 0, 1 or 2), (1–4C)alkoxy, (1–4C)alkoxycarbonyl, (1–4C)alkanoylamino, —CONRvRw or —NRvRw [wherein Rv is hydrogen or (1–4C)alkyl; Rw is hydrogen or (1–4C)alkyl]}, (2–4C)alkenyl, (2–4C)alkynyl, (1–4C)alkoxycarbonyl or oxo (to form an N-oxide).

Suitable pharmaceutically-acceptable salts include acid addition salts such as methanesulfonate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the formula (I) or a pharmaceutically-acceptable salt thereof.

Various forms of prodrugs are known in the art, for examples see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Phann Bull, 2, 692 (1984).

An in-vivo hydrolysable ester of a compound of the formula (I) or a pharmaceutically-acceptable salt thereof containing carboxy or hydroxy group is, for example, a pharmaceutically-acceptable ester which is hydrolysed in the human or animal body to produce the parent acid or alcohol.

Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C)cycloalkoxycarbonyloxy(1–6C)alkyl esters for example 1-cyclohexylcarbonyloxyethyl; 1,3-dioxolan-2-onylmethyl esters for example 5-methyl-1,3-dioxolan-2-ylmethyl; and (1–6C)alkoxycarbonyloxyethyl esters for example 1-methoxycarbonyloxyethyl and may be formed at any carboxy group in the compounds of this invention.

An in-vivo hydrolysable ester of a compound of the formula (I) or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1–10C)alkanoyl, benzoyl, phenylacetyl and substituted benzoyl and phenylacetyl, (1–10C)alkoxycarbonyl (to give alkyl carbonate esters), di-(1–4C)alkylcarbamoyl and N-(di-(1–4C)alkylaminoethyl)-N-(1–4C)alkylcarbamoyl (to give carbamates), di-(1–4C)alkylaminoacetyl and carboxyacetyl. Examples of substituents on benzoyl include chloromethyl or aminomethyl, (1–4C)alkylaminomethyl and di-((1–4C)alkyl)aminomethyl, and morpholino or piperazino linked from a ring nitrogen atom via a methylene linking group to the 3- or 4-position of the benzoyl ring.

Certain suitable in-vivo hydrolysable esters of a compound of the formula (I) are described within the definitions listed in this specification, for example esters described by the definition (Rc2d), and some groups within (Rc2c). Suitable in-vivo hydrolysable esters of a compound of the formula (I) are described as follows. For example, a 1,2-diol may be cyclised to form a cyclic ester of formula (PD1) or a pyrophosphate of formula (PD2):

(PD1)

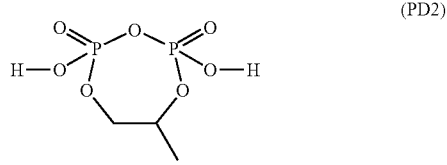
(PD2)

Particularly interesting are such cyclised pro-drugs when the 1,2-diol is on a (1–4C)alkyl chain linked to a carbonyl group in a substituent of formula Rc borne by a nitrogen atom in (TC4). Esters of compounds of formula (I) wherein the HO— function/s in (PD1) and (PD2) are protected by (1–4C)allyl, phenyl or benzyl are useful intermediates for the preparation of such pro-drugs.

Further in-vivo hydrolysable esters include phosphoramidic esters, and also compounds of formula (I) in which any free hydroxy group independently forms a phosphoryl (npd is 1) or phosphiryl (npd is 0) ester of the formula (PD3):

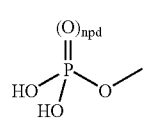

(PD3)

Useful intermediates for the preparation of such esters include compounds containing a group/s of formula (PD3) in which either or both of the —OH groups in (PD3) is independently protected by (1–4C)alkyl (such compounds also being interesting compounds in their own right), phenyl or phenyl-(1–4C)alkyl (such phenyl groups being optionally substituted by 1 or 2 groups independently selected from (1–4C)alkyl, nitro, halo and (1–4C)alkoxy).

Thus, prodrugs containing groups such as (PD1), (PD2) and (PD3) may be prepared by reaction of a compound of formula (I) containing suitable hydroxy group/s with a suitably protected phosphorylating agent (for example, containing a chloro or dialkylamino leaving group), followed by oxidation (if necessary) and deprotection.

When a compound of formula (I) contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Other interesting in-vivo hydrolysable esters include, for example, those in which Rc is defined by, for example, $R^{14}C(O)O(1–6C)alkyl-CO$— (wherein $R^{14}$ is for example, benzyloxy-(1–4C)alkyl, or phenyl). Suitable substituents on a phenyl group in such esters include, for example, 4-(1–4C) piperazino-(1–4C)alkyl, piperazino-(1–4C)alkyl and morpholino-(1–4C)alkyl.

Where pharmaceutically-acceptable salts of an in-vivo hydrolysable ester may be formed this is achieved by conventional techniques Thus, for example, compounds containing a group of formula (PD1), (PD2) and/or (PD3) may ionise (partially or fully) to form salts with an appropriate number of counter-ions. Thus, by way of example, if an in-vivo hydrolysable ester prodrug of a compound of formula (I) contains two (PD3) groups, there are four HO—P— functionalities present in the overall molecule, each of which may form an appropriate salt (i.e. the overall molecule may form, for example, a mono-, di-, tri- or tetra-sodium salt).

The compounds of the present invention have a chiral centre at the C-5 position of the isoxazoline ring. The pharmaceutically active enantiomer is of the formula (IA):

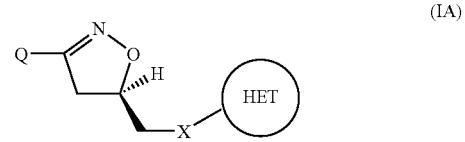

(IA)

The present invention includes the pure enantiomer depicted above or mixtures of the 5R and 5S enantiomers, for example a racemic mixture. If a mixture of enantiomers is used, a larger amount (depending upon the ratio of the enantiomers) will be required to achieve the same effect as the same weight of the pharmaceutically active enantiomer. For the avoidance of doubt the enantiomer depicted above is the 5(R) isomer.

Furthermore, some compounds of the formula (I) may have other chiral centres. It is to be understood that the invention encompasses all such optical and diastereo-isomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

The invention relates to all tautomeric forms of the compounds of the formula (I) that possess antibacterial activity.

It is also to be understood that certain compounds of the formula (I) can exist in solvated as well as unsolvated forms such as, for example, hydrated forms.

It is to be understood that the invention encompasses all such solvated forms which possess antibacterial activity.

It is also to be understood that certain compounds of the formula (I) may exhibit polymorphism, and that the invention encompasses all such forms which possess antibacterial activity.

As stated before, we have discovered a range of compounds that have good activity against a broad range of Gram-positive pathogens including organisms known to be resistant to most commonly used antibiotics. Physical and/or pharmacokinetic properties, for example increased stability to mammalian peptidase metabolism and a favourable toxicological profile are important features. The following compounds possess favourable physical and/or pharmacokinetic properties and are preferred.

Particularly preferred compounds of the invention comprise a compound of formula (I) or of formula (IP), or a pharmaceutically-acceptable salt or an in-vivo hydrolysable ester thereof, wherein the substituents Q, HET, T, $T^1$ and other substituents mentioned above have values disclosed hereinbefore, or any of the following values (which may be used where appropriate with any of the definitions and embodiments disclosed hereinbefore or hereinafter):

Preferably Q is selected from Q1, Q2, Q4, Q6 and Q9; especially Q1, Q2 and Q9; more particularly Q1 and Q2; and most preferably Q is Q1.

Preferably T is selected from (TAf), (TDb) or (TC); especially groups (TAf), (TCb) and (TCc); more particularly (TC2), (TC3) and (TC4); and most preferably (TC5), (TC7) or (TC9), and most particularly (TC9) and (TC5). Especially preferred is each of these values of T when present in Q1 and Q2, particularly in Q1.

Preferable values for other substituents (which may be used where appropriate with any of the definitions and embodiments disclosed hereinbefore or hereinafter) are:—

(a0) In one embodiment HET is a 6-membered heteroaryl as defined herein, and in another embodiment HET is a 5-membered heteroaryl as defined herein.

(a) When HET is a 6-membered heteroaryl as defined herein, preferably HET is pyrimidine, pyridazine or pyrazine; more preferably HET is pyrimidin-2-yl, pyridazin-3-yl or pyrazin-2-yl; preferably HET is unsubstituted.

(b) When HET is a 5-membered heteroaryl as defined herein, preferably HET is not thiazole; preferably HET is pyrazole, imidazole, oxazole, isoxazole, 1,2,4- oxadiazole, 1,2,5-oxadiazole, 1,3,4-oxadiazole, isothiazole, 1,2,3-thiadiazole, 1,2,4-thiadiazole, 1,2,5-thiadiazole, 1,3,4-thiadiazole, 1,2,3-triazole or 1,2,4-triazole.

(c) Yet more preferably HET is pyrazol-3-yl, imidazol-2-yl (optionally 3-methyl substituted), imidazol-4-yl (optionally 1-methyl substituted), oxazol-2-yl, isoxazol-3-yl, isoxazol-5-yl , 1,2,5-oxadiazol-3-yl, 1,2,4-oxadiazol-3-yl, 1,3,4-oxadiazol-2-yl, isothiazol-3-yl, isothiazol-5-yl, 1,2,3-thiadiazol-4-yl, 1,2,4-thiadiazol-3-yl, 1,2,4-thiadiazol-5-yl, 1,2,5-thiadiazol-3-yl or 1,3,4-thiadiazol-2-yl.

(d) Further preferred as HET is isoxazol-3-yl, isoxazol-5-yl, 1,2,5-oxadiazol-3-yl, 1,2,4-oxadiazol-3-yl, 1,3,4-oxadiazol-2-yl, isothiazol-3-yl, isothiazol-5-yl, 1,2,3-thiadiazol-4-yl, 1,2,4-thiadiazol-3-yl, 1,2,4-thiadiazol-5-yl, 1,2,5-thiadiazol-3-yl or 1,3,4-thiadiazol-2-yl.

(e) Particularly preferred as HET is isoxazol-3-yl, isoxazol-5-yl, 1,2,5-oxadiazol-3-yl, isothiazol-3-yl , isothiazol-5-yl, 1,2,3-thiadiazol-4-yl, 1,2,4thiadiazol-3-yl, 1,2,4-thiadiazol-5-yl, 1,2,5-thiadiazol-3-yl or 1,3,4-thiadiazol-2-yl.

(f) Most preferred is HET as isoxazole (optionally substituted as disclosed hereinbefore), particularly isoxazol-3-yl.

(g) Preferably HET is unsubstituted.

(g1) Preferably X is O, S or NH; preferably X is O or NH (particularly NH) when T is a C-linked moiety and preferably X is NH when T is an N-linked moiety;

(h) Preferably $R^{6p}$ is hydrogen;

(i) Preferably $R^{4p}$ and $R^{5p}$ are independently selected from hydrogen, (1–4C)alkyl, carboxy, (1–4C)alkoxycarbonyl, hydroxymethyl, (1–4C)alkoxymethyl or carbamoyl;

(j) More preferably $R^{4p}$ and $R^{5p}$ are hydrogen;

(k) Preferably $R^2$ and $R^3$ are hydrogen or fluoro;

(l) In one aspect of the invention more preferably one of $R^2$ and $R^3$ is hydrogen and the other fluoro. In another aspect of the invention both $R^2$ and $R^3$ are fluoro;

(m) Preferably >A—B— is of the formula <C=CH— (i.e. $R^a$ is preferably hydrogen) or >N—CH$_2$—;

(n) Preferably D is O or $NR^{7p}$;

(o) Preferably $R^{7p}$ is ARp, $R^{10p}CO$—, $R^{10p}SO_2$—, $R^{10p}CS$—;

(p) More preferably $R^{7p}$ is ARp (most preferably benzyl, pyrimidyl, pyridinyl, pyridazinyl or pyrazinyl) or $R^{10p}CO$—;

(q) Particularly $R^{7p}$ is $R^{10p}CO$—;

(q1) Especially preferred is $R^{10p}CO$— (or $R^{13}CO$—) wherein $R^{10p}$ (or $R^{13}$) is (1–10)alkyl optionally substituted by hydroxy or (1–4C)alkylS(O)$_q$— (wherein q is 0, 1 or 2), wherein the (1–4C)alkyl group is optionally substituted as defined herein for this particular substituent;

(r) Preferably ARp is 5- or 6-membered heteroaryl; more preferably ARp is 6-membered heteroaryl, such as pyridinyl;

(s) Preferred substituents for phenyl and carbon atoms in heteroaryl (mono- and bicyclic) ring systems in ARp, $R^{11p}$ and $R^i$ include halo, (1–4C)alkyl, hydroxy, nitro, amino, cyano, (1–4C)alkylS(O)$_p$— and (1–4C)alkoxy;

(t) Preferably the optionally substituted ring systems in ARp, $R^{11p}$ and $R^i$ are unsubstituted;

(u) In another embodiment in the definition of $R^{10p}$ in (PC) of embodiment (IP), 1,3-dioxolan-4-yl and 1,4-dioxan-2-yl are excluded.

(v) In one aspect of the invention, preferably $R^{10p}$ is (1–4C)alkoxycarbonyl, hydroxy(1–4C)alkyl, (1–4C)alkyl (optionally substituted by one or two hydroxy groups, or by an (1–4C)alkanoyl group), (1–4C)alkylamino, dimethylamino (1–4C)alkyl, (1–4C)alkoxymethyl, (1 4C)alkanoylmethyl, (1–4C)alkanoyloxy(1–4C)alkyl, (1–5C)alkoxy or 2-cyanoethyl;

(w) In one aspect of the invention, more preferably $R^{10p}$ is 1,2-dihydroxyethyl, 1,3-dihydroxyprop-2-yl, 1,2,3-trihydroxyprop-1-yl, methoxycarbonyl, hydroxymethyl, methyl, methylamino, dimethylaminomethyl, methoxymethyl, acetoxymethyl, methoxy, methylthio, naphthyl, tert-butoxy or 2-cyanoethyl;

(x) In one aspect of the invention, particularly $R^{10p}$ is 1,2-dihydroxyethyl, 1,3-dihydroxyprop-2-yl or 1,2,3-trihydroxyprop-1-yl;

(y) In another aspect of the invention preferably $R^{10p}$ is hydrogen, (1–10C)alkyl [optionally substituted by one or more hydroxy] or $R^{11p}C(O)O(1–6C)$alkyl.

(z) In another aspect of the invention, more preferably $R^{10p}$ is hydrogen, hydroxymethyl, 1,2-dihydroxyethyl or acteoxyacetyl; and/or Rc2c is (1–10C)alkyl optionally substituted by (1–4C)alkyl S(O)$_q$— (q is 0–2), optionally substituted as in claim 1.

(aa) Preferably $R^{11p}$ is (1–10C)alkyl;

(ab) Preferred optional substituents for (1–10C)alkyl in $R^{11p}$ are hydroxy, cyano, amino, (1–4C)alkylamino, di((1–4C)alkyl)amino, (1–4C)alkylS(O)$_p$ (wherein p is 1 or 2), carboxy, (1–4C)alkoxycarbonyl, (1–4C)alkoxy, piperazino or morpholino;

(ac) Preferred optional substituents for (1–6C)alkyl in $R^{12p}$ are hydroxy, (1–4C)alkoxy, cyano, amino, (1–4C)alkylamino, di((1–2C)alkyl)amino, (1–4C)alkylS(O)$_p$— (wherein p is 1 or 2);

(ad) Preferably 5- or 6-membered heteroaryl in $R^{11p}$ is pyridinyl or imidazol-1-yl;

(ae) Preferably $R^{12p}$ is (1–6C)alkyl; most preferably $R^{12p}$ is t-butyl or methyl;

(af) Preferably $R^{13p}$ is cyano or fluoro;

(ag) Preferably $R^{14p}$ is hydrogen;

(ah) Preferably CYp is naphthoxy, especially naphth-1-oxy or naphth-2-oxy.

Where preferable values are given for substituents in a compound of formula (IP), the corresponding substituents in a compound of formula (I) have the same preferable values (thus, for example, Rc and $R^{13}$ in formula (I) correspond with $R^{7p}$ and $R^{10p}$ in formula (IP), and similarly for groups D and G). The preferred values of $R^{7p}$, for example, defined with reference to (IP) are also preferred values of Rc and may be used as preferred values of Rc in any compound of formula (I). For compounds of formula (I) preferred values for Rc are those in group (Rc2) when present in any of the definitions herein containing Rc—for example when present in compounds in which there is a (TC5) or (TC9) ring system. The preferred values for $R^{10p}$ listed above for compounds of formula (IP) are also preferred values for $R^{13}$ in compounds of formula (I). In the definition of (Rc2c) the AR2a, AR2b, AR3a and AR3b versions of AR2 and AR3 containing groups are preferably excluded.

In another aspect, HET is a C-linked 5-membered heteroaryl ring containing 2 or 3 heteroatoms independently selected from N, O and S (with the proviso that there are no O—O, O—S, S—S or N—S bonds), which ring is optionally substituted on any available C atom (provided that when a N atom is adjacent to the NH-link, there is no substitution on any C atom that is adjacent to this N atom) by 1 or 2 substituents independently selected from (1–4C)alkyl, amino, (1–4C)alkylamino, (1–4C)alkoxy and halogen, and/or on an available N atom (provided that the ring is not thereby quaternised), by (1–4C)alkyl.

Particular examples of HET as a 5-membered heteroaryl rings containing 2 or 3 heteroatoms independently selected from N, O and S (with the proviso that there are no O—O, O—S or S—S bonds; and in an alternative embodiment, also no N—S bonds) are pyrazole, imidazole, 1,2,3-triazole, 1,2,4-triazole, oxazole, isoxazole, thiazole, 1,2,3-oxadiazole, 1,2,4-oxadiazole, 1,2,5-oxadiazole, 1,3,4-oxadiazole; and also in an alternative embodiment, isothiazole, 1,2,5-thiadiazole, 1,2,4-thiadiazole or 1,2,3-thiadiazole.

In another aspect, HET is selected from the formulae (HET1) to (HET3) below:—

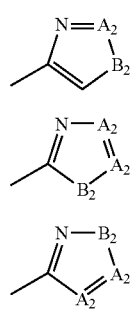

(HET1)

(HET2)

(HET3)

wherein $A_2$ is carbon or nitrogen and $B_2$ is O, S or N (with a maximum of 3 hetero atoms per ring), with carbon or nitrogen ring atoms being optionally substituted as described for HET hereinbefore (preferably with no substitution on any carbon atom that is adjacent to the specified N atom).

The above HET definitions are especially preferred in embodiment (IP).

Especially preferred compounds of the present invention are of the formula (IB):

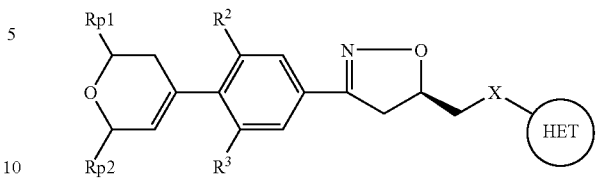

(IB)

wherein HET is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl;

X is O, S or NH (especially NH);

$R^2$ and $R^3$ are independently hydrogen or fluoro; and Rp1 and Rp2 are independently hydrogen, hydroxy, bromo, (1–4C)alkyl, carboxy, (1–4C)alkoxycarbonyl, hydroxymethyl, (1–4C)alkoxymethyl or carbamoyl; or pharmaceutically-acceptable salts thereof.

Further especially preferred compounds of the invention are of the formula (IB) wherein HET is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl; $R^2$ and $R^3$ are independently hydrogen or fluoro; and Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene); or pharmaceutically-acceptable salts thereof.

Of the above especially preferred compounds of the invention of the formula (IB), particularly preferred compounds are those wherein Rp1 and Rp2 are hydrogen are particularly preferred.

Further, especially preferred compounds of the invention are of the formula (IC):

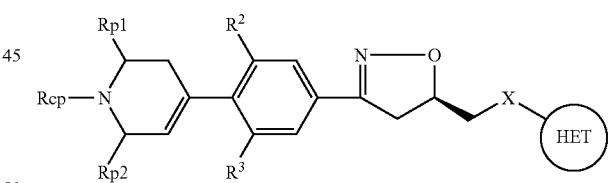

(IC)

wherein HET is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl; $R^2$ and $R^3$ are independently hydrogen or fluoro; X is O, S or NH (paticularly O and NH, especially NH);

Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene), (1–4C)alkyl, carboxy, (1–4C) alkoxycarbonyl, hydroxymethyl, (1–4C)alkoxymethyl or carbamoyl and Rcp is cyano, pyrimidin-2-yl, 2-cyanoethenyl, 2-cyano-2-((1–4C)alkyl)ethenyl or Rcp is of the formula $R^{10p}CO$—, $R^{10p}SO_2$— or $R^{10p}CS$— (wherein $R^{10p}$ is hydrogen, (1–5C)alkyl [optionally substituted by one or more groups each independently selected from hydroxy and amino, or optionally monosubstituted by (1–4C)alkoxy, (1–4C)alkylS(O)$_q$—, (1–4C)alkylamino, (1–4C)alkanoyl, naphthoxy, (2–6C)alkanoylamino or (1–4C)alkylS(O)$_p$NH— wherein p is 1 or 2 and q is 0, 1 or 2], imidazole, triazole, pyrimidine, pyridazine, pyridine, isoxazole, oxazole, isothiazole, thiazole, pyridoimidazole, pyrimidoimidazole, quinoxaline, quinazoline, phthalazine, cinnoline or naphthyridine, or R$^{10p}$ is of the formula R$^{11p}$C(O)O(1–6C)alkyl wherein R$^{11p}$ is (1–6C)alkyl), or Rcp is of the formula RfC(═O)C(═O)— wherein Rf is (1–6C)alkoxy; or pharmaceutically-acceptable salts thereof.

Of the above especially preferred compounds of the invention of the formula (IC), those wherein HET is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl; R$^2$ and R$^3$ are independently hydrogen or fluoro; Rp1 and Rp2 are independently hydrogen, AR-oxymethyl or AR-thiomethyl (wherein AR is phenyl, phenyl-(1–4C)alkyl, naphthyl, furan, pyrrole, pyrazole, imidazole, triazole, pyrimidine, pyridazine, pyridine, isoxazole, oxazole, isothiazole, thiazole or thiophene), (1–4C)alkyl, carboxy, (1–4C)alkoxycarbonyl, hydroxymethyl, (1–4C)alkoxymethyl or carbamoyl and Rcp is cyano, pyrimidin-2-yl, 2-cyanoethenyl, 2-cyano-2-((1 4C)alkyl)ethenyl or Rcp is of the formula R$^{10p}$CO—, R$^{10p}$SO$_2$— or R$^{10p}$CS— (wherein R$^{10p}$ is hydrogen, (1–5C) alkyl [optionally substituted by one or more groups each independently selected from hydroxy and amino, or optionally monosubstituted by (1–4C)alkoxy, (1–4C)alkylS(O)$_q$, (1–4C)alkylamino, (1–4C)alkanoyl, (2–6C)alkanoylamino or (1–4C)alkylS(O)$_p$NH— wherein p is 1 or 2 and q is 0, 1 or 2], pyridine, or R$^{10p}$ is of the formula R$^{11p}$C(O)O(1–6C) alkyl wherein R$^{11p}$ is (1–6C)alkyl), or Rcp is of the formula RfC(═O)C(═O)— wherein Rf is (1–6C)alkoxy; or pharmaceutically-acceptable salts thereof are further preferred.

Of the above especially preferred compounds of the invention of the formula (IC), particularly preferred compounds are those wherein HET is isoxazol-3-yl, isoxazol-5-yl, 1,2,4oxadiazol-3-yl, isothiazol-3-yl, 1,2,4-thiadiazol-3-yl or 1,2,5-thiadiazol-3-yl; R$^2$ and R$^3$ are independently hydrogen or fluoro; Rp1 and Rp2 are hydrogen, and Rep is pyridin-2-yl (optionally substituted with cyano) or Rcp is of the formula R$^{10p}$CO— (wherein R$^{10p}$ is hydrogen, 1,3-dioxolan-4-yl (optionally disubstituted with (1–4C)alkyl) or (1–5C)alkyl [optionally substituted by one or more hydroxy groups] or R$^{10p}$ is of the formula R$^{11p}$C(O)O(1–6C)alkyl wherein R$^{11p}$ is (1–6C)alkyl)); or pharmaceutically-acceptable salts thereof.

Of the above especially preferred compounds of the invention of the formula (IC), particularly preferred compounds are those wherein Rcp is of the formula R$^{10p}$CO— (wherein R$^{10p}$ is hydrogen, 1,3-dioxolan-4-yl (optionally disubstituted with (1–4C)alkyl) or (1–5C)alkyl [substituted by two hydroxy groups]; or pharmaceutically-acceptable salts thereof.

In another aspect of the invention particularly preferred compounds of the invention are of the formula (IC) wherein HET is isoxazol-3-yl; R$^2$ and R$^3$ are independently hydrogen or fluoro; Rp1 and Rp2 are hydrogen and Rcp is R$^{10p}$CO— (wherein R$^{10p}$ is hydrogen, (1–5C)alkyl [optionally substituted by one or two hydroxy groups], or R$^{10p}$ is of the formula R$^{11p}$C(O)O(1–6C)alkyl (wherein R$^{11p}$ is (1–6C)alkyl)); and pharmaceutically-acceptable salts thereof.

In another aspect of the invention all of the compounds of formula (IB) or (IC) described above are further preferred when HET is isoxazol-3-yl, isothiazol-3-yl or 1,2,5-thiadiazol-3-yl.

In yet another aspect the invention relates to all of the compounds of formula (IB) or (IC) described above wherein HET is isoxazol-3-yl or 1,2,4-oxadiazol-3-yl.

In yet another aspect the invention relates to all of the compounds of formula (IB) or (IC) described above wherein HET is isoxazol-3-yl.

In another aspect of the invention there are provided preferred compounds of the formula (IP) wherein HET is isoxazol-3-yl, 1,2,4-oxadiazol-3-yl, isothiazol-3-yl, 1,2,5-thiadiazol-3-yl; >A—B— is >N—CH$_2$— and D is NR$^{7p}$ (or D is O) wherein Rcp is a 6-membered heteroaryl ring containing 1, 2 or 3 ring nitrogen atoms as the only ring heteroatoms, linked via a ring carbon atom and optionally substituted on a ring carbon atom by one, two or three substituents independently selected from (1–4C)alkyl, halo, trifluoromethyl, (1–4C)alkyl S(O)$_q$, (wherein q is 0, 1 or 2), (1–4C)alkylS(O)$_2$amino, (1–4C)alkanoylamino, carboxy, hydroxy, amino, (1–4C)alkylamino, di-(1–4C)alkylamino, (1–4C)alkoxycarbonyl, carbamoyl, N-(1–4C)alkylcarbamoyl, di-(N-(1–4C)alkyl)carbamoyl, (1–4C)alkoxy, cyano or nitro; or pharmaceutically-acceptable salts thereof.

In all of the above aspects and preferred compounds of formula (IB) or (IC), in-vivo hydrolysable esters are preferred where appropriate, especially phosphoryl esters (as defined by formula (PD3) with npd as 1).

In all of the above definitions the preferred compounds are as shown in formula (IA), i.e. the pharmaceutically active (5(R)) enantiomer.

Particular compounds of the present invention include the following:—

(5RS)-3-(4-(1-Hydroxyacetyl-1,2,5,6-tetrahydropyrid-4-yl)phenyl)-5-(3-isoxazolylamino-methyl)-4,5-dihydro-isoxazole and (5RS)-3-(4-((2S)-2,3-Dihydroxypropanoyl- 1,2,5,6-tetrahydropyrid-4-yl)phenyl)-5-(3-isoxazolylaminomethyl)-4,5-dihydro-isoxazole and the individual (5R) isomers thereof; and in-vivo-hydrolysable esters thereof.

Other particular compounds of the present invention include the following:—

(5RS)-3-(4-((2S)-2,3-Dihydroxypropyl-1,2,5,6-tetrahydropyrid-4-yl)phenyl)-5-isoxazol-3-yl-oxymethyl-4,5-dihydroisoxazole;

(5RS)-3-(3-Fluoro-4-(4-((2S)-2,3-dihydroxypropionyl)piperazin-1-yl)phenyl)-5-isoxazol-3-yl-oxymethyl-4,5-dihydroisoxazole;

(5RS)-3-(3-Fluoro-4-morpholin-4-yl phenyl)-5-isoxazol-3-ylaminomethyl-4,5-dihydroisoxazole;

(5RS)-3-(3-Fluoro-4-(1-oxothiomorpholin-4-yl)phenyl)-5-isoxazol-3-ylaminomethyl-4,5-dihydroisoxazole;

(5RS)-3-(3-fluoro-4-(1,1-dioxothiomorpholin-4-yl)phenyl)-5-isoxazol-3-ylaminomethyl-4,5-dihydroisoxazole;

(5RS)-3-(3-Fluoro-4-piperazin-1-ylphenyl)-5-isoxazol-3-ylaminomethyl-4,5-dihydroisoxazole;

(5RS)-3-(3-Fluoro-4-(4-methanesulfonyl)piperazin-1-ylphenyl)-5-isoxazol-3-ylaminomethyl-4,5-dihydroisoxazole;

and the individual (5R) isomers thereof; and pharmaceutically-acceptable salts or in-vivo hydrolysable esters thereof.

Further particular compounds of the present invention include the following:—

(5RS)-3-(3-Fluoro-4-imidazol-1-ylphenyl)-5-isoxazol-3-ylaminomethyl-4,5-dihydroisoxazole;

(5RS)-3-(3-Fluoro-4-imidazol-1-ylphenyl)-5-isoxazol-3-yloxymethyl-4,5-dihydroisoxazole;

and the individual (SR) isomers thereof; and pharmaceutically-acceptable salts thereof.

Process Section:

In a further aspect the present invention provides a process for preparing a compound of formula (I) or a pharmaceutically-acceptable salt or an in-vivo hydrolysable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons).

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A compound of the formula (I), or a pharmaceutically-acceptable salt or an in vivo hydrolysable ester thereof, may be prepared by any process known to be applicable to the preparation of chemically-related compounds. Such processes, when used to prepare a compound of the formula (I), or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples (in which, for example, 3,5-difluorophenyl, 3-fluorophenyl and (des-fluoro)phenyl containing intermediates may all be prepared by analagous procedures; or by alternative procedures—for example, the preparation of (T group)-(fluoro) phenyl intermediates by reaction of a (fluoro)phenylstannane with, for example, a pyran or (tetrahydro)pyridine compound, may also be prepared by anion chemistry (see, for example, WO97/30995). Alternatively, necessary starting materials are obtainable by analogous procedures to those illustrated which are within the ordinary skill of an organic chemist.

Information on the preparation of necessary starting materials or related compounds (which may be adapted to form necessary starting materials) may also be found in the following Patent and Application Publications, the contents of the relevant process sections of which are hereby incorporated herein by reference: WO 98/07708, WO 98/54161, WO 99/41244 and WO 99/43671.

The skilled organic chemist will be able to use and adapt the information contained and referenced within the above references to obtain necessary starting materials.

Thus, the present invention also provides that the compounds of the formulae (I) and pharmaceutically-acceptable salts and in vivo hydrolysable esters thereof, can be prepared by a process (a) to (c) as follows (wherein the variables are as defined above unless otherwise stated):

(wherein the variables are as defined above unless otherwise stated):

(a) by modifying a substituent in or introducing a substituent into another compound of formula (I);

(b) by reaction of a compound of formula (II):

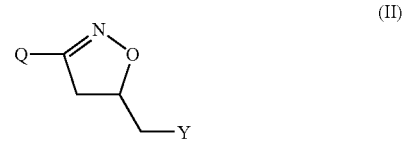

wherein Y is either (i) hydroxy; or (ii) a displaceable group with a compound of the formula (III):

HN(Pg)-HET or HX-HET (III-A) (III-B)

wherein Pg is a suitable protecting group; or (c) by reaction of a compound of formula (II) wherein Y is an amino group with a compound of the formula (IV):

Lg-HET (IV)

wherein Lg is a leaving group; and thereafter if necessary:

(i) removing any protecting groups; (ii) forming a pharmaceutically-acceptable salt; (iii) forming an in-vivo hydrolysable ester.

Deprotection, salt formation or in-vivo hydrolysable ester formation may each be provided as a specific final process step.

Where Y is a displaceable group, suitable values for Y are for example, a halogeno or sulfonyloxy group, for example a chloro, bromo, methanesulfonyloxy or toluene-4-sulfonyloxy group.

General guidance on reaction conditions and reagents may be obtained in Advanced Organic Chemistry, 4$^{th}$ Edition, Jerry March (publisher: J. Wiley & Sons), 1992. Necessary starting materials may be obtained by standard procedures of organic chemistry, such as described in this process section, in the Examples section or by analogous procedures within the ordinary skill of an organic chemist. Certain references are also provided which describe the preparation of certain suitable starting materials, the contents of which are incorporated here by reference. Processes analogous to those described in the references may also be used by the ordinary organic chemist to obtain necessary starting materials.

(a) Methods for converting substituents into other substituents are known in the art. For example an alkylthio group may be oxidised to an alkylsulfinyl or alkysulfonyl group, a cyano group reduced to an amino group, a nitro group reduced to an amino group, a hydroxy group alkylated to a methoxy group, a hydroxy group thiomethylated to an arylthiomethyl or a heteroarylthiomethyl group (see, for example, Tet. Lett., 585, 1972), a carbonyl group converted to a thiocarbonyl group (eg. using Lawsson's reagent) or a bromo group converted to an alkylthio group. It is also possible to convert one Rc group into another Rc group as a final step in the preparation of a compound of the formula (I), for example, acylation of a group of formula (TC5) wherein Rc is hydrogen.

Such modifications also permit the formation of compounds in which X is SO or SO$_2$ from compounds in which X is S, by use of a suitable oxidising agent, using standard conditions.

(b)(i) Reaction (b)(i) is performed under Mitsunobu conditions, for example, in the presence of tri-n-butylphosphine and diethyl azodicarboxylate (DEAD) in an organic solvent such as THF, and in the temperature range 0° C.–60° C., but preferably at ambient temperature. Details of Mitsunobu reactions are contained in Tet. Letts., 31, 699, (1990); The Mitsunobu Reaction, D. L. Hughes, Organic Reactions, 1992, Vol. 42, 335–656 and Progress in the Mitsunobu Reaction, D. L. Hughes, Organic Preparations and Procedures International, 1996, Vol. 28, 127–164.

Particularly suitable values for Pg are the following, or suitable derivatives thereof; Pg such as to give a carbamate (for example Pg as t-BOC or 2,2,2-trichloroethyloxycarbonyl), Pg as (1–4C)alkanoyl (for example acxetyl or chloroacetyl), phosphoramidate, allyloxy, benzyloxy (and methyl/nitro derivatives thereof) or sulfonyl (such as, for example, tosylate, mesylate, 4nitrophenylsulfonyl, 4-methoxy-2,3,6-trimethyl-phenylsulfonyl). See the accompanying Examples for particular values of Pg.

Pg may be removed by techniques available to the skilled chemist (see also techniques described elsewhere herein). For example, tosylate and mesylate may be removed using standard deprotection conditions, or Na/Li amalgam or Mg/MeOH under standard conditions; 4-nitrophenylsulfonyl may be removed using base and phenylthio or thioacetic acid; 4-methoxy-2,3,6-trimethyl-phenylsulfonyl may be removed using TFA deprotection under standard conditions.

Compounds of the formula (II) wherein Y is hydroxy may be obtained as described in the references cited herein (particularly in the section proceeding the discussion of protecting groups), or obtained by adapting the chemistry described therein.

If not commercially available, compounds of the formula (III) may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl, Methoden der Organische Chemie, E8a, Pt. I (1993), 45–225, B. J. Wakefield. Many amino-HET compounds are commercially available and may be converted into HN(Pg)-HET by standard techniques.

(b)(ii) Reactions (b)(ii) are performed conveniently in the presence of a suitable base such as, for example, an alkali or alkaline earth metal carbonate, alkoxide or hydroxide, for example sodium carbonate or potassium carbonate, or, for example, an organic amine base such as, for example, pyridine, 2,6-lutidine, collidine, 4-dimethylaminopyridine, triethylamine, morpholine or diazabicyclo-[5.4.0]undec-7-ene, the reaction is also preferably carried out in a suitable inert solvent or diluent, for example methylene chloride, acetonitrile, tetrahydrofuran, 1,2-dimethoxyethane, N,N-dimethylformamide, N,N-dimethylacetamide, N-methylpyrrolidin-2-one or dimethylsulfoxide at and at a temperature in the range 25–60° C.

When Y is chloro, the compound of the formula (II) may be formed by reacting a compound of the formula (II) wherein Y is hydroxy (hydroxy compound) with a chlorinating agent. For example, by reacting the hydroxy compound with thionyl chloride, in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature. A compound of the formula (II) wherein Y is chloro or iodo may also be prepared from a compound of the formula (II) wherein Y is mesylate or tosylate, by reacting the latter compound with lithium chloride or lithium iodide and crown ether, in a suitable organic solvent such as THF, in a temperature range of ambient temperature to reflux.

When Y is (1–4C)alkanesulfonyloxy or tosylate the compound (II) may be prepared by reacting the hydroxy compound with (1–4C)alkanesulfonyl chloride or tosyl chloride in the presence of a mild base such as triethylamine or pyridine.

When Y is a phosphoryl ester (such as PhO$_2$—P(O)—O—) or Ph$_2$—P(O)—O— the compound (II) may be prepared from the hydroxy compound under standard conditions.

(c) The skilled man will appreciate that for the reaction of a compound of formula (II) wherein Y is an amino group with a compound of the formula (IV), Lg-HET, certain, reactive heteroarlys HET react satisfactorily, such as triazines and pyridazine. A suitable value for Lg is chloro. The reaction is performed under standard conditions in an inert solvent and in the presence of a suitable base (such as triethylamine).

Compounds of the formula (II) wherein Y is amino may be obtained as described in the references cited herein (particularly in the section proceeding the discussion of protecting groups), for example from the corresponding compounds in which Y is hydroxy (via the azide).

The following Schemes illustrate process chemistry which allows preparation of compounds of the formula (I). The Schemes may be genericised by the skilled man to apply to compounds within the present specification which are not specifically illustrated in the Schemes.

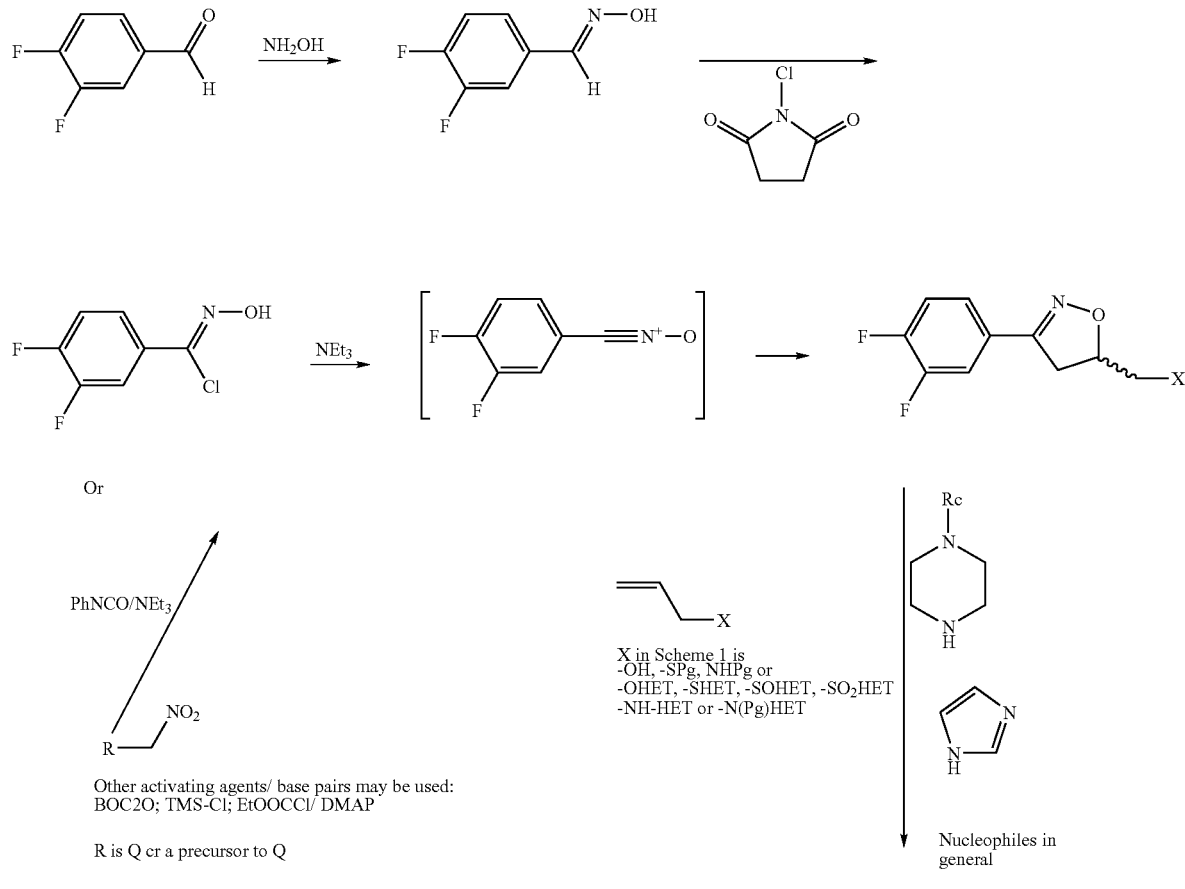

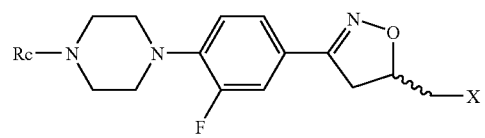

Routes to Isoxazolines Scheme 2

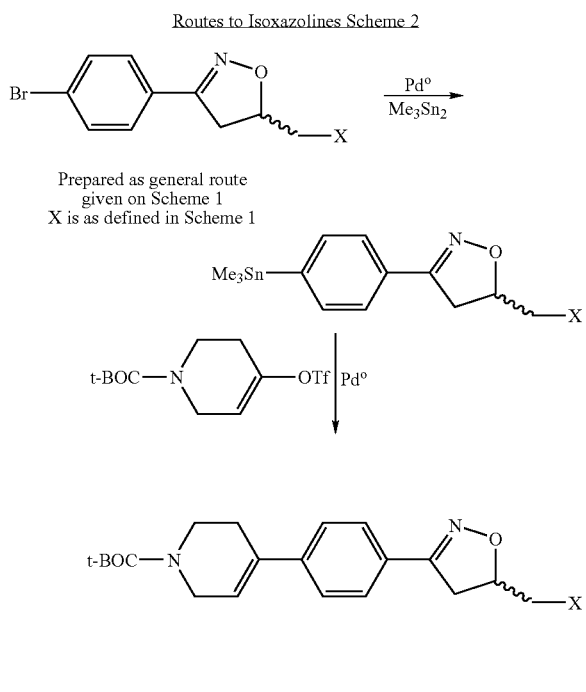

Prepared as general route given on Scheme 1
X is as defined in Scheme 1

Other carbon linked species can be made analogously

In Schemes 1 and 2 when X is -OH, such intermediates may be converted to (e.g.) mesylate and then reacted with (e.g.) HET-OH, HET-SH or HET-NH(Pg).

The removal of any protecting groups, the formation of a pharmaceutically-acceptable salt and/or the formation of an in vivo hydrolysable ester are within the skill of an ordinary organic chemist using standard techniques. Furthermore, details on the these steps, for example the preparation of in-vivo hydrolysable ester prodrugs has been provided in the section above on such esters, and in certain of the following non-limiting Examples.

When an optically active form of a compound of the formula (I) is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the formula (I) is required, it may be obtained by carrying out one of the above procedures using a pure regioisomer as a starting material, or by resolution of a mixture of the regioisomers or intermediates using a standard procedure.

According to a further feature of the invention there is provided a compound of the formula (I), or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the formula (I), or a pharmaceutically-acceptable salt, or in-vivo hydrolysable ester thereof, for use as a medicament; and the use of a compound of the formula (I) of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the formula (I), an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I), an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, aerosols (or sprays), drops and sterile injectable aqueous or oily solutions or suspensions.

In addition to the compounds of the present invention the pharmaceutical composition of this invention may also contain or be co-administered (simultaneously, sequentially or separately) with one or more known drugs selected from other clinically useful antibacterial agents (for example, β-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg. In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 mgkg$^{-1}$ to 20 mgkg$^{-1}$ of a compound of this invention, the composition being administered 1 to 4 times per day. In another embodiment a daily dose of 5 mgkg$^{-1}$ to 20 mgkg$^{-1}$ of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

A pharmaceutical composition to be dosed intravenously may contain advantageously (for example to enhance stability) a suitable bactericide, antioxidant or reducing agent, or a suitable sequestering agent.

In the above other, pharmaceutical composition, process, method, use and medicament manufacture features, the alternative and preferred embodiments of the compounds of the invention described herein also apply.

Antibacterial Activity

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of S. aureus and coagulase negative staphylococci. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) determined by the agar-dilution technique with an inoculum size of $10^4$ CFU/spot. Typically, compounds are active in the range 0.01 to 256 μg/ml.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms.

For example, the following results were obtained for the compound of Example 1:

| Organism | MIC (μg/ml) |
| --- | --- |
| Staphylococcus aureus: | |
| Oxford | 2 |
| Novb. Res | 4 |
| MRQR | 4 |
| Coagulase Negative Staphylococci | |
| MS | 1 |
| MR | 2 |

-continued

| Organism | MIC (μg/ml) |
| --- | --- |
| Streptococcus pyogenes | |
| C203 | 8 |
| Enterococcus faecalis | 8 |
| Bacillus subtilis | 1 |

Novb. Res = Novobiocin resistant
MRQR = methicillin resistant quinolone resistant
MR = methicillin resistant
MS = methicillin sensitive Certain intermediates and/or Reference Examples described hereinafter (especially those in which the —NH— link to HET is protected by a BOC group) may also possess useful activity, and are provided as a further feature of the invention.

The invention is now illustrated but not limited by the following Examples in which unless otherwise stated:—

(i) evaporations were carried out by rotary evaporation in vacuo and work-up procedures were carried out after removal of residual solids by filtration;

(ii) operations were carried out at ambient temperature, that is typically in the range 18–26° C. and in air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the formula (I) were generally confirmed by NMR and mass spectral techniques [proton magnetic resonance spectra were generally determined in DMSO-D6 unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus: s, singlet; d, doublet; AB or dd, doublet of doublets; t, triplet, m, multiplet; fast-atom bombardment (FAB) mass spectral data were generally obtained using a Platform spectrometer (supplied by Micromass) run in electrospray and, where appropriate, either positive ion data or negative ion data were collected];

(vi) intermediates were not generally fully characterised and purity was in general assessed by thin layer chromatographic, infra-red (IR), mass spectral (MS) or NMR analysis; and (vii) in which the following abbreviations may be used:—

® is a Trademark; DMF is N,N-dimethylformamide; DMA is N,N-dimethylacetamide;

TLC is thin layer chromatography; HPLC is high pressure liquid chromatography;

MPLC is medium pressure liquid chromatography; DMSO is dimethylsulfoxide;

CDCl$_3$ is deuterated chloroform; MS is mass spectroscopy; ESP is electrospray;

THF is tetrahydrofuran; TFA is trifluoroacetic acid; NMP is N-methylpyrrolidone;

HOBT is 1-hydroxy-benzotriazole; EtOAc is ethyl acetate; MeOH is methanol;

phosphoryl is $(HO)_2$—P(O)—O—; phosphiryl is $(HO)_2$—P—O—; EDC is 1-(3-dimethylaminopropyl)-3-ethylcarbodiimide (hydrochloride); PTSA is para-toluenesulfonic acid.

EXAMPLE 1

(5RS)-3-(4-(1-Hydroxyacetyl-1,2,5,6-tetrahydropyrid-4-yl)phenyl)-5-(3-isoxazolylaminomethyl)-4,5-dihydro-isoxazole (5RS)-3-(4-(1,2,5,6-Tetrahydropyrid-4-yl)phenyl)-5-(3-isoxazolylaminomethyl)-4,5-dihydroisoxazole dihydrochloride (397 mg, 1 mM) was suspended in acetonitrile (15 ml) under nitrogen, triethylamine (404 mg, 4 mM) added, and the mixture cooled to 0° C. Acetoxyacetyl chloride (170 mg, 1.25 mM) was added dropwise with stirring, and stirring continued for 4 hours, allowing the temperature to rise to ambient. Solvent was evaporated, the residue treated with water (20 ml) and extracted into dichloromethane (3×20 ml). The extracts were dried (magnesium sulfate), evaporated, the residue dissolved in methanol (15 ml), and stirred 18 hours at ambient temperature with potassium carbonate (138 mg, 1 mM). After removal of solvent, the residue was chromatographed on a 10 g silica Mega Bond Elut® column, eluting with 5% methanol in dichloromethane. Relevant fractions were combined to give the desired product (205 mg). MS (ESP): 383 (MH$^+$) for $C_{20}H_{22}N_4O_4$ NMR (CDCl$_3$) δ: 2.58 (br, 2H); 3.18 (dd, 1H); 3.44 (dd, 1H); 3.49 (m, 2H); 3.61 (overlapping m, 2H); 3.90 (t, 1H); 3.97 (m, 1H); 4.16 (dd, 1H); 4.27 (dd, 1H); 4.30 (m, 2H); 5.02 (m, 1H); 5.83 (d, 1H); 6.11 (2×m, 1H); 7.39 (m, 2H); 7.63 (d, 2H); 8.03 (d, 1H).

The intermediates for this compound were prepared as follows:—

3-(t-Butoxycarbonylamino)isoxazole

3-Aminoisoxazole (10 g, 0.12 M) and 4-dimethylaminopyridine (500 mg, 4.1 mM) were dissolved in pyridine (200 ml), and treated in portions with di-t-butyl dicarbonate (51.94 g, 0.24 M). The mixture was stirred at ambient temperature for 18 hours, then evaporated to dryness. The residue was dissolved in methanol (200 ml) and treated with sodium hydroxide solution (2N, 60 ml), then stirred for 2 hours. After acidification with aqueous citric acid (10%, 160 ml), the mixture was added to water (750 ml), and the desired product (15.9 g) collected by filtration.

NMR(DMSO-d$_6$) δ: 1.46 (s, 9H); 6.69 (d, 1H); 8.68 (d, 1H); 10.27 (s, 1H).

N-Allyl-3-(t-Butoxycarbonylamino)isoxazole 3-(t-Butoxycarbonylamino)isoxazole (12 g, 65.2 mM) was dissolved in dimethoxyethane (150 ml) and cooled to 0° C. under nitrogen. To the stirred solution was added sodium hydride (60% in oil, 2.87 g, 71.7 mM), and the mixture stirred 20 minutes. Allyl bromide (8.7 g, 71.7 mM) was added dropwise, and the mixture stirred at ambient temperature for 18 hours, then diluted with water (300 ml), and extracted into diethyl ether (3×100 ml). The extracts were washed with brine (100 ml), dried (magnesium sulfate), and chromatographed on silica (50 g) eluting with dichloromethane. Relevant fractions were combined to give the desired product as an oil (14.68 g). MS (ESP): 225 (MH$^+$) for $C_{11}H_{16}N_2O_3$ NMR(CDCl$_3$) δ: 1.54 (s, 9H); 4.47 (dm, 2H); 5.18 (m, 2H); 5.92 (m, 1H); 6.87 (d, 1H); 8.22 (d, 1H).

(5RS)-3-(4-Bromophenyl)-5-(3-N-(t-butoxycarbonyl)isoxazolylaminomethyl)-4,5-dihydroisoxazole N-Allyl-3-(t-butoxycarbonylamino)isoxazole (4.48 g, 20 mM) and 4-bromo-N-hydroxybenzenecarboximidoyl chloride (4.92 g, 20 mM, see WO 98/07708) were dissolved in anhydrous diethyl ether (50 ml), and stirred vigorously at ambient temperature under nitrogen during the addition of triethylamine (2.63 g, 26 mM). Stirring was continued for 18 hours, the mixture diluted with ethyl acetate (100 ml), and washed successively with water (150 ml) and brine (3×100 ml). The organic layer was dried (magnesium sulfate), filtered, and evaporated to dryness. The resulting solid was triturated with diethyl ether/isohexane (1:1, 100 ml), and filtered to give the desired product (5.76 g). MS (ESP): 422 (MH$^+$) for $C_{18}H_{20}BrN_3O_4$ NMR (CDCl$_3$) δ: 1.53 (s, 9H); 3.16 (dd, 1H); 3.37 (dd, 1H); 3.97 (dd, 1H); 4.20 (dd, 1H); 5.19 (m, 1H); 6.89 (d, 1H); 7.52 (s, 4H); 8.23 (d, 1H).

(5RS)-3-(4-Trimethylstannylphenyl)-4,5-dihydro-5-(3-N-(t-butoxycarbonyl)isoxazolylaminomethyl)-4,5-dihydroisoxazole (5RS)-3-(4-Bromophenyl)-5-(3-N-(t-butoxycarbonyl)isoxazolylaminomethyl)-4,5-dihydroisoxazole (5.86 g, 13.9 mM) and dichlorobis(triphenylphosphinc)palladium(II) (488 mg, 0.7 mM) were dissolved in 1,4-dioxane (60 ml, deoxygenated by nitrogen). To this was added hexamethylditin (5 g, 15.3 mM) in 1,4-dioxane (20 ml), and the resulting mixture heated at 100° C. for 24 hours. After cooling and filtering through celite, the solvent was evaporated, and the residual oil chromatographed on a 90 g Biotage silica column, eluting with a mixture of ethyl acetate/isohexane (3:1). Relevant fractions were combined to give the desired product as an oil (5.93 g).

NMR (CDCl$_3$) δ: 1.31 (s, 9H); 1.54 (s, 9H); 3.16 (dd, 1H); 3.39 (dd, 1H); 3.97 (dd, 1H); 4.19 (dd, 1H); 5.16 (m, 1H); 6.89 (d, 1H); 7.53 (d, 2H); 7.62 (d, 2H); 8.23 (d, 1H).

(5RS)-3-(4-(1-t-Butoxycarbonyl-1,2,5,6-tetrahydropyrid-4-yl)phenyl)-5-(3-N-(t-butoxycarbonyl)isoxazolylaminomethyl)-4,5-dihydro-isoxazole Tris(dibenzylideneacetone)dipalladium (24 mg, 0.026 mM) and triphenylarsine (3 mg, 0.01 mM) were dissolved in degassed N-methylpyrrolidone (15 ml) under nitrogen. (5RS)-3-(4-Trimethylstannylphenyl)-4,5-dihydro-5-(3-N-(t-butoxycarbonyl)isoxazolylaminomethyl )4,5-dihydroisoxazole (586 mg, 1.16 mM) and 1-t-butoxycarbonyl-trifluorosulfonyloxy-1,2,5,6-tetrahydropyridine (WO97/30995; Synthesis, 993, (1991); 358 mg, 1.08 mM) were added, and the reaction stirred at ambient temperature for 18 hours. The mixture was diluted with water (50 ml), extracted with ethyl acetate (3×25 ml), the organic extracts washed with brine (25 ml) and dried (magnesium sulfate). The residue after evaporation was chromatographed on a 10 g silica Mega Bond Elut® column, eluting with a mixture of ethyl acetate/isohexane (3:1). Relevant fractions were combined to give the desired product (320 mg).

NMR (CDCl$_3$) δ: 1.49 (s, 9H); 1.53 (s, 9H); 2.53 (br, 2H); 3.16 (dd, 1H); 3.39 (dd, 1H); 3.63 (t, 2H); 3.98 (dd, 1H); 4.09 (m, 2H); 4.20 (dd, 1H); 5.17 (m, 1H); 6.11 (br, 1H); 6.90 (br, 1H); 7.40 (d, 2H); 7.63 (d, 2H); 8.23 (d, 1H).

(5RS)-3-(4-(1,2,5,6-Tetrahydropyrid-4-yl)phenyl)-5-(3-isoxazolylaminomethyl)-4,5-dihydroisoxazole dihydrochloride (5RS)-3-(4-(1-t-Butoxycarbonyl-1,2,5,6-tetrahydropyrid-4-yl)phenyl)-5-(3-N-(t-butoxycarbonyl)isoxazolylaminomethyl)-4,5-dihydroisoxazole (2.46 g, 4.7 mM) was dissolved in ethanol (20 ml), cooled to 0° C. under nitrogen, and treated with ethanolic hydrogen chloride (4M, 20 ml). The mixture was stirred at ambient temperature for 18 hours, the volume reduced to 15 ml, then diethyl ether added until turbid. The desired product crystallised on standing (1.42 g). MS (ESP): 325 (MH$^+$) for C$_{18}$H$_{20}$N$_4$O$_2$
NMR (DMSO-d$_6$) δ: 2.68 (br, 2H); 3.20 (m overlapping dd, 5H); 3.46 (dd, 1H); 3.69 (br, 2H); 4.87 (m, 1H); 5.97 (d, 1H); 6.26 (m, 1H); 7.53 (d, 2H); 7.64 (d, 2H); 8.34 (d, 1H); 9.45 (br, 2H).

EXAMPLE 2

(5RS)-3-(4-((2S)-2,3-Dihydroxypropanoyl-1,2,5,6-tetrahydropyrid-4-yl)phenyl)-5-(3-isoxazolylaminomethyl)4,5-dihydro-isoxazole (5RS)-3-(4-(1,2,5,6-Tetrahydropyrid-4-yl)phenyl)-5-(3-isoxazolylaminomethyl)-4,5-dihydro-isoxazole dihydrochloride (397 mg, 1 mM) was suspended by stirring in acetonitrile (15 ml) under nitrogen, triethylamine (404 mg, 4 mM) added, and the mixture cooled to 0° C. (4S)-2,2-Dimethyl-1,3-dioxolan-4-ylcarbonyl chloride (328 mg, 2 mM) was added dropwise, stirring continued for 30 minutes at 0° C., then for 18 hours allowing the temperature to rise to ambient. Solvent was evaporated, the residue treated with water (25 ml) and extracted into dichloromethane (4×20 ml). The extracts were washed with brine (25 ml), dried (magnesium sulfate), and evaporated. The residue was dissolved in tetrahydrofuran (40 ml), treated with hydrochloric acid (2N, 2 ml), and stirred 48 hours at ambient temperature. Potassium carbonate (2 g) was added, the mixture stirred 30 minutes and filtered. After removal of solvent, the residue was chromatographed on a 10 g silica Mega Bond Elut® column, eluting with a gradient from 5 to 10% methanol in dichloromethane. Relevant fractions were combined to give the desired product (125 mg). MS (ESP): 413 (MH$^+$) for C$_{21}$H$_{24}$N$_4$O$_5$ NMR (CDCl$_3$) δ: 2.54 (br, 2H); 3.18 (dd, 1H); 3.26 (m overlapped by H$_2$O, 2H); 3.47 (dd, 2H); 3.55 (m, 1H); 3.74 (m, 2H); 4.13 (br, 1H); 4.26 (m, 1H); 4.38 (m, 1H); 4.67 (d, 1H); 4.89 (overlapping m, 2H); 5.96 (d, 1H); 6.26 (br, 1H); 6.37 (t, 1H); 7.50 (d, 2H); 7.62 (d, 2H); 8.34 (d, 1H).

EXAMPLE 3

(5RS)-3-(4-((2S)-2.3-Dihydroxypropyl-1.2.5.6-tetrahydropyrid-4-yl)phenyl)-5-isoxazol-3-yloxymethyl-4,5-dihydroisoxazole (5RS)-3-(4-(1,2,5,6-Tetrahydropyrid-4-yl)phenyl)-5-isoxazol-3-yloxymethyl-4,5-dihydro-isoxazole hydrochloride (300 mg, 0.83 mM) was treated with (4S)-2,2-dimethyl-1,3-dioxolan-4-ylcarbonyl chloride under essentially the conditions of Example 2. Crude product was chromatographed on a 20 g silica Mega Bond Elut® column, eluting with 5% methanol in dichloromethane. Relevant fractions were combined to give the desired product (43 mg).
MS (ESP): 414 (MH$^+$) for C$_{21}$H$_{23}$N$_3$O$_6$
NMR (CDCl$^3$) δ: 2.64 (br, 2H); 3.27 (dd, 1H); 3.50 (dd, 1H); 3.72 (m, 3H); 3.80–4.18 (overlapping m, 4H); 4.30 (m, 1H); 4.42 (d, 2H); 4.53 (m, 1H); 5.13 (m, 1H); 5.99 (d, 1H); 6.13 (br, 1H); 7.40 (d, 2H); 7.65 (d, 2H); 8.11 (d, 1H).

The intermediates for this compound were prepared as follows:—
The intermediates for this compound were prepared as follows:—

(5RS)-3-(4-Bromophenyl)-5-hydroxymethyl-4.5-dihydro-isoxazole

Allyl alcohol (1.16 g, 20 mM) and 4-bromobenzohydroximinoyl chloride (4.92 g, 20 mM, see WO 98-07708) were reacted using essentially the procedure of the equivalent intermediate of Example 1, to give the desired product (3.33 g).
NMR(CDCl$_3$) δ: 2.11 (br, 1H); 3.25 (dd, 1H); 3.35 (dd, 1H); 3.68 (br d, 1H); 3.88 (br d, 1H); 4.87 (m, 1H); 7.52 (s, 4H).

(5RS)-3-(4-Bromophenyl)-5-isoxazol-3-yloxymethyl-4,5-dihydro-isoxazole (5RS)-3-(4-Bromophenyl)-5-hydroxymethyl-4,5-dihydro-isoxazole (3.07 g, 12 mM), triphenylphosphine (3.78 g, 14.4 mM) and 3-hydroxyisoxazole (1.02 g, 12 mM) were dissolved in anhydrous tetrahydrofuran (50 ml), cooled to 0° with stirring under nitrogen, and treated with diisopropylazodicarboxylate (2.71 g, 13.4 mM). Stirring was continued for 18 hours, and the mixture evaporated to dryness. The residue was chromatographed on a 90 g Biotage silica column, eluting with 25% ethyl acetate in isohexane, appropriate fractions combined, and chromatographed again on a 40 g Biotage silica column, eluting with 5% methanol in dichloromethane. Appropriate fractions were combined to give the desired product (2.15 g). MS (ESP): 323 (MH$^+$) for C$_{13}$H$_{11}$BrN$_2$O$_3$
NMR (CDCl$_3$) δ: 3.26 (dd, 1H); 3.48 (dd, 1H); 4.43 (d, 2H); 5.13 (m, 1H); 5.99 (d, 1H); 7.54 (s, 4H); 8.13 (d, 1H).

(5RS)-3-(4-Trimethylstannylphenyl)-5-isoxazol-3-yloxymethyl)-4,5-dihydroisoxazole (5RS)-3-(4-Bromophenyl)-5-isoxazol-3-yloxymethyl-4,5-dihydro-isoxazole (2.06 g, 6.38 mM) was treated with hexamethylditin at 100° C. for 18 hours, using essentially the procedure of the equivalent intermediate of Example 1. Crude product was chromatographed on a 40 g Biotage silica column, eluting with 25% ethyl acetate in isohexane. Relevant fractions were combined to give the desired product (2.21 g).
NMR(CDCl$_3$) δ: 0.30 (s, 9H); 3.28 (dd, 1H); 3.50 (dd, 1H); 4.41 (d, 2H); 5.12 (m, 1H); 5.99 (d, 1H); 7.54 (d, 2H); 7.63 (d, 2H); 8.12 (d, 1H).

(5RS)-3-(4-(1-t-Butoxycarbonyl-1,2,5,6-tetrahydropyrid-4-yl)phenyl)-5-isoxazol-3-yloxy-methyl)-4,5-dihydroisoxazole (5RS)-3-(4-Trimethylstannylphenyl)-5-isoxazol-3-yloxymethyl)-4,5-dihydroisoxazole (2 g, 4.93 mM) was treated with 1-t-butoxycarbonyl-4-trifluorosulfonyloxy-1,2,5,6-tetrahydropyridine at ambient temperature for 18 hours, using essentially the procedure of the equivalent intermediate of Example 1. Crude product was chromatographed on a 20 g silica Mega Bond Elut® column, eluting with 25% ethyl acetate in isohexane. Relevant fractions were combined to give the desired product (560 mg).

NMR (CDCl$_3$) δ: 1.49 (s, 9H); 2.53 (br, 2H); 3.28 (dd, 1H); 3.50 (dd, 1H); 3.65 (t, 2H); 4.09 (m, 2H); 4.43 (d, 2H); 5.13 (m, 1H); 5.99 (d, 1H); 6.13 (br, 1H); 7.42 (d, 2H); 7.65 (d, 2H); 8.13 (d, 1H).

(5RS)-3-(4-(1,2,5,6-Tetrahydropyrid-4-yl)phenyl)-5-isoxazol-3-yloxymethyl-4,5-dihydroisoxazole hydrochloride (5RS)-3-(4-(1-t-Butoxycarbonyl-1,2,5,6-tetrahydropyrid-4-yl)phenyl)-5-isoxazol-3-yloxy-methyl-4,5-dihydroisoxazole (500 mg, 1.18 mM) was treated with ethanolic hydrogen chloride using essentially the procedure of the equivalent intermediate of Example 1. The desired product crystallised from the reaction mixture (300 mg).

MS (ESP): 326 (MH$^+$) for $C_{18}H_{19}N_3O_3$

NMR (DMSO-d$_6$) δ: 2.68 (br, 2H); 3.29 (m overlapping H$_2$O, 3H); 3.56 (dd, 1H); 3.72 (br, 2H); 4.28 (dd, 1H); 4.36 (dd, 1H); 5.06 (m, 1H); 6.28 (s, 1H); 6.33 (d, 1H); 7.54 (d, 2H); 7.66 (d, 2H); 8.66 (d, 1H); 9.37 (br, 2H).

EXAMPLE 4

(5RS)-3-(3-Fluoro-4-morpholin-4ylphenyl)-5-isoxazol-3-loxymethyl-4,5-dihydroisoxazole (5RS)-3-(3,4-Difluorophenyl)-5-isoxazol-3-yloxymethyl-4,5-dihydroisoxazole (110 mg, 0.396 mM) and potassium carbonate (82 mg, 0.594 mM) were suspended in morpholine (1.5 ml) under nitrogen and heated to 130° for 40 hours. After cooling, the mixture was partitioned between water (30 ml) and ethyl acetate (30 ml). The organic extract was washed with aqueous hydrochloric acid (2N, 15 ml), sodium bicarbonate (15 ml), and brine (15 ml). After drying (magnesium sulfate) and evaporation, the desired product was obtained as a white solid (120 mg). MS (ESP): 348 (MH$^+$) for $C_{11}H_{18}FN_3O_4$ NMR(DMSO-d$_6$) δ: 3.05 (t, 4H); 3.26 (dd, 1H); 3.51 (dd overlapped by H$_2$O, 1H); 3.72 (t, 4H); 4.27 (dd, 1H); 4.33 (dd, 1H); 5.03 (m, 1H); 6.34 (d, 1H); 7.07 (t, 1H); 7.41 (overlapping m, 2H); 8.64 (d, 1H).

The intermediates for this compound were prepared as follows:—

(5RS)-3-(3,4-Difluorophenyl)-5-hydroxymethyl-4,5-dihydroisoxazole 3,4-Difluorobenzohydroximinoyl chloride (4 g, 20.9 mM) and allyl alcohol (1.21 g, 20.9 mM) were dissolved in anhydrous diethyl ether (250 ml) under a nitrogen atmosphere, and a solution of triethylamine (2.74 g, 27.16 mM) in anhydrous diethyl ether (10 ml) was run in dropwise over 20 minutes. A copious white precipitate formed, and the mixture was stirred for 18 hours. The mixture was treated with ethyl acetate (800 ml) and brine (250 ml), the organic layer separated, and washed with brine (500 ml). After drying (magnesium sulfate) and evaporation, the crude product was purified by chromatography on silica, eluting with a gradient form 0–5% methanol in dichloromethane. Relevant fractions were combined to give the desired product (4.26 g). MS (ESP): 214 (MH$^+$) for $C_{10}H_9F_2NO_2$ NMR (DMSO-d$_6$) δ: 3.17 (dd, 1H); 3.38 (dd, 1H); 3.49 (m, 2H); 4.71 (m, 1H); 4.94 (m, 1H); 7.49 (overlapping m, 2H); 7.68 (dd, 1H).

The benzohydroximinoyl chloride starting material is described in WO 99-41244.

(5RS)-3-(3,4-Difluorophenyl)-5-methanesulfonyloxymethyl-4,5-dihydroisoxazole (5RS)-3-(3,4-Difluorophenyl)-5-hydroxymethyl-4,5-dihydroisoxazole (3.79 g, 17.8 mM) was dissolved in anhydrous dichloromethane (200 ml) under a nitrogen atmosphere, cooled to 0°, and treated with triethylamine (2.51 g, 24.9 mM). Methanesulfonyl chloride (2.45 g, 21.4 mM) was added dropwise with stirring during a period of 30 minutes, then the mixture allowed to come to ambient temperature over 2 hours. The mixture was treated with water (200 ml), the organic layer separated, and washed with aqueous hydrochloric acid (2N, 100 ml), sodium bicarbonate (100 ml), and brine (200 ml). After drying (magnesium sulfate) and evaporation, the desired product was obtained as a white solid (4.85 g).

MS (ESP): 292 (MH$^+$) for $C_{11}H_{11}F_2NO_4S$

NMR (DMSO-d$_6$) δ: 3.20 (s, 3H); 3.24 (dd, 1H); 3.56 (dd, 1H); 4.29 (dd, 1H); 4.37 (dd, 1H); 5.03 (m, 1H); 7.51 (overlapping m, 2H); 7.71 (td, 1H).

(5RS)-3-(3,4-Difluorophenyl)-5-isoxazol-3-yloxymethyl-4,5-dihydroisoxazole

A slurry of sodium hydride (60% in oil, 40 mg, 1 mM) in anhydrous N,N-dimethylformamide (1 ml) under an atmosphere of nitrogen was added dropwise with stirring to a solution of 3-hydroxyisoxazole (94 mg, 11.1 mM) in anhydrous N,N-dimethylformamide (1 ml).

After heating the white suspension to 40° for 15 minutes, a solution of(5RS)-3-(3,4-difluorophenyl)-5-methanesulfonyloxymethyl-4,5-dihydroisoxazole (291 mg, 1 mM) in anhydrous N,N-dimethylformamide (2 ml) was added slowly, and the mixture heated to 70° for 24 hours. The mixture was cooled, treated with aqueous sodium bicarbonate solution (30 ml), and extracted into ethyl acetate (2×30 ml). The combined extracts were washed with water (30 ml), brine (30 ml), and dried (magnesium sulfate). After evaporation, the crude product was chromatographed on a 20 g silica Mega Bond Elut® column, eluting with a gradient from 0–1% methanol in dichloromethane. Relevant fractions were combined to give the desired product (130 mg). MS (ESP): 281 (MH$^+$) for $C_{13}H_{10}F_2N_2O_3$ NMR (DMSO-d$_6$) δ: 3.31 (dd overlapped by H$_2$O, 1H); 3.56 (dd, 1H); 4.29 (dd, 1H); 4.35 (dd, 1H); 5.09 (m, 1H); 6.33 (d, 1H); 7.53 (overlapping m, 2H); 7.72 (td, 1H); 8.66 (d, 1H).

EXAMPLE 5

(5RS)-3-(3-Fluoro-4-imidazol-1-ylphenyl)-5-isoxazol-3-yloxymethyl-4,5-dihydroisoxazole A slurry of sodium hydride (60% in oil, 22 mg, 0.55 mM) in anhydrous N,N-dimethylformamide (0.5 ml) was stirred under an atmosphere of nitrogen and treated dropwise with a solution of imidazole (38 mg, 0.55 mM) in anhydrous N,N-dimethylformamide (0.5 ml) at 0°. The mixture was allowed to warm to ambient temperature over 20 minutes, then a solution of (5RS)-3-(3,4-difluorophenyl)-5-isoxazol-3-yloxymethyl-4,5-dihydroisoxazole (140 mg, 0.5 mM) in anhydrous N,N-dimethylformamide (1 ml) added, and the mixture stirred at 70° for 16 hours. After cooling, the mixture was partitioned between aqueous sodium bicarbonate solution (20 ml) and ethyl acetate (20 ml), and the organic extract washed with water (20 ml) and brine (20 ml). After drying (magnesium sulfate) and evaporation, the crude product was chromatographed on a 10 g silica Mega Bond Elut® column, eluting with a gradient from 0–2.5% methanol in dichloromethane. Relevant fractions were combined to give the desired product (68 mg). MS (ESP): 329 (MH$^+$) for $C_{16}H_{13}FN_4O_3$ NMR (DMSO-$d_6$) δ: 3.36 (dd, 1H); 3.61 (dd, 1H); 4.31 (dd, 1H); 4.38 (dd, 1H); 5.13 (m, 1H); 6.34 (d, 1H); 7.13 (d, 1H); 7.62 (overlapping m, 2H); 7.74 (overlapping m, 2H); 8.09 (d, 1H); 8.66 (d, 1H).

EXAMPLE 6

(5RS)-3-(3-Fluoro-4-thiomorpholin-4-ylphenyl)-5-isoxazol-3-yloxyethyl-4,5-dihydroisoxazole (5RS)-3-(3,4-Difluorophenyl)-5-isoxazol-3-yloxymethyl-4,5-dihydroisoxazole (420 mg, 1.5 mM) was treated with thiomorpholine using essentially the conditions of Example 4. Crude product was chromatographed on a 20 g silica Mega Bond Elut® column, eluting with dichloromethane. Relevant fractions were combined to give the desired product (273 mg).

MS (ESP): 364 (MH$^+$) for $C_{17}H_{18}FN_3O_3S$

NMR (DMSO-$d_6$) δ: 2.73 (t, 4H); 3.29 (m overlapped by $H_2O$, 5H); 3.50 (dd, 1H); 4.26 (dd, 1H); 4.33 (dd, 1H); 5.03 (m, 1H); 6.33 (d, 1H); 7.09 (t, 1H); 7.40 (overlapping m, 2H); 8.66 (d, 1H).

EXAMPLE 7

(5RS)-3-(3-Fluoro-4-pyrazol-1-ylphenyl)-5-isoxazol-3-yloxymethyl-4,5-dihydroisoxazole (5RS)-3-(3,4-Difluorophenyl)-5-isoxazol-3-yloxymethyl-4,5-dihydroisoxazole (140 mg, 0.5 mM) was treated with pyrazole using essentially the conditions of Example 5. Crude product was chromatographed on a S g silica Mega Bond Elut® column, eluting with a gradient from 0–25% ethyl acetate in dichloromethane. Relevant fractions were combined to give the desired product (37 mg). MS ESP): 329 (MH$^+$) for $C_{16}H_{13}FN_4O_3$ NMR (CDCl$_3$) δ: 3.30 (dd, 1H); 3.50 (dd, 1H); 4.45 (d, 2H); 5.16 (m, 1H); 6.00 (d, 1H); 6.51 (dd, 1H); 7.51 (dd, 1H); 7.62 (dd, 1H); 7.76 (d, 1H); 8.03 (t, 1H); 8.08 (dd, 1H); 8.13 (d, 1H).

EXAMPLE 8

(5RS)-3-(3-Fluoro-4-(1.2.3-triazol-1-yl)phenyl)-5-isoxazol-3-yloxymethyl-4,5-dihydroisoxazole and (SRS)-3-(3-fluoro-4-(1,2,3-triazol-2-yl)phenyl)-5-isoxazol-3-yl-oxymethyl-4,5-dihydroisoxazole (5RS)-3-(3,4-Difluorophenyl)-5-isoxazol-3-yloxymethyl-4,5-dihydroisoxazole (140 mg, 0.5 mM) was treated with 1,2,3-triazole using essentially the conditions of Example 5. Crude product was chromatographed on a 5 g silica Mega Bond Elut® column, eluting with a gradient from 0–25% ethyl acetate in dichloromethane. The least polar fraction proved to be recovered starting material, and the spot of intermediate polarity was the triazol-2-yl isomer (16 mg). MS(ESP): 330 (MH$^+$) for $C_{15}H_{12}FN_5O_3$ NMR (CDCl$_3$) δ: 3.32 (dd, 1H); 3.52 (dd, 1H); 4.46 (d, 2H); 5.20 (m, 1H); 6.00 (d, 1H); 7.58 (dd, 1H); 7.64 (dd, 1H); 7.91 (s, 2H); 7.95 (t, 1H); 8.14 (d, 1H).

The least polar spot was the triazol-1-yl isomer (21 mg).
MS (ESP): 330 (MH$^+$) for $C_{15}H_{12}FN_5O_3$ NMR (CDCl$_3$) δ: 3.32 (dd, 1H); 3.52 (dd, 1H); 4.47 (d, 2H); 5.20 (m, 1H); 5.99 (d, 1H); 7.58 (dd, 1H); 7.71 (dd, 1H); 7.89 (d, 1H); 8.11 (t, 1H); 8.14 (d, 1H); 8.16 (d, 1H).

EXAMPLE 9

(5RS)-3-(3-Fluoro-4-(1,2,4-triazol-1-yl)phenyl)-5-isoxazol-3-yloxymethyl-4,5-dihydroisoxazole (5RS)-3-(3,4-Difluorophenyl)-5-isoxazol-3-yloxymethyl-4,5-dihydroisoxazole (140 mg, 0.5 mM) was treated with 1,2,4-triazole using essentially the conditions of Example 5. Crude product was chromatographed on a 5 g silica Mega Bond Elut® column, eluting with a gradient from 0–25% ethyl acetate in dichloromethane. Relevant fractions were combined to give the desired product (45 mg). MS (ESP): 330 (MH$^+$) for $C_{15}H_{12}FN_5O_3$ NMR (CDCl$_3$) δ: 3.31 (dd, 1H); 3.51 (dd, 1H); 4.47 (d, 2H); 5.19 (m, 1H); 6.00 (d, 1H); 7.58 (dd, 1H); 7.68 (dd, 1H); 8.01 (t, 1H); 8.14 (overlapping m, 2H); 8.73 (d, 1H).

EXAMPLE 10

(5RS)-3-(3-Fluoro-4-(1-oxothiomorpholin-4-yl)phenyl)-5-isoxazol-3-yloxymethyl-4,5-dihydroisoxazole To a stirred solution of (5RS)-3-(3-fluoro-4-thiomorpholin-4-ylphenyl)-5-isoxazol-3-yloxymethyl-4,5-dihydroisoxazole (174 mg, 0.48 mM) in dichloromethane (5 ml) was added dropwise a solution of 3-chloroperoxybenzoic acid (80%, 124 mg, 0.57 mM) in dichloromethane (5 ml) at ambient temperature, and stirring continued for 1 hour. Aqueous sodium metabisulfite (5%, 5 ml) was added, and after stirring for 5 minutes the organic phase was separated. After further extraction with dichloromethane (2×10 ml), the combined extracts were washed with aqueous sodium bicarbonate solution (2×15 ml) and dried (magnesium sulfate). Crude product was chromatographed on a 10 g silica Mega Bond Elut® column, eluting first with a gradient from 0–50% ethyl acetate in dichloromethane (to remove sulfone, 10 mg), then with a gradient from 0–2.5% methanol in dichloromethane. Relevant fractions were combined to give the desired product (128 mg).

MS (ESP): 380 (MH$^+$) for $C_{17}H_{18}FN_3O_4S$

NMR (DMSO-$d_6$) δ: 2.82 (dm, 2H); 3.01 (tm, 2H); 3.29 (m overlapped by $H_2O$, 3H); 3.52 (dd, 1H); 3.61 (tm, 2H); 4.26 (dd, 1H); 4.33 (dd, 1H); 5.03 (m, 1H); 6.33 (d, 1H); 7.20 (t, 1H); 7.41 (overlapping m, 2H); 8.66 (d, 1H).

EXAMPLE 11

(5RS)-3-(3-Fluoro-4-(1,1-dioxothiomorpholin-4-yl)phenyl)-5-isoxazol-3-yl-oxymethyl-4,5-dihydroisoxazole To a stirred solution of (5RS)-3-(3-fluoro-4-(1-oxothiomorpholin-4-yl)phenyl)-5-isoxazol-3-yloxymethyl-4,5-dihydroisoxazole (104 mg, 0.274 mM) in dichloromethane (5 ml) was added dropwise a solution of 3-chloroperoxybenzoic acid (80%, 95 mg, 0.44 mM) in dichloromethane (5 ml) at ambient temperature, and stirring continued for 1.5 hours. Aqueous sodium metabisulfite (5%, 5 ml) was added, and after stirring for 5 minutes the organic phase was separated. After further extraction with dichloromethane (2×10 ml), the combined extracts were washed with aqueous sodium bicarbonate solution (2×10 ml) and dried (magnesium sulfate). Crude product was chromatographed on a 10 g silica Mega Bond Elut® column, eluting with a gradient from 0–25% ethyl acetate in dichloromethane. Relevant fractions were combined to give the desired product (45 mg).

MS (ESP): 396 (MH$^+$) for $C_{17}H_{18}FN_3O_5S$

NMR (DMSO-d$_6$) δ: 3.26 (m overlapped by H$_2$O, 5H); 3.52 (dd, 1H); 3.58 (m, 4H); 4.26 (dd, 1H); 4.33 (dd, 1H); 5.05 (m, 1H); 6.32 (d, 1H); 7.20 (t, 1H); 7.39 (dd, 1H); 7.45 (dd, 1H); 8.65 (d, 1H).

EXAMPLE 12

(5RS)-3-(3-Fluoro-4-piperazin-1-ylphenyl)-5-isoxazol-3-yloxymethyl-4,5-dihydroisoxazole (5RS)-3-(3,4-Difluorophenyl)-5-isoxazol-3-yloxymethyl-4,5-dihydroisoxazole (530 mg, 1.89 mM) was treated with piperazine using essentially the conditions of Example 4, except that the reaction conditions were 140° for 4 hours, and work-up did not include an acid wash. Crude product was chromatographed on a 50 g silica Mega Bond Elut® column, eluting with a mixture of dichloromethane/methanol/ammonia 90:10:1. Relevant fractions were combined to give the desired product (601 mg). MS (ESP): 347 (MH$^+$) for $C_{17}H_{11}FN_4O_3$ NMR (DMSO-d$_6$) δ: 2.84 (t, 4H); 2.99 (t, 4H); 3.27 (m overlapped by H$_2$O, 1H); 3.50 (dd, 1H); 4.26 (dd, 1H); 4.34 (dd, 1H); 5.03 (m, 1H); 6.33 (d, 1H); 7.04 (t, 1H); 7.37 (overlapping m, 2H); 8.65 (d, 1H); NH missing—exchanged.

EXAMPLE 13

(5RS)-3-(3-Fluoro-4-(4-methanesulfonyl)piperazin-1-ylphenyl)-5-isoxazol-3-yloxymethyl-4,5-dihydroisoxazole (5RS)-3-(3-Fluoro-4-piperazin-1-ylphenyl)-5-isoxazol-3-yloxymethyl-4,5-dihydroisoxazole (100 mg, 0.29 mM) in dichloromethane (2.5 ml) at 0° was treated with aqueous sodium bicarbonate (5%, 2.5 ml), and the mixture stirred vigorously. An excess of methanesulfonyl chloride (300 mg, 2.6 mM) was added, and the mixture was allowed to come to ambient temperature while stirring for 16 hours. The mixture was diluted with dichloromethane (15 ml) and water (15 ml), the organic layer separated, and washed successively with water (15 ml) and brine (15 ml). After drying (magnesium sulfate) and evaporation, the crude product was chromatographed on a 5 g silica Mega Bond Elut® column, eluting with a gradient from 0–2.5% methanol in dichloromethane. Relevant fractions were combined to give the desired product (104 mg). MS (ESP): 425 (MH$^+$) for $C_{18}H_{21}FN_4O_5S$ NMR (DMSO-d$_6$) δ: 2.92 (s, 3H); 3.17 (t, 4H); 3.26 (m overlapped by H$_2$O, 5H); 3.52 (dd, 1H); 4.27 (dd, 1H); 4.34 (dd, 1H); 5.04 (m, 1H); 6.34 (d, 1H); 7.11 (t, 1H); 7.42 (overlapping m, 2H); 8.64 (d, 1H).

EXAMPLE 14

(5RS)-3-(3-Fluoro-4-(4-acetyl)piperazin-1-ylphenyl)-5-isoxazol-3-yloxymethyl-4,5-dihydroisoxazole (5RS)-3-(3-Fluoro-4piperazin-1-ylphenyl)-5-isoxazol-3-yloxymethyl-4,5-dihydroisoxazole (100 mg, 0.29 mM) was treated with acetic anhydride using essentially the conditions of Example 13, to give the desired product after chromatography (98 mg).

MS (ESP): 389 (MH$^+$) for $C_{19}H_{21}FN_4O_4$

NMR (DMSO-d$_6$) δ: 2.03 (s, 3H); 3.02 (t, 2H); 3.08 (t, 2H); 3.25 (dd overlapped by H$_2$O, 1H); 3.51 (dd, 1H); 3.56 (m, 4H); 4.26 (dd, 1H); 4.34 (dd, 1H); 5.03 (m, 1H); 6.34 (d, 1H); 7.08 (t, 1H); 7.41 (overlapping m, 2H); 8.64 (d, 1H).

EXAMPLE 15

(5RS)-3-(3-Fluoro-4-(4-methoxycarbonyl)piperazin-1-ylphenyl)-5-isoxazol-3-yloxymethyl-4,5-dihydroisoxazole (5RS)-3-(3-Fluoro-4-piperazin-1-ylphenyl)-5-isoxazol-3-yloxymethyl-4,5-dihydroisoxazole (100 mg, 0.29 mM) was treated with methyl chloroformate using essentially the conditions of Example 13, to give the desired product after chromatography (107 mg).

MS (ESP): 405 (MH$^+$) for $C_{19}H_{21}FN_4O_5$

NMR (DMSO-d$_6$) δ: 3.04 (t, 4H); 3.24 (dd overlapped by H$_2$O, 1H); 3.51 (overlapping m, 5H); 3.61 (s, 3H); 4.26 (dd, 1H); 4.33 (dd, 1H); 5.03 (m, 1H); 6.34 (d, 1H); 7.08 (t, 1H); 7.41 (overlapping m, 2H); 8.65 (d, 1H).

EXAMPLE 16

(5RS)-3-(3-Fluoro-4-((4S)-2,2-dimethyl-1,3-dioxolane-4-carbonyl)-piperazin-1-ylphenyl)-5-isoxazol-3-yloxymethyl-4,5-dihydroisoxazole (5RS)-3-(3-Fluoro-4-piperazin-1-ylphenyl)-5-isoxazol-3-yloxymethyl-4,5-dihydroisoxazole (175 mg, 0.51 mM) in dry dichloromethane (3 ml) at 0° under nitrogen was treated with pyridine (200 mg, 2.53 mM). After stirring 5 minutes, (4S)-2,2-dimethyl-1,3-dioxolan-4-carbonyl chloride (168 mg, 1.02 mM) in dichloromethane (1 ml) was added, and the mixture was allowed to come to ambient temperature while stirring for 1 hour. The mixture was diluted with dichloromethane (15 ml) and the organic layer separated, and washed successively with aqueous sodium dihydrogen phosphate, sodium bicarbonate, water, and brine (15 ml of each), the organic layer separated, and washed successively with water (15 ml) and brine (15 ml). After drying (magnesium sulfate) and evaporation, the crude product was chromatographed on a 5 g silica Mega Bond Elut® column, eluting with 2.5% methanol in dichloromethane. Relevant fractions were combined, dissolved in dichloromethane, and the desired product (163 mg) precipitated by addition of isohexane.

MS (ESP): 475 (MH$^-$) for $C_{23}H_{27}FN_4O_6$

NMR (DMSO-d$_6$) δ: 1.31 (s, 6H); 3.07 (m, 4H); 3.25 (dd overlapped by H$_2$O, 1H); 3.52 (dd, 1H); 3.64 (m, 4H); 4.07 (t, 1H); 4.21 (dd, 1H); 4.27 (dd, 1H); 4.34 (dd, 1H); 4.88 (t, 1H); 5.05 (m, 1H); 6.32 (d, 1H); 7.09 (t, 1H); 7.42 (overlapping m, 2H); 8.66 (d, 1H).

EXAMPLE 17

(5RS)-3-(3-Fluoro-4-(4-((2S)-2,3-dihydroxypropionyl)piperazin-1-yl)phenyl)-5-isoxazol-3-yloxymethyl-4,5-dihydroisoxazole (5RS)-3-(3-Fluoro-4-((4S)-2,2-dimethyl-1,3-dioxolane-4-carbonyl)piperazin-1-ylphenyl)-5-isoxazol-3-yloxymethyl-4,5-dihydroisoxazole (102 mg, 0.215 mM) in tetrahydrofuran (5 ml) was treated with hydrochloric acid (2N, 1 ml), and the mixture stirred at ambient temperature for 18 hours. Solid potassium carbonate was added to remove water and acid, and the mixture filtered. The residue after evaporation was chromatographed on a 5 g silica Mega Bond Elut® column, eluting with a gradient from 5–10% methanol in dichloromethane. Relevant fractions were combined to give the desired product (163 mg).

MS (ESP): 435 (MH$^-$) for $C_{20}H_{23}FN_4O_6$

NMR (DMSO-d$_6$) δ: 3.12 (m, 4H); 3.33 (dd overlapped by H$_2$O, 1H); 3.52 (dd, 1H); 3.53 (overlapping m, 2H); 3.72 (m, 4H); 4.34 (overlapping m, 3H); 4.79 (t, 1H); 5.06 (d, 1H); 5.06 (m, 1H); 6.41 (d, 1H); 7.16 (t, 1H); 7.49 (overlapping m, 2H); 8.74 (d, 1H).

EXAMPLE 18

(5RS)-3-(3-Fluoro-4-(4-(2-acetoxyacetyl)piperazin-1-yl)phenyl)-5-isoxazol-3-yloxymethyl-4,5-dihydroisoxazole (5RS)-3-(3-Fluoro-4-piperazin-1-ylphenyl)-5-isoxazol-3-yloxymethyl-4,5-dihydroisoxazole (175 mg, 0.51 mM) was treated with acetoxyacetyl chloride using essentially the conditions of Example 16, to give the desired product after chromatography and precipitation (163 mg).

MS (ESP): 447 (MH$^+$) for $C_{21}H_{23}FN_4O_6$

NMR (DMSO-d$_6$) δ: 2.08 (s, 3H); 3.07 (m, 4H); 3.25 (dd overlapped by H$_2$O, 1H); 3.51 (dd, 1H); 3.56 (m, 4H); 4.27 (dd, 1H); 4.34 (dd, 1H); 4.80 (s, 2H); 5.03 (m, 1H); 6.34 (d, 1H); 7.09 (t, 1H); 7.42 (overlapping m, 2H); 8.65 (d, 1H).

EXAMPLE 19

(5RS)-3-(3-Fluoro-4-(4-(2-hydroxyacetyl)piperazin-1-yl)phenyl)-5-isoxazol-3-yloxymethyl-4,5-dihydroisoxazole (5RS)-3-(3-Fluoro-4(4-(2-acetoxyacetyl)piperazin-1-yl) phenyl)-5-isoxazol-3-yloxymethyl-4,5-dihydroisoxazole (112 mg, 0.25 mM) was suspended in a saturated solution of ammonia in methanol (8 ml), diluted with tetrahydrofuran (5 ml). The mixture was stirred at ambient temperature for 40 hours. The residue after evaporation was chromatographed on a 5 g silica Mega Bond Elut® column, eluting with a gradient from 0–5% methanol in dichloromethane. Relevant fractions were combined to give the desired product (92 mg).

MS (ESP): 405 (MH$^+$) for $C_{19}H_{21}FN_4O_5$

NMR (DMSO-d$_6$) δ: 3.06 (m, 4H); 3.24 (dd overlapped by H$_2$O, 1H); 3.51 (dd, 1H); 3.60 (m, 4H); 4.11 (d, 2H); 4.26 (dd, 1H); 4.34 (dd, 1H); 4.60 (t, 1H); 5.04 (m, 1H); 6.34 (d, 1H); 7.08 (t, 1H); 7.41 (overlapping m, 2H); 8.65 (d, 1H).

EXAMPLE 20

(5RS)-3-(3-Fluoro-4-imidazol-1-ylphenyl)-5-isoxazol-3-ylaminomethyl-4,5-dihydroisoxazole (5RS)-3-(3-Fluoro-4-imidazol-1-ylphenyl)-5-(N-(t-butoxycarbonyl)isoxazol-3-ylaminomethyl-4,5-dihydroisoxazole (65 mg, 0.15 mM) was dissolved in dichloromethane (0.5 ml) and treated with trifluoroacetic acid (0.5 ml). After stirring for 15 minutes the reaction was poured into a mixture of aqueous sodium bicarbonate (5%, 15 ml) and ethyl acetate (15 ml). The organic layer was separated, and washed successively with aqueous sodium bicarbonate, water, and brine (15 ml of each), then dried (magnesium sulfate). Solvent was evaporated, the residue dissolved in the minimum of dichloromethane. The title product (33 mg) was precipitated by the addition of diethyl ether.

MS (ESP): 328 (MH$^+$) for $C_{16}H_{14}FN_5O_2$

NMR (DMSO-d$_6$) δ: 3.22 (dd, 1H); 3.27 (m overlapped by H$_2$O, 2H); 3.52 (dd, 1H); 4.95 (m, 1H); 5.96 (d, 1H); 6.39 (t, 1H); 7.13 (d, 1H); 7.62 (overlapping m, 2H); 7.74 (overlapping m, 2H); 8.08 (d, 1H); 8.35 (d, 1H).

The intermediates for this compound were prepared as follows:—

(5RS)-3-(3,4-Difluorophenyl)-5-(N-(t-butoxycarbonyl)isoxazol-3-ylaminomethyl-4,5-dihydroisoxazole N-Allyl-3-(t-butoxycarbonylamino)isoxazole (4.67 g, 20.89 mM) and 3,4-difluorobenzohydroximinoyl chloride (4 g, 20.9 mM) were treated with dry triethylamine (2.74 g, 27.16 mM) under essentially the conditions used for the comparable intermediate for Example 4.

After work-up, the crude material was dissolved in the minimum volume of diethyl ether, and the desired product (4.29 g) precipitated by the addition of isohexane.

MS (ESP): 380 (MH$^+$) for $C_{18}H_{19}F_2N_3O_4$

NMR (DMSO-d$_6$) δ: 1.45 (s, 9H); 3.20 (dd, 1H); 3.51 (dd, 1H); 3.80 (dd, 1H); 4.05 (dd, 1H); 5.05 (m, 1H); 6.83 (d, 1H); 7.53 (overlapping m, 2H); 7.71 (td, 1H); 8.78 (d, 1H).

(5RS)-3-(3-Fluoro-4-imidazol-1-ylphenyl)-5-(N-(t-butoxycarbonyl)isoxazol-3-ylaminomethyl-4,5-dihydroisoxazole (5RS)-3-(3,4-Difluorophenyl)-5-(N-(t-butoxycarbonyl) isoxazol-3-ylaminomethyl-4,5-dihydroisoxazole (190 mg, 0.5 mM) was treated with imidazole essentially as in Example 5. Relevant fractions after chromatography were combined to give the desired product (85 mg).

MS (ESP): 428 (MH$^+$) for $C_{21}H_{22}FN_5O_4$

NMR (DMSO-d$_6$) δ: 1.45 (s, 9H); 3.24 (dd, 1H); 3.55 (dd, 1H); 3.82 (dd, 1H); 4.08 (dd, 1H); 5.09 (m, 1H); 6.82 (d, 1H); 7.14 (d, 1H); 7.61 (d, 1H); 7.64 (dd, 1H); 7.74 (dd, 1H); 7.76 (t, 1H); 8.08 (d, 1H); 8.77 (d, 1H).

EXAMPLE 21

(5RS)-3-(3-Fluoro-4-morpholin-4-yl phenyl)-5-isoxazol-3-ylaminomethyl-4,5-dihydroisoxazole (5RS)-3-(3,4-Difluorophenyl)-5-[(N-(t-butoxycarbonyl) isoxazol-3-ylaminomethyl-4,5-dihydroisoxazole (150 mg, 0.396 mM) was treated with morpholine essentially as in Example 4. Work-up using dilute acid led to a mixture of the title product and the t-butoxycarbonyl derivative. This was treated with trifluoroacetic acid, according to the procedure of Example 20, to give the desired product (42 mg). MS (ESP): 347 (MH⁻) for $C_{17}H_{19}FN_4O_3$ NMR(DMSO-$d_6$) δ: 3.05 (t, 4H); 3.13 (dd, 1H); 3.23 (dd overlapped by H$_2$O, 2H); 3.42 (dd, 1H); 3.72 (t, 4H); 4.85 (m, 1H); 5.95 (d, 1H); 6.35 (t, 1H); 7.06 (t, 1H); 7.37 (overlapping m, 2H); 8.34 (d, 1H).

EXAMPLE 22

(5RS)-3-(3-Fluoro-4-thiomorpholin-4-yl phenyl)-5-isoxazol-3-ylaminomethyl-4,5-dihydroisoxazole (5RS)-3-(3,4-Difluorophenyl)-5-(N-(t-butoxycarbonyl)isoxazol-3-ylaminomethyl-4,5-dihydroisoxazole (853 mg, 2.25 mM) was treated with thiomorpholine essentially as in Example 4, except that the work-up omitted an acid wash. Crude product was then purified by chromatography on a 50 g silica Mega Bond Elut® column, eluting with a gradient from 0–5% methanol in dichloromethane, followed by re-chromatography of appropriate fractions on a 20 g silica Mega Bond Elut® column, eluting with a gradient from 0–20% ethyl acetate in dichloromethane. Relevant fractions were combined to give the desired product (255 mg).

MS (ESP): 363 (MH⁺) for $C_{17}H_{19}FN_4O_2S$

NMR (DMSO-$d_6$) δ: 2.72 (t, 4H); 3.12 (dd, 1H); 3.27 (overlapping m+H$_2$O, ~6H); 3.42 (dd, 1H); 4.85 (m, 1H); 5.96 (d, 1H); 6.36 (t, 1H); 7.10 (t, 1H); 7.35 (overlapping m, 2H); 8.34 (d, 1H).

EXAMPLE 23

(5RS)-3-(3-Fluoro-4-(1-oxothiomorpholin-4-ylphenyl)-5-isoxazol-3-ylaminomethyl-4,5-dihydroisoxazole and (5RS)-3-(3-fluoro-4-(1,1-dioxothiomorpholin-4-yl)phenyl)-5-isoxazol-3-ylaminomethyl-4,5-dihydroisoxazole To a stirred solution of (5RS)-3-(3-fluoro-4-thiomorpholin-4-ylphenyl)-5-isoxazol-3-ylaminomethyl-4,5-dihydroisoxazole (160 mg, 0.44 mM) in dichloromethane (5 ml) was added dropwise a solution of 3-chloroperoxybenzoic acid (80%,137 mg, 0.64 mM) in dichloromethane (5 ml) at ambient temperature, and stirring continued for 1 hour. Aqueous sodium metabisulfite (5%, 5 ml) was added, and after stirring for 5 minutes the organic phase was separated. After further extraction with dichloromethane (2×10 ml), the combined extracts were washed with aqueous sodium bicarbonate solution (2×10 ml) and dried (magnesium sulfate). Crude product was chromatographed on a 10 g silica Mega Bond Elut® column, eluting first with a gradient from 0–50% ethyl acetate in dichloromethane to give the sulfone (20 mg). MS (ESP): 395 (MH⁺) for $C_{17}H_{19}FN_4O_4S$ NMR (DMSO-$d_6$) δ: 3.14 (dd, 1H); 3.23 (overlapping m+H$_2$O, ~6H); 3.43 (dd, 1H); 3.55 (t, 4H); 4.86 (m, 1H); 5.96 (d, 1H); 6.35 (t, 1H); 7.20 (t, 1H); 7.37 (dd, 1H); 7.43 (dd, 1H); 8.34 (d, 1H).

Further elution with a gradient from 2.5–6% methanol in dichloromethane gave the more polar sulfoxide (112 mg).

MS (ESP): 379 (MH⁺) for $C_{17}H_{19}FN_4O_3S$

NMR (DMSO-$d_6$) δ: 2.82 (dm, 2H); 3.02 (tm, 2H); 3.13 (dd, 1H); 3.22 (m overlapped by H$_2$O, 2H); 3.34 (dm, 2H); 3.44 (dd, 1H); 3.61 (t, 2H); 4.85 (m, 1H); 5.96 (d, 1H); 6.35 (t, 1H); 7.19 (t, 1H); 7.39 (overlapping m, 2H); 8.34 (d, 1H).

EXAMPLE 24

(5RS)-3-(3-Fluoro-4-pyrazol-1-ylphenyl)-5-isoxazol-3-ylaminomethyl-4,5-dihydroisoxazole (5RS)-3-(3-Fluoro-4-pyrazol-1-ylphenyl)-5-(N-(t-butoxycarbonyl)isoxazol-3-ylaminomethyl-4,5-dihydroisoxazole (55 mg, 0.13 mM) was treated with trifluoroacetic acid essentially as in Example 20. Crude product was chromatographed on a 5 g silica Mega Bond Elut® column, eluting first with a gradient from 0–25% ethyl acetate in dichloromethane to give the desired product (30 mg). MS (ESP): 328 (MH⁺) for $C_{16}H_{14}FN_5O_2$ NMR (DMSO-$d_6$) δ: 3.23 (dd, 1H); 3.27 (m overlapped by H$_2$O, 2H); 3.51 (dd, 1H); 4.93 (m, 1H); 5.97 (d, 1H); 6.39 (t, 1H); 6.59 (t, 1H); 7.63 (dd, 1H); 7.70 (dd, 1H); 7.83 (d, 1H); 7.90 (t, 1H); 8.24 (t, 1H); 8.35 (d, 1H).

The intermediate for this compound was prepared as follows:—

(5RS)-3-(3-Fluoro-4-pyrazol-1-ylphenyl)-5-(N-(t-butoxycarbonyl)isoxazol-3-ylaminomethyl-4,5-dihydroisoxazole (5RS)-3-(3,4-Difluorophenyl)-5-(N-(t-butoxycarbonyl)isoxazol-3-ylaminomethyl-4,5-dihydroisoxazole (190 mg, 0.5 mM) was treated with pyrazole essentially as in Example 5. Crude product was chromatographed on a 5 g silica Mega Bond Elut® column, eluting with a gradient from 0–25% ethyl acetate in dichloromethane. Relevant fractions were combined to give the desired product (117 mg). MS (ESP): 428 (MH⁺) for $C_{21}H_{22}FN_5O_4$ NMR(CDCl$_3$) δ: 1.53 (s, 9H); 3.18 (dd, 1H); 3.40 (dd, 1H); 4.00 (dd, 1H); 4.22 (dd, 1H); 5.22 (m, 1H); 6.50 (t, 1H); 6.88 (br, 1H); 7.50 (dd, 1H); 7.60 (dd, 1H); 7.76 (d, 1H); 8.00 (t, 1H); 8.07 (t, 1H); 8.24 (d, 1H).

EXAMPLE 25

(5RS)-3-(3-Fluoro-4-piperazin-1-ylphenyl)-5-isoxazol-3-ylaminomethyl-4,5-dihydroisoxazole (5RS)-3-(3,4-Difluorophenyl)-5-(N-(t-butoxycarbonyl)isoxazol-3-ylaminomethyl-4,5-dihydroisoxazole (190 mg, 0.5 mM) was treated with piperazine essentially as in Example 12.

Crude product from this stage was a mixture of the title product and its t-butoxycarbonyl derivative. This was treated with trifluoroacetic acid, according to the procedure of Example 20. Crude product was chromatographed on a 10 g silica Mega Bond Elut® column, eluting first with 10% methanol in dichloromethane, then with a mixture of dichloromethane/methanol/ammonia 90:10:1. Relevant fractions were combined to give the desired product (106 mg).

MS (ESP): 346 (MH⁺) for $C_{17}H_{20}FN_5O_2$

NMR (DMSO-$d_6$) δ: 2.83 (t, 4H); 2.98 (t, 4H); 3.13 (dd, 1H); 3.22 (t overlapping H$_2$O, 2H); 3.41 (dd, 1H); 4.84 (m, 1H); 5.96 (d, 1H); 6.36 (t, 1H); 7.03 (t, 1H); 7.34 (overlapping m, 2H); 8.34 (d, 1H); NH missing—exchanged.

EXAMPLE 26

(5RS)=3-(3-Fluoro-4-(4-methanesulfonyl)piperazin-1-ylphenyl)-5-isoxazol-3-ylaminomethyl-4,5-dihydroisoxazole (5RS)-3-(3-Fluoro-4-piperazin-1-ylphenyl)-5-isoxazol-3-ylaminomethyl-4,5-dihydroisoxazole (95 mg, 0.275 mM) was treated methanesulfonyl chloride essentially as in Example 13. Crude product was chromatographed on a 10 g silica Mega Bond Elut® column, eluting with a gradient from 1–2.5% methanol in dichloromethane. Relevant fractions were combined to give the desired product (85 mg). MS (ESP): 424 (MH$^+$) for $C_{18}H_{22}FN_5O_4S$ NMR (DMSO-d$_6$) δ: 2.92 (s, 3H); 3.16 (overlapping m, 5H); 3.24 (m overlapped by H$_2$O, 6H); 3.43 (dd, 1H); 4.86 (m, 1H); 5.96 (d, 1H); 6.35 (d, 1H); 7.11 (t, 1H); 7.40 (overlapping m, 2H); 8.34 (d, 1H).

EXAMPLE 27

(5RS)-3-(3-Fluoro-4-(4-acetyl)piperazin-1-ylphenyl)-5-isoxazol-3-ylaminomethyl-4,5-dihydroisoxazole (5RS)-3-(3-Fluoro-4-piperazin-1-ylphenyl)-5-isoxazol-3-ylaminomethyl-4,5-dihydroisoxazole (95 mg, 0.275 mM) was treated acetic anhydride essentially as in Example 13. Crude product was chromatographed on a 10 g silica Mega Bond Elut® column, eluting with a gradient from 1–2.5% methanol in dichloromethane. Relevant fractions were combined to give the desired product (63 mg). MS (ESP): 424 (MH$^+$) for $C_{19}H_{22}FN_5O_3$ NMR (DMSO-d$_6$) δ: 2.02 (s, 3H); 3.02 (m, 2H); 3.07 (m, 2H); 3.14 (dd, 1H); 3.26 (t overlapped by H$_2$O, 2H); 3.43 (dd, 1H); 3.58 (br, 4H); 4.86 (m, 1H); 5.95 (d, 1H); 6.35 (d, 1H); 7.06 (t, 1H); 7.38 (overlapping m, 2H); 8.34 (d, 1H).

EXAMPLE 28

(5RS)-3-(3-Fluoro-4-(1-((2S)-2,3-dihydroxypropionyl-1,2,5,6-tetrahydro)-pyrid-4-yl))phenyl)-5-isoxazol-3-ylaminomethyl-4,5-dihydroisoxazole (5RS)-3-(3-Fluoro-4-(1,2,5,6-tetrahydropyrid-4-yl))phenyl)-5-isoxazol-3-ylaminomethylisoxazole hydrochloride (300 mg, 0.79 mM) was suspended in dichloromethane (20 ml) under nitrogen, triethylamine (240 mg, 2.37 mM) added, and the mixture cooled to 0°. After stirring for 10 minutes a complete solution was obtained, to which a solution of (4S)-2,2-dimethyl-1,3-dioxolan-4-carbonyl chloride (260 mg, 1.58 mM) in dichloromethane (5 ml) was added dropwise, and stirring continued for 16 hours, allowing the temperature to rise to ambient. The mixture was washed with water (2×20 ml), brine (20 ml), and dried (magnesium sulfate). After evaporation, the residue was chromatographed on a 10 g silica Mega Bond Elut® column, eluting with a gradient from dichloromethane to 5% methanol in dichloromethane. Relevant fractions were combined to give the desired product (80 mg).

MS (ESP): 431 (MH$^+$) for $C_{21}H_{23}FN_4O_5$

NMR (CDCl$_3$) δ: 2.59 (br, 2H); 3.16 (dd, 1H); 3.42 (dd, 1H); 3.48 (t, 1H); 3.63 (dd, 1H); 3.68 (overlapping m, 3H); 3.80 (m, 1H); 3.98–4.43 (overlapping m, 3H); 4.51 (m, 1H); 5.04 (m, 1H); 5.84 (d, 1H); 6.03 (m, 1H); 7.27 (t, 1H); 7.37 (m, 2H); 8.03 (d, 1H).

(2 Exchangeables Missing)

The intermediates for this compound were prepared as follows:—

3-Fluoro-4-iodobenzaldoxime

Formaldoxime was prepared by dissolving paraformaldehyde (3.17 g, 0.105 M) and hydroxylamine hydrochloride (7.23 g, 0.104 M) in water (75 ml) at 80°. Sodium acetate (14.16 g, 0.104 M) was added, the mixture heated to reflux for 15 minutes, and then cooled to room temperature. 3-Fluoro-4-iodoaniline (15.36 g, 0.069 M) and concentrated hydrochloric acid (18.51 g) were dissolved in a mixture of water (30 ml) and ice (30 g). The solution was treated at 0–5° with a solution of sodium nitrite (4.81 g, 0.07 M) in water (15 ml). The pH of the resulting red-brown solution was adjusted to 5–6 by the addition of sodium acetate (6.05 g, 0.044 M). To the solution of formaldoxime was added sodium acetate (45.38 g, 0.333 M), hydrated copper sulfate (1.72 g, 6.9 mM) and sodium sulfite (0.275 g, 2.18 mM), giving a deep green solution, which was cooled to 10–15°. The solution of the diazonium salt was then slowly introduced with vigorous stirring, and stirring continued for 1 hour. The mixture was extracted with diethyl ether (3×100 ml), the combined extracts washed with water (100 ml), and dried (magnesium sulfate). The residue after filtration and evaporation was chromatographed in four portions on 50 g silica Mega Bond Elut® columns, eluting with a gradient from dichloromethane to 5% methanol in dichloromethane. Relevant fractions were combined to give the desired product (3.52 g).

MS (EI): 265 (M+) for $C_7H_5FINO$

NMR (CDCl$_3$) δ: 7.08 (dd, 1H); 7.30 (dd, 1H); 7.66 (s, 1H); 7.77 (t, 1H); 8.06 (s, 1H).

3-Fluoro-4-iodobenzohydroximinoyl chloride

3-Fluoro-4-iodobenzaldoxime (4.9 g, 18.5 mM) was dissolved in N,N-dimethylformamide (30 ml) and the stirred solution treated at 15° with N-chlorosuccinimide (0.72 g, 5.4 mM). Reaction was initiated by the addition of concentrated hydrochloric acid vapour (10 ml), and warming to 40°. Further N-chlorosuccinimide (2 g, 15 mM) was added, and the mixture stirred at ambient temperature for 16 hours. After pouring into ice-water (250 ml), the mixture was extracted with diethyl ether (3×50 ml), the combined extracts washed with brine (25 ml), and dried (magnesium sulfate). The residue after filtration and evaporation was chromatographed on a 50 g silica Mega Bond Elut® column, eluting with a mixture of 25% ethyl acetate in isohexane. Relevant fractions were combined to give the desired product (3.25 g).

NMR(CDCl$_3$) δ: 7.40 (dd, 1H); 7.55 (dd, 1H); 7.79 (dd, 1H); 8.11 (d, 1H).

(5RS)-3-(3-Fluoro-4-iodophenyl)-5-hydroxymethyl-4,5-dihydroisoxazole

3-Fluoro-4-iodobenzohydroximinoyl chloride (3.18 g, 10.6 mM) was treated with allyl alcohol under essentially the conditions of the equivalent intermediate of Example 4. The crude product was purified by chromatography on a 20 g silica Mega Bond Elut® column, eluting with a mixture of 50% ethyl acetate in isohexane. Relevant fractions were combined to give the desired product (2.23 g). MS (ESP): 322 (MH$^+$) for $C_{10}H_9FINO_2$ NMR (CDCl$_3$) δ: 1.93 (dd, 1H); 3.25 (dd, 1H); 3.34 (dd, 1H); 3.68 (dm, 1H); 3.90 (dm, 1H); 4.89 (m, 1H); 7.17 (dd, 1H); 7.36 (dd, 1H); 7.79 (dd, 1H).

(5RS)-3-(3-Fluoro-4-iodophenyl)-5-methanesulfonyloxymethyl-4,5-dihydroisoxazole (5RS)-3-(3-Fluoro-4-iodophenyl)-5-hydroxymethyl-4,5-dihydroisoxazole (2 g, 6.2 mM) was treated with methanesulfonyl chloride under essentially the conditions of the equivalent intermediate of Example 4. Product was obtained as a white solid (2.18 g) without chromatography. MS (EI): 399 (M+) for $C_{11}H_{11}FINO_4S$ NMR (CDCl$_3$) δ: 3.08 (s, 3H); 3.26 (dd, 1H); 3.46 (dd, 1H); 4.37 (m, 2H); 5.04 (m, 1H); 7.18 (dd, 1H); 7.37 (dd, 1H); 7.81 (dd, 1H).

(5RS)-3-(3-Fluoro-4-iodophenyl)-5-(N-(t-butoxycarbonyl)isoxazol-3-ylaminomethyl)-4,5-dihydro-isoxazole A solution of (5RS)-3-(3-Fluoro-4-iodophenyl)-5-methanesulfonyloxymethyl-4,5-dihydroisoxazole (1.7 g, 4.26 mM) in dry N,N-dimethylformamide (40 ml) under nitrogen, was treated with sodium hydride (60% in oil, 0.205 g, 5.13 mM), and stirred for 5 minutes. N-Allyl-3-(t-Butoxycarbonylamino)isoxazole (0.86 g, 4.69 mM) was added, and the mixture heated at 60° for 18 hours. After cooling and dilution with water (200 ml), the mixture was extracted with ethyl acetate (3×100 ml), the extracts were washed with water (2×100 ml), brine (100 ml), dried (magnesium sulfate). The residue after evaporation was purified by chromatography on a 50 g silica Mega Bond Elut® column, eluting with a mixture of 25% ethyl acetate in isohexane. Relevant fractions were combined to give the desired product (1.61 g). MS (ESP): 488 (MH$^+$) for C$_{18}$H$_{19}$FIN$_3$O$_4$ NMR (CDCl$_3$) δ: 1.53 (s, 9H); 3.14 (dd, 1H); 3.36 (dd, 1H); 3.99 (dd, 1H); 4.20 (dd, 1H); 5.21 (m, 1H); 6.89 (d, 1H); 7.18 (dd, 1H); 7.37 (dd, 1H); 7.79 (dd, 1H); 8.23 (d, 1H).

(5RS)-3-(3-Fluoro-4-(1-t-butoxycarbonyl-1,2,5,6-tetrahydropyrid-4-yl)phenyl)-5-(N-(t-butoxycarbonyl)isoxazol-3-ylaminomethyl)-4,5-dihydroisoxazole Tris(dibenzylideneacetone)dipalladium (141 mg, 0.154 mM) and triphenylarsine (188 mg, 0.616 mM) were dissolved in degassed N-methylpyrrolidone (40 ml) under nitrogen, and stirred for 15 minutes. (5RS)-3-(3-Fluoro-4-iodophenyl)-5-(N-(t-butoxycarbonyl)isoxazol-3-ylaminomethyl)-4,5-dihydro-isoxazole (1.5 g, 3.08 mM) and 1-t-butoxycarbonyl-4-trimethylstannyl-1,2,5,6-tetrahydropyridine (1.99 g, 4.62 mM) were added, and the reaction heated at 70–80° for 18 hours. The mixture was filtered through celite and evaporated to dryness, and the residue chromatographed on a 40 g silica Biotage column, eluting with 25% ethyl acetate in isohexane. Relevant fractions were combined to give the desired product (817 mg).

NMR (CDCl$_3$) δ: 1.49 (s, 9H); 1.54 (s, 9H); 2.51 (br, 2H); 3.13 (dd, 1H); 3.37 (dd, 1H); 3.62 (t, 2H); 3.98 (dd, 1H); 4.07 (m, 2H); 4.20 (dd, 1H); 5.19 (m, 1H); 6.01 (br, 1H); 6.89 (br, 1H); 7.27 (t, 1H); 7.37 (m, 2H); 8.23 (d, 1H).

(5RS)-3-(3-Fluoro-4-(1,2,5,6-tetrahydropyrid-4-yl)phenyl]-5-isoxazol-3-ylaminomethyl-4,5-dihydroisoxazole hydrochloride (5RS)-3-(3-Fluoro-4-(1-t-butoxycarbonyl-1,2,5,6-tetrahydropyrid-4-yl)phenyl)-5-(N-(t-butoxycarbonyl)isoxazol-3-ylaminomethyl)-4,5-dihydroisoxazole (817 mg, 1.51 mM) was treated with ethanolic hydrogen chloride under essentially the conditions of the equivalent intermediate of Example 1, to give the desired product directly from the reaction mixture after washing with diethyl ether (310 mg). MS(ESP): 343 (MH$^+$) for C$_{18}$H$_{19}$FN$_4$O$_2$ NMR (DMSO-d$_6$) δ: 2.65 (br, 2H); 3.19 (dd partly overlapped, 1H); 3.23 (overlapping m, 4H); 3.47 (dd, 1H); 3.71 (br, 2H); 4.91 (m, 1H); 5.97 (d, 1H); 6.09 (br, 1H); 7.46 (overlapping m, 3H); 8.34 (d, 1H); 9.51 (br, 2H).

1-t-Butoxycarbonyl-4-trimethylstannyl-1,2,5,6-tetrahydropyridine 1-t-butoxycarbonyl-4-trifluorosulfonyloxy-1,2,5,6-tetrahydropyridine (9.93 g, 0.03 M) was dissolved in anhydrous tetrahydrofuran (200 ml), lithium chloride (8.82 g, 0.21 M) and lithium carbonate (2.22 g, 0.03 M) added, and the mixture refluxed for 1 hour under nitrogen. Hexamethylditin (9.83 g, 0.03 M) and tetrakis(triphenylphosphine)palladium (1.73 g, 1.5 mM) were added, and refluxing continued for 18 hours. After cooling and filtering through celite, the solvent was evaporated, and the residual oil chromatographed on a 90 g Biotage silica column, eluting with 4% ethyl acetate in isohexane. Relevant fractions were combined to give the desired product as an oil (6.56 g). MS (ESP): 348 (MH$^+$) for C$_{13}$H$_{25}$NO$_2$Sn NMR (CDCl$_3$) δ: 0.01 (s, 9H); 1.35 (s, 9H); 2.16 (br, 2H); 3.34 (t, 2H); 3.79 (m, 2H); 5.64 (br, 1H).

EXAMPLE 29

The following illustrate representative pharmaceutical dosage forms containing a compound of the formula (I), an in-vivo hydrolysable ester or a pharmaceutically-acceptable salt thereof, including a pharmaceutically-acceptable salt of an in-vivo hydrolysable ester, (hereafter compound X), for therapeutic or prophylactic use in humans:

| Tablet I | mg/tablet |
| --- | --- |
| Compound X | 500 |
| Lactose Ph.Eur | 430 |
| Croscarmellose sodium | 40 |
| Polyvinylpyrrolidone | 20 |
| Magnesium stearate | 10 |

| Tablet II | mg/tablet |
| --- | --- |
| Compound X | 100 |
| Lactose Ph.Eur | 179 |
| Croscarmellose sodium | 12 |
| Polyvinylpyrrolidone | 6 |
| Magnesium stearate | 3 |

| Tablet III | mg/tablet |
| --- | --- |
| Compound X | 50 |
| Lactose Ph.Eur | 229 |
| Croscarmellose sodium | 12 |
| Polyvinylpyrrolidone | 6 |
| Magnesium stearate | 3 |

| Tablet IV | mg/tablet |
| --- | --- |
| Compound X | 1 |
| Lactose Ph.Eur | 92 |
| Croscarmellose sodium | 4 |
| Polyvinylpyrrolidone | 2 |
| Magnesium stearate | 1 |

| Capsule | mg/capsule |
| --- | --- |
| Compound X | 10 |
| Lactose Ph.Eur | 389 |
| Croscarmellose sodium | 100 |
| Magnesium stearate | 1 |

| Injection I | |
| --- | --- |
| Compound X | 50% w/v |
| Isotonic aqueous solution | to 100% |

-continued

| | | |
|---|---|---|
| Injection II (e.g. bolus) | | |
| Compound X | 10% w/v | |
| Isotonic aqueous solution | to 100% | |
| Injection III | | |
| Compound X | 5% w/v | |
| Isotonic aqueous solution | to 100% | |
| Injection IV (e.g. infusion) | | |
| Compound X | 1% w/v | |
| Isotonic aqueous solution | to 100% | |

Buffers, pharmaceutically-acceptable surfactants, oils or cosolvents such as polyethylene glycol, polypropylene glycol, glycerol or ethanol, glidants (such as silicon dioxide) or complexing agents such as a cyclodextrin (for example, hydroxy-propyl β-cyclodextrin or sulfo-butyl-ether β-cyclodextrin) may be used to aid formulation. Also, improvements in aqueous solubility, if desired, may be achieved, for example, by conjugation of a compound of formula (I) with a phospholipid (such as a (phospho)choline derivative) to form a micellar emulsion.

Note: The above formulations may be obtained by conventional procedures well known in the pharmaceutical art, for example as described in "Remington: The Science & Practice of Pharmacy" Vols. I & II (Ed. A. R. Gennaro (Chairman) et al; Publisher: Mack Publishing Company, Easton, Pa.; 19th Edition—1995) and "Pharmaceutics—The Science of Dosage Form Design" (Ed. M. E. Aulton; Publisher: Churchill Livingstone; first published 1988). The tablets (a)–(d) may be (polymer) coated by conventional means, for example to provide an enteric coating of cellulose acetate phthalate.

What is claimed is:

1. A compound of the formula (I), or a pharmaceutically-acceptable salt, or an in-vivo-hydrolysable ester thereof,

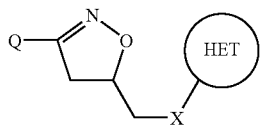

(I)

wherein
X is O, NH, S, SO or SO$_2$;
HET is a C-linked 5-membered heteroaryl ring containing 2 to 4 heteroatoms independently selected from N, O and S, which ring is optionally substituted on an available carbon atom by 1 or 2 substituents independently selected from (1–4C)alkyl, amino, (1–4C)alkylamino, (1–4C)alkoxy, (1–4C)alkoxycarbonyl and halogen, and/or on an available nitrogen atom (provided that the ring is not thereby quaternised) by (1–4C)alkyl; or
HET is a C-linked 6-membered heteroaryl ring containing 2 or 3 nitrogen heteroatoms, which ring is optionally substituted on any available C atom by 1, 2 or 3 substituents independently selected from (1–4C)alkyl, amino, (1–4C)alkylamino, (1–4C)alkoxy, (1–4C) alkoxycarbonyl and halogen;
Q is selected from Q1 to Q9:—

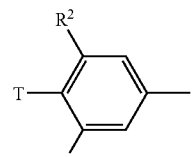 Q1

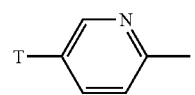 Q2

Q3

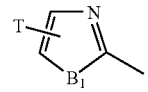 Q4

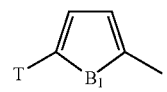 Q5

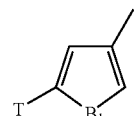 Q6

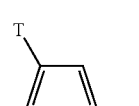 Q7

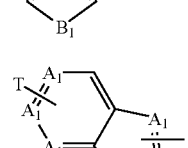 Q8

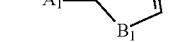 Q9

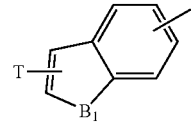

wherein R$^2$ and R$^3$ are independently hydrogen or fluoro;
wherein A$_1$ is carbon or nitrogen; B$_1$ is O or S (or, in Q9 only, NH); X$_q$ is O, S or N—R$^1$ (wherein R$^1$ is hydrogen, (1–4C)alkyl or hydroxyl-(1–4C)alkyl); and wherein
in Q7 each A$_1$ is independently selected from carbon or nitrogen, with a maximum of 2 nitrogen heteroatoms in the 6-membered ring, and Q7 is linked to T via any of the A$_1$ atoms (when A$_1$ is carbon), and linked in the 5-membered ring via the specified carbon atom, or via A$_1$ when A$_1$ is carbon; Q8 is linked to T via either of the specified carbon atoms in the 5-membered ring, and linked in the benzo-ring via either of the two specified carbon atoms on either side of the linking bond shown; and Q9 is linked via either of the two specified carbon atoms on either side of the linking bond shown;

wherein T is selected from the groups in (TA) to (TD) below (wherein AR1, AR2, AR2a, AR2b, AR3, AR3a, AR3b, AR4, AR4a CY1 and CY2 are defined hereinbelow);

(TA) T is selected from the following groups:—
(TAa) AR1, AR1-(1–4C)alkyl-, AR2 (carbon linked), AR3;
(TAb) AR1-CH(OH), AR2-CH(OH)—, AR3-CH(OH)—;
(TAc) AR1-CO—, AR2-CO—, AR3-CO—, AR4-CO—;
(TAd) AR1-O—, AR2-O—, AR3-O—;
(TAe) AR1-S(O)$_q$—, AR2-S(O)$_q$—, AR3-S(O)$_q$— (q is 0, 1 or 2);
(TAf) an optionally substituted N-linked (fully unsaturated) 5-membered heteroaryl ring system containing 1, 2 or 3 nitrogen atoms;
(TAg) a carbon linked tropol-3-one or tropol-4-one, optionally substituted in a position not adjacent to the linking position; or
(TB) T is selected from the following groups:—
(TBa) halo or (1–4C)alkyl
{optionally substituted by one or more groups each independently selected from hydroxy, (1–4C)alkoxy, (1–4C)alkanoyl, cyano, halo, trifluoromethyl, (1–4C)alkoxycarbonyl, —NRvRw, (1–6C)alkanoylamino, (1–4C)alkoxycarbonylamino, N-(1–4C)alkyl-N-(1–6C)alkanoylamino, (1–4C)alkylS(O)$_q$— (q is 0, 1 or 2), CY1, CY2 or AR1};
(TBb) —NRv$^1$Rw$^1$;
(TBc) ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-AR1)ethenyl, 2-(AR2)ethenyl;
(TBd) R$^{10}$CO—, R$^{10}$S(O)$_q$— (q is 0, 1 or 2) or R$^{10}$CS— wherein R$^{10}$ is selected from the following groups:—
(TBda) CY1 or CY2;
(TBdb) hydrogen, (1–4C)alkoxycarbonyl, trifluoromethyl, —NRvRw, ethenyl, 2-(1–4C)alkylethenyl, 2-cyanoethenyl, 2-cyano-2-((1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl or 2-(AR2)ethenyl; or
(TBdc) (1–4C)alkyl {optionally substituted as defined in (TBa) above, or by (1–4C)alkylS(O)$_p$NH— or (1–4C)alkylS(O)$_p$—((1–4C)alkyl)N— (p is 1 or 2)};
wherein Rv is hydrogen or (1–4C)alkyl; Rw is hydrogen or (1–4C)alkyl; Rv$^1$ is hydrogen, (1–4C)alkyl or (3–8C)cycloalkyl; Rw$^1$ is hydrogen, (1–4C)alkyl, (3–8C)cycloalkyl, (1–4C)alkyl-CO— or (1–4C)alkylS(O)$_q$— (q is 1 or 2); or
(TC) T is selected from the following groups:—
(TCa) an optionally substituted, fully saturated 4-membered monocyclic ring containing 1 heteroatom selected from O, N and S (optionally oxidised), and linked via a ring nitrogen or sp$^3$ carbon atom;
(TCb) an optionally substituted 5-membered monocyclic ring containing 1 heteroatom selected from O, N and S (optionally oxidised), and linked via a ring nitrogen atom or a ring sp$^3$ or sp$^2$ carbon atom, which monocyclic ring is fully saturated other than (where appropriate) at a linking sp$^2$ carbon atom;
(TCc) an optionally substituted 6- or 7-membered monocyclic ring containing 1 or 2 heteroatoms independently selected from O, N and S (optionally oxidised), and linked via a ring nitrogen atom or a ring sp$^3$ or sp$^2$ carbon atom, which monocyclic ring is filly saturated other than (where appropriate) at a linking sp$^2$ carbon atom; or (TD) T is selected from the following groups:—
(TDa) a bicyclic spiro-ring system containing 0, 1 or 2 ring nitrogen atoms as the only ring heteroatoms, the structure consisting of a 5- or 6-membered ring system (linked via a ring nitrogen atom or a ring sp$^3$ or sp$^2$ carbon atom) substituted (but not adjacent to the linking position) by a 3-, 4- or 5-membered spiro-carbon-linked ring; which bicyclic ring system is
(i) fully saturated other than (where appropriate) at a linking sp$^2$ carbon atom;
(ii) contains one —N(Rc)— group in the ring system (at least two carbon atoms away from the linking position when the link is via a nitrogen atom or an sp$^2$ carbon atom) or one —N(Rc)— group in an optional substituent (not adjacent to the linking position) and is
(iii) optionally further substituted on an available ring carbon atom; or
(TDb) a 7-, 8- or 9-membered bicyclic ring system (linked via a ring nitrogen atom or a ring sp$^3$ or sp$^2$ carbon atom) containing 0, 1 or 2 ring nitrogen atoms (and optionally a further O or S ring heteroatom), the structure containing a bridge of 1, 2 or 3 carbon atoms; which bicyclic ring system is
(i) fully saturated other than (where appropriate) at a linking sp$^2$ carbon atom;
(ii) contains one O or S heteroatom or one —N(Rc)— group in the ring (at least two carbon atoms away from the linking position when the link is via a nitrogen atom or an sp$^2$ carbon atom) or one —N(Rc)— group in an optional substituent (not adjacent to the linking position) and is
(iii) optionally further substituted on an available ring carbon atom;
wherein Rc is selected from groups (Rc1) to (Rc5):—
(Rc1) (1–6C)alkyl {optionally substituted by one or more (1–4C)alkanoyl groups (including geminal disubstitution) and/or optionally monosubstituted by cyano, (1–4C)alkoxy, trifluoromethyl, (1–4C)alkoxycarbonyl, phenyl (optionally substituted as for AR1 defined hereinafter), (1–4C)alkylS(O)$_q$— (q is 0, 1 or 2); or, on any but the first carbon atom of the (1–6C)alkyl chain, optionally substituted by one or more groups (including geminal disubstitution) each independently selected from hydroxy and fluoro, and/or optionally monosubstituted by oxo, —NRvRw [wherein Rv is hydrogen or (1–4C)alkyl; Rw is hydrogen or (1–4C)alkyl], (1–6C)alkanoylamino, (1–4C)alkoxycarbonylamino, N-(1–4C)alkyl-N-(1–6C)alkanoylamino, (1–4C)alkylS(O)$_p$NH— or (1–4C)alkylS(O)$_p$—((1–4C)alkyl)N— (p is 1 or 2)};
(Rc2) R$^{13}$CO—, R$^{13}$SO$_2$— or R$^{13}$CS—
wherein R$^{13}$ is selected from (Rc2a) to (Rc2e):—
(Rc2a) AR1, AR2, AR2a, AR2b, AR3, AR3a, AR3b, AR4, AR4a, CY1, CY2 or 2,2-dimethyl-1,3-dioxolane;
(Rc2b) hydrogen, (1–4C)alkoxycarbonyl, trifluoromethyl, —NRvRw [wherein Rv is hydrogen or (1–4C)alkyl; Rw is hydrogen or (1–4C)alkyl], ethenyl, 2-(1–4C)alkylethenyl, 2-cyanoethenyl, 2-cyano-2-(1–4C)alkyl)ethenyl, 2-nitroethenyl, 2-nitro-2-((1–4C)alkyl)ethenyl, 2-((1–4C)alkylaminocarbonyl)ethenyl, 2-((1–4C)alkoxycarbonyl)ethenyl, 2-(AR1)ethenyl, 2-(AR2)ethenyl, 2-(AR2a)ethenyl;
(Rc2c) (1–10C)alkyl
{optionally substituted by one or more groups (including geminal disubstitution) each independently selected from hydroxy, (1–10C)alkoxy, (1–4C)alkoxy-(1–4C)alkoxy, (1–4C)alkoxyl-(1–4C)alkoxy-(1–4C)alkoxy, (1–4C)alkanoyl, phosphoryl [—O—P(O)(OH)$_2$, and mono- and di-(1–4C)alkoxy derivatives thereof], phosphiryl [—O—P(OH)$_2$ and mono- and di-(1–4C)alkoxy derivatives thereof], and amino; and/or optionally substituted by one group selected from carboxy, phosphonate [phosphono, —P(O)(OH)$_2$, and mono- and di-(1–4C)alkoxy derivatives thereof], phosphinate [—P(OH)$_2$ and mono- and di-(1–4C)alkoxy derivatives thereof], cyano, halo, trifluoromethyl, (1–4C)alkoxycarbonyl, (1–4C)alkoxy-(1–4C)alkoxycarbonyl, (1–4C)alkoxy-(1–4C)alkoxy-(1–4C)alkoxycarbonyl, (1–4C)alkylamino, di((1–4C)alkyl)amino, (1–6C)alkanoylamino, (1–4C)alkoxycarbonylamino, N-(1–4C)alkyl-N-(1–6C)alkanoylamino, (1–4C)alkylaminocarbonyl, di((1–4C)alkyl)aminocarbonyl, (1–4C)alkylS(O)$_p$NH—, (1–4C)alkylS(O)$_p$—((1–4C)alkyl)N—, fluoro(1–4C)alkylS(O)$_p$NH—, fluoro(1–4C)alkylS(O)$_p$((1–4C)alkyl)N—, (1–4C)alkylS(O)$_q$—, CY1, CY2, AR1, AR2, AR3, AR1-O—, AR2-O—, AR3-O—, AR1-S(O)$_q$—, AR2-S(O)$_q$—, AR3-S(O)$_q$—, AR1-NH—, AR2-NH—, AR3-NH— (p is 1 or 2 and q is 0, 1 or 2), and also AR2a, AR2b, AR3a and AR3b versions of AR2 and AR3 containing groups};

(Rc2d) R$^{14}$C(O)O(1–6C)alkyl wherein R$^{14}$ is AR1, AR2, (1–4C)alkylamino, benzyloxy-(1–4C)alkyl or (1–10C)alkyl {optionally substituted as defined for (Rc2c)};

(Rc2e) R$^{15}$O— wherein R$^{15}$ is benzyl, (1–6C)alkyl {optionally substituted as defined for (Rc2c)}, CY1, CY2 or AR2b;

(Rc3) hydrogen, cyano, 2-cyanoethenyl, 2-cyano-2-((1–4C)alkyl)ethenyl, 2-((1–4C)alkylaminocarbonyl)ethenyl, 2-((1–4C)alkoxycarbonyl)ethenyl, 2-nitroethenyl, 2-nitro-2-((1–4C)alkyl)ethenyl, 2-(AR1)ethenyl, 2-(AR2)ethenyl, or of the formula (Rc3a)

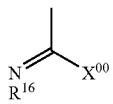

(Rc3a)

wherein X$^{00}$ is —OR$^{17}$, —SR$^{17}$, —NHR$^{17}$ and —N(R$^{17}$)$_2$;

wherein R$^{17}$ is hydrogen (when X$^{00}$ is —NHR$^{17}$ and —N(R$^{17}$)$_2$), and R$^{17}$ is (1–4C)alkyl, phenyl or AR2 (when X$^{00}$ is —OR$^{17}$, —SR$^{17}$ and —NHR$^{17}$); and R$^{16}$ is cyano, nitro, (1–4C)alkylsulfonyl, (4–7C)cycloalkylsulfonyl, phenylsulfonyl, (1–4C)alkanoyl and (1–4C)alkoxycarbonyl;

(Rc4) trityl, AR1, AR2, AR2a, AR2b, AR3, AR3a, AR3b;

(Rc5) RdOC(Re)=CH(C=O)—, RfC(=O)C(=O)—, RgN=C(Rh)C(=O)— or RiNHC(Rj)=CHC(=O)— wherein Rd is (1–6C)alkyl; Re is hydrogen or (1–6C)alkyl, or Rd and Re together form a (3–4C)alkylene chain; Rf is hydrogen, (1–6C)alkyl, hydroxy(1–6C)alkyl, (1–6C)alkoxy(1–6C)alkyl, —NRvRw [wherein Rv is hydrogen or (1–4C)alkyl; Rw is hydrogen or (1–4C)alkyl], (1–6C)alkoxy, (1–6C)alkoxy(1–6C)alkoxy, hydroxy(2–6C)alkoxy, (1–4C)alkylamino(2–6C)alkoxy, di-(1–4C)alkylamino(2–6C)alkoxy; Rg is (1–6C)alkyl, hydroxy or (1–6C)alkoxy; Rh is hydrogen or (1–6C)alkyl; R$^1$ is hydrogen, (1–6C)alkyl, AR1, AR2, AR2a, AR2b and Rj is hydrogen or (1–6C)alkyl; wherein AR1 is an optionally substituted phenyl or optionally substituted naphthyl;

AR2 is an optionally substituted 5- or 6-membered, fully unsaturated (i.e with the maximum degree of unsaturation) monocyclic heteroaryl ring containing up to four heteroatoms independently selected from O, N and S (but not containing any O—O, O—S or S—S bonds), and linked via a ring carbon atom, or a ring nitrogen atom if the ring is not thereby quaternised;

AR2a is a partially hydrogenated version of AR2 (i.e. AR2 systems retaining some, but not the full, degree of unsaturation), linked via a ring carbon atom or linked via a ring nitrogen atom if the ring is not thereby quaternised;

AR2b is a fully hydrogenated version of AR2 (i.e. AR2 systems having no unsaturation), linked via a ring carbon atom or linked via a ring nitrogen atom;

AR3 is an optionally substituted 8-, 9- or 10-membered, fully unsaturated (i.e with the maximum degree of unsaturation) bicyclic heteroaryl ring containing up to four heteroatoms independently selected from O, N and S (but not containing any O—O, O—S or S—S bonds), and linked via a ring carbon atom in either of the rings comprising the bicyclic system;

AR3a is a partially hydrogenated version of AR3 (i.e. AR3 systems retaining some, but not the full, degree of unsaturation), linked via a ring carbon atom, or linked via a ring nitrogen atom if the ring is not thereby quaternised, in either of the rings comprising the bicyclic system;

AR3b is a fully hydrogenated version of AR3 (i.e. AR3 systems having no unsaturation), linked via a ring carbon atom, or linked via a ring nitrogen atom, in either of the rings comprising the bicyclic system;

AR4 is an optionally substituted 13- or 14-membered, fully unsaturated (i.e with the maximum degree of unsaturation) tricyclic heteroaryl ring containing up to four heteroatoms independently selected from O, N and S (but not containing any O—O, O—S or S—S bonds), and linked via a ring carbon atom in any of the rings comprising the tricyclic system;

AR4a is a partially hydrogenated version of AR4 (i.e. AR4 systems retaining some, but not the full, degree of unsaturation), linked via a ring carbon atom, or linked via a ring nitrogen atom if the ring is not thereby quaternised, in any of the rings comprising the tricyclic system;

CY1 is an optionally substituted cyclobutyl, cyclopentyl or cyclohexyl ring;

CY2 is an optionally substituted cyclopentenyl or cyclohexenyl ring.

2. A compound of the formula (I), or a pharmaceutically-acceptable salt, or an in-vivo-hydrolysable ester thereof, as claimed in claim 1 wherein the groups defined in (TCa) to (TCc) are defined by formulae (TC1) to (TC4):—

(TC1)

(TC2)

-continued

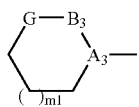
(TC3)

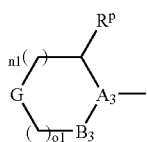
(TC4)

wherein in (TC1): >A₃—B₃— is >C(Rq)—CH(Rr)— and G is —O—, —S—, —SO—, —SO₂— or >N(Rc);

wherein in (TC2): m1 is 0, 1 or 2; >A₃—B₃— is >C=C(Rr)— or >C(Rq)—CH(Rr)— and G is —O—, —S—, —SO—, —SO₂— or >N(Rc);

wherein in (TC3): m1 is 0, 1 or 2; >A₃—B₃— is >C(Rq)—CH(Rr)— (other than when Rq and Rr are both together hydrogen) and G is —O—, —S—, —SO—, —SO₂— or >N(Rc);

wherein in (TC4): n1 is 1 or 2; o1 is 1 or 2 and n1+o1=2 or 3; >A₃—B₃— is >C=C(Rr)— or >C(Rq)—CH(Rr)— or >N—CH₂— and G is —O—, —S—, —SO—, —SO₂—, >SO₂-(1-4C)alkyl or >N(Rc); Rp is hydrogen, (1–4C)alkyl (other than when such substitution is defined by >A₃—B₃—), hydroxy, (1–4C)alkoxy or (1–4C)alkanoyloxy;

wherein in (TC), (TC2) and (TC4); m1, n1 and o1 are as defined hereinbefore: >A₃—B₃—is >N—CH₂— and G is >C(R¹¹)(R¹²), X=O, >C—OH, >C-(1–4C)alkoxy, >C=N—OH, >C=N-(1–4C)alkoxy, >C=N—NH-(1–4C)alkyl, C=N—N((1–4C)alkyl)₂ (the last two (1–4C)alkyl groups above in G being optionally substituted by hydroxy) or >C=N—N—CO-(1–4C)alkoxy; wherein > represents two single bonds;

Rq is hydrogen, hydroxy, halo, (1–4C)alkyl or (1–4C)alkanoyloxy;

Rr is (independently where appropriate) hydrogen or (1–4C)alkyl;

R¹¹ is hydrogen, (1–4C)alkyl, fluoro(1–4C)alkyl, (1–4C)alkyl-thio-(1–4C)alkyl or hydroxy-(1–4C)alkyl and R¹² is —[C(Rr)(Rr)]ₘ₂—N(Rr)(Rc) wherein m2 is 0, 1 or 2;

and, other than the ring substitution defined by G, >A₃—B₃— and Rp, each ring system may be optionally further substituted on a carbon atom not adjacent to the link at >A₃— by up to two substituents independently selected from (1–4C)alkyl, fluoro(1–4C)alkyl (including trifluoromethyl), (1–4C)alkyl-thio-(1–4C)alkyl, hydroxy-(1–4C)alkyl, amino, amino-(1–4C)alkyl, (1–4C)alkanoylamino, (1–4C)alkanoylamino-(1–4C)alkyl, carboxy, (1–4C)alkoxycarbonyl, AR-oxymethyl, AR-thiomethyl, oxo (=O) (other than when G is >N—Rc and Rc is group (Rc2) defined in claim 1) or independently selected from Rc; and also hydroxy or halo (the last two optional substituents only when G is —O— or —S—);

wherein AR is optionally substituted phenyl, optionally substituted phenyl(1–4C)alkyl, optionally substituted naphthyl, optionally substituted 5- or 6-membered heteroaryl;

optionally substituted 5/6 or 6/6 bicyclic heteroaryl ring system, in which the bicyclic heteroaryl ring systems may be linked via an atom in either of the rings comprising the bicyclic system, and wherein both the mono- and bicyclic heteroaryl ring systems are linked via a ring carbon atom and may be (partially) hydrogenated; and wherein Rc is as defined in claim 1.

3. A compound of the formula (I), or a pharmaceutically-acceptable salt, or an in-vivo-hydrolysable ester thereof, as claimed in claim 1 wherein the groups in (TCa) to (TCc) are defined by formulae (TC5) to (TC11):—

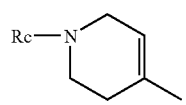
(TC5)

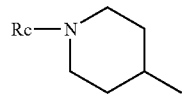
(TC6)

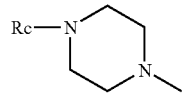
(TC7)

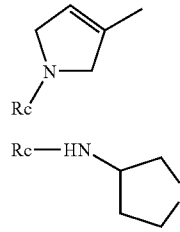
(TC8)

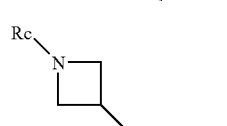
(TC9)

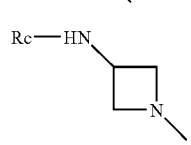
(TC10)

(TC11)

wherein Rc is as defined in claim 1.

4. A compound of the formula (I) as claimed in claim 1, being a compound of the formula (IC), or a pharmaceutically-acceptable salt, or an in-vivo-hydrolysable ester thereof

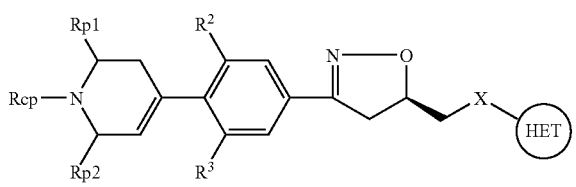
(IC)

wherein HET is isoxazol-3-yl, 1,2,4-oxadiazol-3-yl, isothiazol-3-yl or 1,2,5-thiadiazol-3-yl;

X is O, S or NH;

R² and R³ are independently hydrogen or fluoro; Rp1 and Rp2 are independently hydrogen, AR-oxymethyl or AR-thiomethyl (wherein AR is phenyl, phenyl-(1–4C) alkyl, naphthyl, furan, pyrrole, pyrazole, imidazole, triazole, pyrimidine, pyridazine, pyridine, isoxazole, oxazole, isothiazole, thiazole or thiophene), (1–4C) alkyl, carboxy, (1–4C)alkoxycarbonyl, hydroxymethyl, (1–4C)alkoxymethyl or carbamoyl and Rcp is cyano, pyrimidin-2-yl, 2-cyanoethenyl, 2-cyano-2-((1–4C)alkyl)ethenyl or Rcp is of the formula $R^{13p}CO—$, $R^{13p}SO_2—$ or $R^{13p}CS—$ (wherein $R^{13p}$ is hydrogen, (1–5C)alkyl [optionally substituted by one or more groups each independently selected from hydroxy and amino, or optionally monosubstituted by (1–4C)alkoxy, (1–4C)alkylS(O)$_q$—, (1 4C)alkylamino, (1–4C)alkanoyl, naphthoxy, (2–6C)alkanoylamino or (1–4C)alkylS(O)$_p$NH— wherein p is 1 or 2 and q is 0, 1 or 2], imidazole, triazole, pyrimidine, pyridazine, pyridine, isoxazole, oxazole, isothiazole, thiazole, pyridoimidazole, pyrimidoimidazole, quinoxaline, quinazoline, phthalazine, cinnoline or naphthyridine, or $R^{13p}$ is of the formula $R^{14p}C(O)0(1–6C)alkyl$ wherein $R^{14p}$ is (1–6C)alkyl), or Rcp is of the formula RfC(=O)C(=O)— wherein Rf is (1–6C)alkoxy.

5. A compound as claimed in claim 1 being (5RS-3-(3-Fluoro-4-imidazol-1-ylphenyl)-5-isoxazol-3-ylaminomethyl-4,5-dihydroisoxazole;

(5RS)-3-(3-Fluoro-4-imidazol-1-ylphenyl)-5-isoxazol-3-yloxymethyl-4,5-dihydroisoxazole or pharmaceutically-acceptable salts thereof.

6. A process for the preparation of a compound of the formula (I) as claimed in claim 1 or pharmaceutically-acceptable salts or in vivo hydrolysable esters thereof, which process comprises of (a) to (c):—

(a) modifying a substituent in or introducing a substituent into another compound of formula (I);

(b) reacting a compound of formula (II):

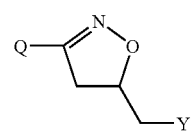

(II)

wherein Y is either (i) hydroxy; or (ii) a displaceable group with a compound of the formula (III-A) or (III-B):
HN(Pg)-HET or HX-HET
(III-A) (III-B)
wherein Pg is a suitable protecting group; or
(c) reacting a compound of formula (II) wherein Y is an amino group with a compound of the formula (IV):
Lg-HET
(IV)
wherein Lg is a leaving group; and thereafter if necessary:
(i) removing any protecting groups; (ii) forming a pharmaceutically-acceptable salt; (iii) forming an in-vivo hydrolysable ester, wherein Q, HET and X are as defined in claim 1.

7. A method for producing an antibacterial effect in a warm blooded animal which comprises administering to said animal an effective amount of a compound of the formula (I) as claimed in claim 1, or a pharmaceutically-acceptable salt, or in-vivo hydrolysable ester thereof.

8. A compound of the formula (I) as claimed in claim 1, or a pharmaceutically-acceptable salt, or in-vivo hydrolysable ester thereof, for use as a medicament.

9. A method for treating an antibacterial infection in a mammal in need thereof comprising administering a compound of claim 1 or a pharmaceutically acceptable salt thereof.

* * * * *